US007119081B2

(12) United States Patent
Potter et al.

(10) Patent No.: US 7,119,081 B2
(45) Date of Patent: Oct. 10, 2006

(54) OESTROGEN-17-SULPHAMATES AS INHIBITORS OF STEROID SULPHATASE

(75) Inventors: Barry Victor Lloyd Potter, Oxford (GB); Michael John Reed, Oxford (GB); Bertrand Leblond, Oxford (GB); Matthew Paul Leese, Oxford (GB); Atul Purohit, Oxford (GB)

(73) Assignee: Sterix Limited, Berkshire (GB)

( * ) Notice: Subject to any disclaimer, the term of this patent is extended or adjusted under 35 U.S.C. 154(b) by 0 days.

(21) Appl. No.: 10/367,114

(22) Filed: Feb. 14, 2003

(65) Prior Publication Data

US 2003/0225051 A1 Dec. 4, 2003

Related U.S. Application Data

(63) Continuation-in-part of application No. PCT/GB01/03688, filed on Aug. 17, 2001.

(30) Foreign Application Priority Data

Aug. 18, 2000 (GB) ................................ 0020498.2

(51) Int. Cl.
*A01N 1/00* (2006.01)
*A61K 31/56* (2006.01)
*C07J 1/00* (2006.01)

(52) U.S. Cl. ...................... 514/171; 514/178; 514/182; 552/623; 552/626; 552/635

(58) Field of Classification Search ................ 514/171, 514/178, 182, 177, 180; 552/623, 635, 626, 552/627
See application file for complete search history.

(56) References Cited

U.S. PATENT DOCUMENTS

| | | | | |
|---|---|---|---|---|
| 3,951,959 | A | 4/1976 | Prezewowsky et al. | |
| 6,011,024 | A * | 1/2000 | Reed et al. | 514/171 |
| 6,017,904 | A * | 1/2000 | Reed et al. | 514/75 |
| 6,080,735 | A | 6/2000 | Schwarz et al. | |
| 6,087,347 | A * | 7/2000 | Koizumi et al. | 514/80 |
| 6,159,960 | A * | 12/2000 | Reed et al. | 514/178 |
| 6,339,079 | B1 | 1/2002 | Kasch et al. | |
| 6,593,321 | B1 * | 7/2003 | Rao et al. | 514/182 |
| 6,677,325 | B1 * | 1/2004 | Reed et al. | 514/178 |

FOREIGN PATENT DOCUMENTS

| | | |
|---|---|---|
| AU | B-29741/95 | 3/1996 |
| DE | 100 06 155 A1 | 12/2000 |
| GB | 1479362 | 7/1974 |
| GB | 1479934 | 7/1974 |
| GB | 1482285 | 7/1974 |
| JP | 50-32160 | 3/1975 |
| JP | 50-32161 | 3/1975 |
| WO | WO 93/05064 | 3/1993 |
| WO | WO 96/05216 | 2/1996 |
| WO | WO 98/42729 | 1/1998 |
| WO | WO 99/64013 | 12/1999 |
| WO | WO 00/63228 | 10/2000 |
| WO | WO 01/44268 A1 | 6/2001 |
| WO | WO 01/51055 A2 | 7/2001 |
| WO | WO 01/77139 A1 | 10/2001 |

OTHER PUBLICATIONS

Woo, et al., "Oestrone 3-0-(N-Acetyl)Sulphamate, a Potential Molecular Probe of the Active Site of Oestrone Sulphatase," Bioorganic & Medicinal Chemistry Letters, vol. 7, No. 24, pp. 3075-3080, 1997.

Romer, et al., "Preparation and characterization of the sulfamates of estra-3, 17.xi.-diols. Rapid conversion of 16.alpha.-fluoroestradiol-3, 17.beta.-disul famate", J. Prakt. Chem. 1999, 341, No. 6.

Brunner, et al., "Synthese und Antitumoraktivitat von cis-Dichloroplatin(II)-Komplexen mit Ostradiolderivaten," Monatshefte fur Chemie, vol. 124, No. 1, pp. 83-102 (1993).

(Continued)

*Primary Examiner*—Sabiha N. Qazi
(74) *Attorney, Agent, or Firm*—Frommer Lawrence & Haug LLP; Thomas J. Kowalski; Angela M. Collison

(57) ABSTRACT

There is provided a compound of Formula I

Formula I

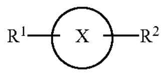

wherein X is a ring system; $R^1$ is any one of a sulphamate group, a phosphonate group, a thiophosphonate group, a sulphonate group or a sulphonamide group; $R^2$ is any one of a sulphamate group, a phosphonate group, a thiophosphonate group, a sulphonate group or a sulphonamide group; wherein when X is a steroidal structure and both of $R^1$ and $R^2$ are sulphamate groups, the steroidal ring system (X) represents an oestrogen; and wherein said compound is capable of inhibiting steroid sulphatase (STS) activity and/or is capable of acting as a modulator of cell cycling and/or as a modulator of apoptosis and/or as a modulator of cell growth. There is also provided a compound of Formula VIII Formula VIII

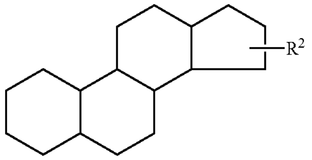

wherein $R^2$ is any one of a sulphamate group, a phosphonate group, a thiophosphonate group, a sulphonate group or a sulphonamide group; and wherein said compound is capable of inhibiting steroid sulphatase (STS) activity and/or is capable of acting as a modulator of cell cycling and/or as a modulator of apoptosis and/or as a modulator of cell growth.

11 Claims, 5 Drawing Sheets

OTHER PUBLICATIONS

Lokind, et al., "Oral bioavailability of 17.beta.-estradiol and produgs tested in rats, pigs and dogs," Int. J. Pharm. (1996), 127(2), 155-64, abstract.
Nedvidkova, et al., "Estrogenic effect of estradiol-sulfamate on the male rat anterior pituitary," J. Steroid Biochem. Mol. Biol. (1998), 67(4), abstract.
Kasch, et al., "In vitro selection of sulfatase inhibitors for tumor diagnosis with PET and for tumor therapy," Wiss.-Tech. Ber.-Forschungszent. Rossendorf (1999), FZR-283, abstract.
Nussbaumer, et al., "4,4'-Benzophenone-O,O'-disulfamate: A Potent Inhibitor of Steroid Sulfatase," Bioorganic & Medicinal Chemistry Letters 12 (2002) 2093-2095.
MacCarthy-Morrogh, et al., "Differential effects of estrone and estrone-3-O-sulfamate derivatives on mitotic. Arrest, apoptosis, and microtubule assembly in human breast cancer cells," Cancer Res 2000, 60 (19): 5441-50.
Schwarz, et al., "Synthesis of estrogen sulfamates: Compounds with a novel endocrinological profile," Steroids, 61:710-717, 1996.
Romer, et al., "C NMR Spectroscopic Characterization of Some Sulfamates of 3-Hydroxy-estra-1,3,5(10)-triene Derivatives".
Romer, et al., "Sulfamates of 3-Hydroxy-estra-1-3-5(10)-triene Derivatives".
Reed, et al., "The development of steroid sulphatase inhibitors," Endocrine-Related Cancer (1996) 3, 9-23.

* cited by examiner

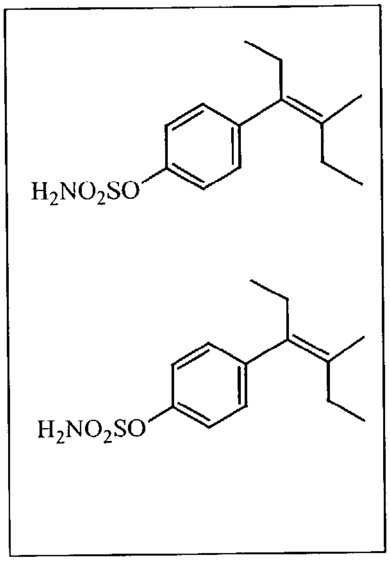
Fig. 1. Structures of diethylstilboestrol mono-sulphamate (1) and diethylstilboestrol bis-sulphamate (2).

Fig. 2 Structures of sulphamates 6 – 11, 14 – 16 and 20 – 21.
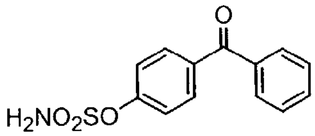
(6)
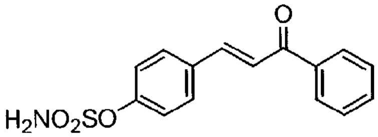
(7)
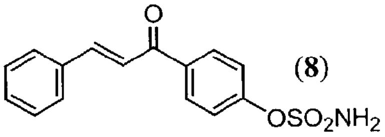
(8)
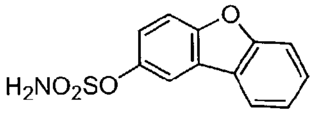
(9)
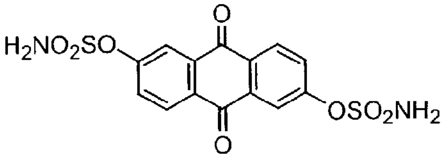
(10)
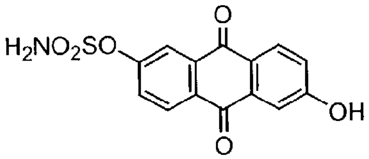
(11)
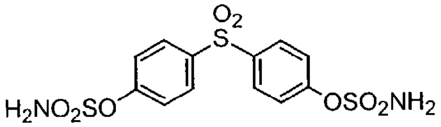
(14)
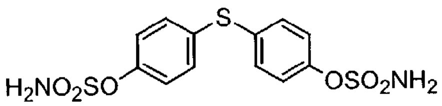
(15)
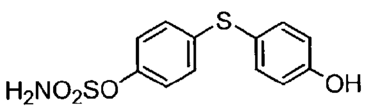
(16)
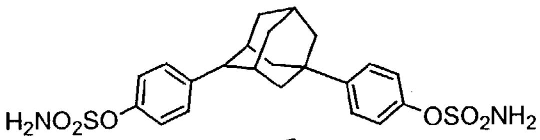
(20)
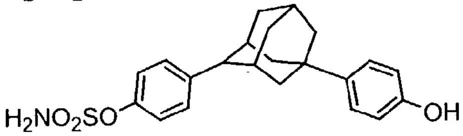
(21)

Fig. 3 In vivo results
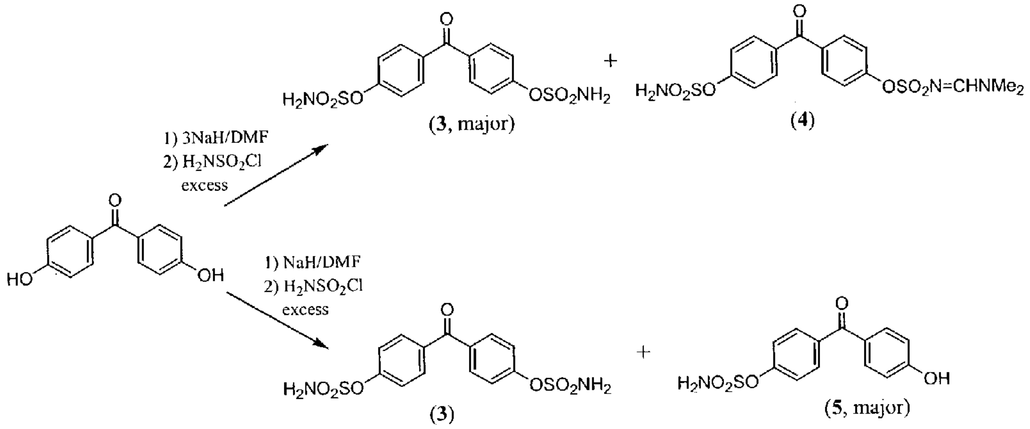
Scheme 1. Synthesis of benzophenone derivatives 3 – 5.
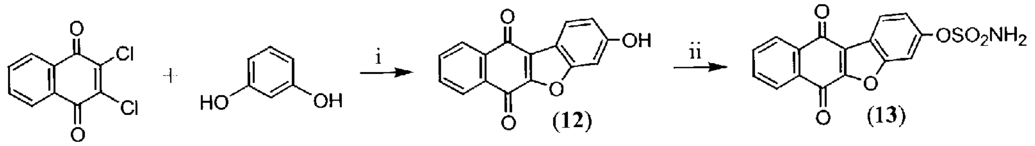
Scheme 2. Synthesis of benzo[*b*]naphtho[2,3-*d*]-furan-6,11-dione-3-*O*-sulphamate (13), (i) NaOEt/ethanol, 12 h.; (ii) NaH/DMF, $H_2NSO_2Cl$.

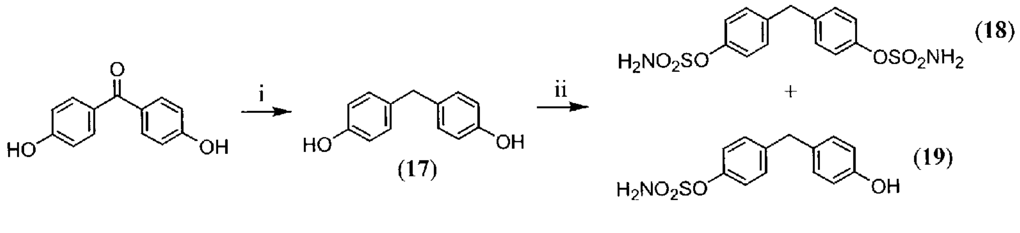
(17) (18) (19)
Scheme 3. Synthesis of diphenylmethane sulphamates (18 and 19): (i) Pd-C/96%ethanol, 6 h; (ii) NaH/DMF, $H_2NSO_2Cl$.
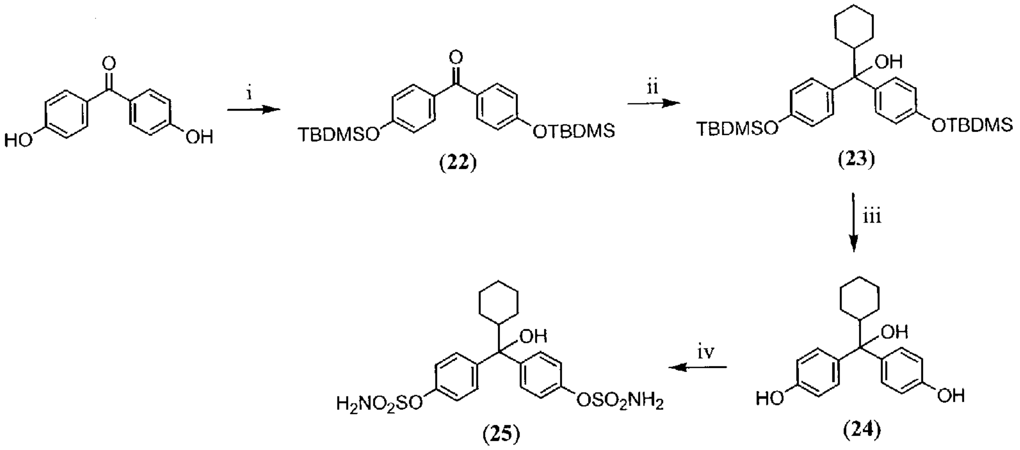
(22) (23) (24) (25)
Scheme 4. Synthesis of 1-cyclohexyl-1,1-(4,4'-*O*,*O*-bis-sulphamoylphenyl)methanol (25), (i) tert-butyldimethylchlorosilane/THF, imidazole, 3 h; (ii) cyclohexylmagnesium chloride/ether, 12 h; (iii) TBAF/THF, r.t., 10 min (iv) DBMP/dichloromethane, $H_2NSO_2Cl$, 2 h.

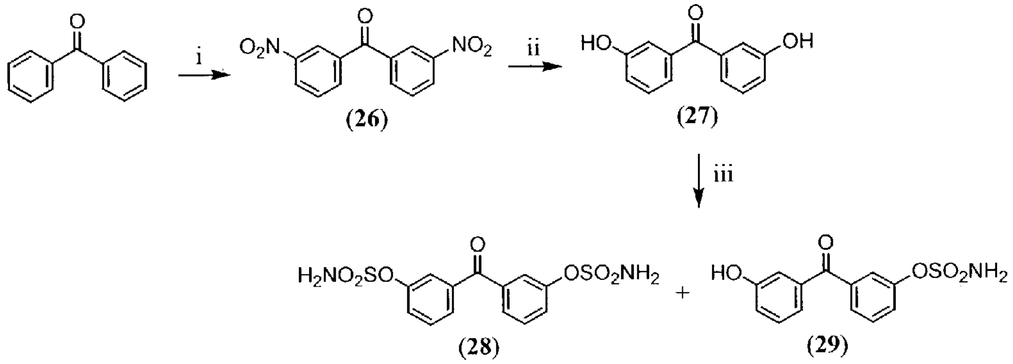
(26) (27) (28) (29)
Scheme 5. Synthesis of benzophenone-3′,3-*O*,*O*-bis-sulphamate (28) and 3′-hydroxybenzophenone 3-*O*-sulphamate (29): (i) $H_2SO_4/HNO_3$, 75 $^0C$, 30 min.; (ii) a) $SnCl_2/HCl$, 70 $^0C$, 6 h.; b) $NaNO_2/H_2SO_4$, 0 $^0C$ - Δ; (iii) NaH/DMF, $H_2NSO_2Cl$.

OESTROGEN-17-SULPHAMATES AS INHIBITORS OF STEROID SULPHATASE

CROSS-REFERENCE TO RELATED APPLICATIONS

This application is a continuation-in-part application of International Patent Application PCT/GB01/03688 filed Aug. 17, 2001 designating the U.S., and published as WO 02/16392 on Feb. 28, 2002, which claims priority to UK application number 0020498.2, filed Aug. 18, 2000.

Each of these applications and each of the documents cited in each of these applications ("application cited documents"), and each document referenced or cited in the application cited documents, either in the text or during the prosecution of those applications, as well as all arguments in support of patentability advanced during such prosecution, are hereby incorporated herein by reference. Various documents are also cited in this text ("application cited documents"). Each of the application cited documents, and each document cited or referenced in the application cited documents, is hereby incorporated herein by reference.

FIELD OF INVENTION

The present invention relates to a compound.

In particular the present invention relates to a compound and to a pharmaceutical composition comprising the compound. The present invention also relates to the use of the compound or composition in therapy applications.

BACKGROUND TO THE INVENTION

Evidence suggests that oestrogens are the major mitogens involved in promoting the growth of tumours in endocrine-dependent tissues, such as the breast and endometrium. Although plasma oestrogen concentrations are similar in women with or without breast cancer, breast tumour oestrone and oestradiol levels are significantly higher than in normal breast tissue or blood. In situ synthesis of oestrogen is thought to make an important contribution to the high levels of oestrogens in tumours and therefore inhibitors, in particular specific inhibitors, of oestrogen biosynthesis are of potential value for the treatment of endocrine-dependent tumours.

Over the past two decades, there has been considerable interest in the development of inhibitors of the aromatase pathway—which converts the androgen precursor androstenedione to oestrone. However, there is now evidence that the oestrone sulphatase (E1-STS) pathway, i.e. the hydrolysis of oestrone sulphate to oestrone (E1S to E1), as opposed to the aromatase pathway, is the major source of oestrogen in breast tumours. This theory is supported by a modest reduction of plasma oestrogen concentration in postmenopausal women with breast cancer treated by aromatase inhibitors, such as aminoglutethimide and 4-hydroxyandrostenedione, and also by the fact that plasma E1S concentration in these aromatase inhibitor-treated patients remains relatively high. The long half-life of E1S in blood (10–12 h) compared with the unconjugated oestrogens (20 min) and high levels of steroid sulphatase activity in liver and, normal and malignant breast tissues, also lend support to this theory.

PCT/GB92/01587 teaches novel steroid sulphatase inhibitors and pharmaceutical compositions containing them for use in the treatment of oestrone dependent tumours, especially breast cancer. These steroid sulphatase inhibitors are sulphamate esters, such as N,N-dimethyl oestrone-3-sulphamate and, preferably, oestrone-3-sulphamate (otherwise known as "EMATE"). EMATE has the following structure:

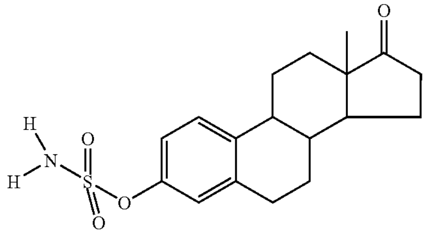

It is known that EMATE is a potent E1-STS inhibitor as it displays more than 99% inhibition of E1-STS activity in intact MCF-7 cells at 0.1 mM. EMATE also inhibits the E1-STS enzyme in a time- and concentration-dependent manner, indicating that it acts as an active site-directed inactivator. Although EMATE was originally designed for the inhibition of E1-STS, it also inhibits dehydroepiandrosterone sulphatase (DHA-STS), which is an enzyme that is believed to have a pivotal role in regulating the biosynthesis of the oestrogenic steroid androstenediol. Also, there is now evidence to suggest that androstenediol may be of even greater importance as a promoter of breast tumour growth. EMATE is also active in vivo as almost complete inhibition of rat liver E1-STS (99%) and DHA-STS (99%) activities resulted when it is administered either orally or subcutaneously. In addition, EMATE has been shown to have a memory enhancing effect in rats. Studies in mice have suggested an association between DHA-STS activity and the regulation of part of the immune response. It is thought that this may also occur in humans. The bridging O-atom of the sulphamate moiety in EMATE is important for inhibitory activity. Thus, when the 3-O-atom is replaced by other heteroatoms as in oestrone-3-N-sulphamate and oestrone-3-S-sulphamate, these analogues are weaker non-time-dependent inactivators.

Although optimal potency for inhibition of E1-STS may have been attained in EMATE, it is possible that oestrone may be released during sulphatase inhibition and that EMATE and its oestradiol congener may possess oestrogenic activity.

Ahmed et al (Biochem Biophys Res Commun 1999 Jan. 27; 254(3):811–5) report on a structure-activity relationship study of steroidal and nonsteroidal inhibitors of STS.

The present invention seeks to provide novel compounds suitable for the inhibition of E1-STS as well as other therapeutic applications.

SUMMARY ASPECTS OF THE PRESENT INVENTION

The present invention is based on the surprising finding that certain compounds could be used as effective steroid sulphatase inhibitors and/or as agents that can influence cell cycling and/or as agents that can influence apoptosis.

In one aspect, the present invention is based on the surprising finding that certain bissulphamate compounds and certain D ring substituted steroidal compounds could be used as effective steroid sulphatase inhibitors and/or as modulators of cell cycling and/or as modulators of apoptosis.

The compounds comprise at least two groups selected from a sulphamate group, a phosphonate group, a thiophosphonate group, a sulphonate group or a sulphonamide group. The ring system compounds comprise at least one ring component. That ring component comprises at least 4 atoms in the ring. Typically, those 4 atoms will be carbon atoms. Thus, typically, that ring component will be a hydrocarbyl group.

The compounds of the present invention may comprise other substituents. These other substituents may, for example, further increase the activity of the compounds of the present invention and/or increase stability (ex vivo and/or in vivo).

DETAILED ASPECTS OF THE PRESENT INVENTION

According to one aspect of the present invention, there is provided a compound of Formula I Formula I

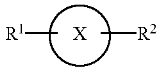

wherein X is a ring system; $R^1$ is any one of a sulphamate group, a phosphonate group, a thiophosphonate group, a sulphonate group or a sulphonamide group; $R^2$ is any one of a sulphamate group, a phosphonate group, a thiophosphonate group, a sulphonate group or a sulphonamide group; wherein when X is a steroidal structure and both of $R^1$ and $R^2$ are sulphamate groups, the steroidal ring system (X) represents an oestrogen; and wherein said compound is capable of inhibiting steroid sulphatase (STS) activity and/or is capable of acting as a modulator of cell cycling and/or as a modulator of apoptosis and/or as a modulator of cell growth.

According to one aspect of the present invention, there is provided a compound of Formula VIII Formula VIII

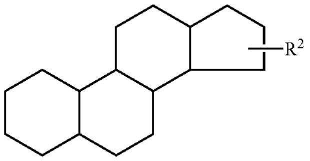

wherein $R^2$ is any one of a sulphamate group, a phosphonate group, a thiophosphonate group, a sulphonate group or a sulphonamide group; and wherein said compound is capable of inhibiting steroid sulphatase (STS) activity and/or is capable of acting as a modulator of cell cycling and/or as a modulator of apoptosis and/or as a modulator of cell growth.

According to one aspect of the present invention, there is provided a method comprising (a) performing a steroid sulphatase assay with one or more candidate compounds of Formula I; (b) determining whether one or more of said candidate compounds is/are capable of modulating STS activity and/or cell cycling and/or cell growth and/or apoptosis; and (c) selecting one or more of said candidate compounds that is/are capable of modulating STS activity and/or cell cycling and/or cell growth and/or apoptosis.

According to one aspect of the present invention, there is provided a method comprising (a) performing a steroid sulphatase assay with one or more candidate compounds having of Formula I; (b) determining whether one or more of said candidate compounds is/are capable of inhibiting STS activity; and (c) selecting one or more of said candidate compounds that is/are capable of inhibiting STS activity and/or cell cycling and/or cell growth and/or apoptosis.

In any one of the methods of the present invention, one or more additional steps may be present. For example, the method may also include the step of modifying the identified candidate compound (such as by chemical and/or enzymatic techniques) and the optional additional step of testing that modified compound for STS inhibition effects (which may be to see if the effect is greater or different). By way of further example, the method may also include the step of determining the structure (such as by use of crystallographic techniques) of the identified candidate compound and then performing computer modelling studies—such as to further increase its STS inhibitory action. Thus, the present invention also encompasses a computer having a dataset (such as the crystallographic co-ordinates) for said identified candidate compound. The present invention also encompasses that identified candidate compound when presented on a computer screen for the analysis thereof—such as protein binding studies.

According to one aspect of the present invention, there is provided a compound identified by the method of the present invention.

According to one aspect of the present invention, there is provided a compound according to the present invention for use in medicine.

According to one aspect of the present invention, there is provided a pharmaceutical composition comprising the compound according to the present invention optionally admixed with a pharmaceutically acceptable carrier, diluent, excipient or adjuvant.

According to one aspect of the present invention, there is provided the use of a compound according to the present invention in the manufacture of a medicament for use in the therapy of a condition or disease associated with STS and/or cell cycling and/or apoptosis and/or cell growth.

According to one aspect of the present invention, there is provided the use of a compound according to the present invention in the manufacture of a medicament for use in the therapy of a condition or disease associated with adverse STS levels and/or cell cycling and/or apoptosis and/or cell growth.

The present invention also encompasses the novel compounds of the present invention (such as those presented herein), as well as processes for making same (such as the processes presented herein) as well as novel intermediates (such as those presented herein) for use in those processes.

For ease of reference, these and further aspects of the present invention are now discussed under appropriate section headings. However, the teachings under each section are not necessarily limited to each particular section.

Preferable Aspects

In a preferred aspect In a preferred aspect the ring system is a polycyclic system. For the avoidance of doubt ring X of general formula I may represent one or more rings. The rings may be fused, non-fused or a combination of fused and non-fused.

In a preferred aspect the ring system is of the formula

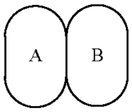

In a preferred aspect the ring system comprises at least three rings.

In a preferred aspect the ring system is of the formula

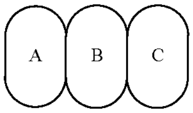

In a preferred aspect the ring system comprises at lest four rings.

In a preferred aspect the ring system is of the formula

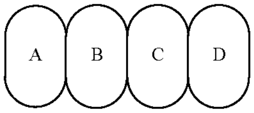

In a preferred aspect $R^1$ is attached to ring A.

In a preferred aspect $R^2$ is attached to ring B.

In a preferred aspect $R^2$ is attached to ring C.

In a preferred aspect $R^2$ is attached to ring D.

In a highly preferred aspect $R^1$ is attached to ring A and $R^2$ is attached to ring B.

In a highly preferred aspect $R^1$ is attached to ring A and $R^2$ is attached to ring C.

In a highly preferred aspect $R^1$ is attached to ring A and $R^2$ is attached to ring D.

In a preferred aspect the ring system is a steroidal or mimics a steroidal ring.

In a preferred aspect the ring system is a steroidal.

In a preferred aspect the ring system oestrogenic. More preferably the ring system is an oestrogen.

In a preferred aspect the ring system is selected from oestrone and oestradiol.

In a preferred aspect the compound has the Formula II

Formula Ia

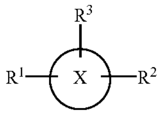

wherein $R^3$ is a hydrocarbyl or oxyhydrocarbyl group.

In a preferred aspect the compound has the Formula II

Formula II

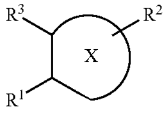

wherein $R^3$ is a hydrocarbyl or oxyhydrocarbyl group.

In a preferred aspect $R^3$ is an oxyhydrocarbon group.

In a preferred aspect $R^3$ is an alkoxy group, preferably methoxy.

In a further preferred aspect $R^3$ is an hydrocarbyl group, for example an alkyl group, preferably methyl or ethyl.

In a preferred aspect the compound has Formula IV

Formula IV

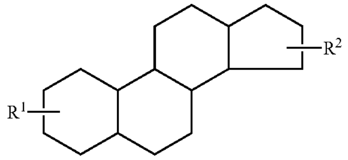

In a preferred aspect the compound has Formula V

Formula V

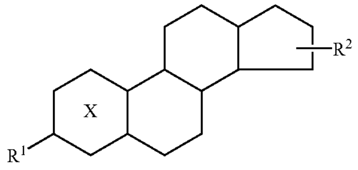

In a preferred aspect the compound has Formula VI

Formula VI

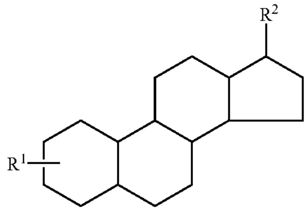

In a preferred aspect the compound has Formula VII

Formula VII

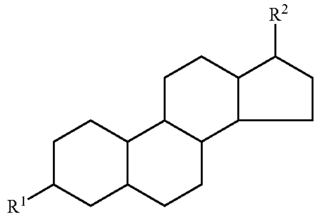

Preferably $R^1$ is a sulphamate group.

Preferably $R^2$ is a sulphamate group.

Preferably $R^1$ and $R^2$ are sulphamate groups.

In a preferred aspect the compound of the present invention comprises at least two sulphamate groups, wherein said sulphamate groups are not on the same ring.

In a preferred aspect the sulphamate group is of the formula

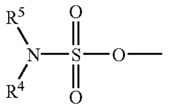

wherein each of $R^4$ and $R^5$ is independently selected from H and hydrocarbyl.

In a preferred aspect each of $R^4$ and $R^5$ of the sulphamate is independently selected from H, alkyl, cycloalkyl, alkenyl and aryl, or together represent alkylene optionally containing one or more hetero atoms or groups in the alkylene chain.

In a preferred aspect at least one of $R^4$ and $R^5$ is H.

In a highly preferred aspect both of $R^4$ and $R^5$ are H.

As discussed above the present invention provides compounds of Formula VIII

Formula VIII

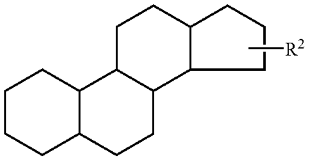

wherein $R^2$ is any one of a sulphamate group, a phosphonate group, a thiophosphonate group, a sulphonate group or a sulphonamide group; and wherein said compound is capable of inhibiting steroid sulphatase (STS) activity and/or is capable of acting as a modulator of cell cycling and/or as a modulator of apoptosis and/or as a modulator of cell growth.

In a preferred aspect the compound of Formula VIII has Formula IX

Formula IX

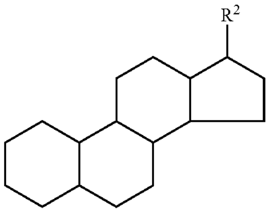

In a preferred aspect $R^2$ of compound of Formula VIII or Formula IX is a sulphamate group.

In a preferred aspect $R^2$ of compound of Formula VIII or Formula IX is a sulphamate group is of the formula

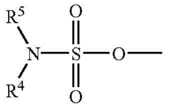

wherein each of $R^4$ and $R^5$ is independently selected from H and hydrocarbyl.

In a preferred aspect $R^2$ of compound of Formula VIII or Formula IX is a sulphamate group is of the formula

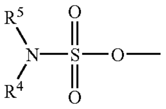

wherein each of $R^4$ and $R^5$ is independently selected from H, alkyl, cycloalkyl, alkenyl, C(O)alkyl, aryl, arylalkyl or together represent alkylene optionally containing one or more hetero atoms or groups in the alkylene chain.

Preferably at least one of $R^4$ and $R^5$ is H.

Preferably both of $R^4$ and $R^5$ are H.

In a preferred aspect $R^2$ of compound of Formula VIII or Formula IX is a sulphamate group is of the formula

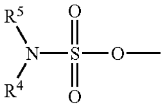

wherein each of $R^4$ and $R^5$ is independently selected from H, $C(O)CH_3$, $(CH2)_4CH_3$, $CH_2C_6H_5$, and $CH_3$.

In a preferred aspect the compound of Formula VIII has Formula X

Formula X

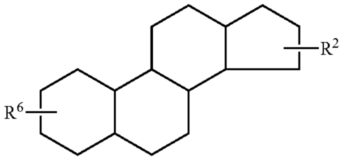

wherein $R^6$ is OH or an oxyhydrocarbyl group

In a preferred aspect the compound of Formula VIII has Formula XI

Formula XI

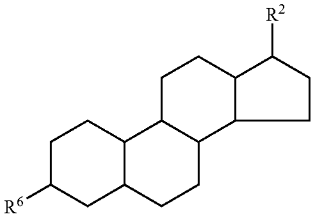

wherein $R^6$ is OH or an oxyhydrocarbyl group

Preferably $R^6$ of formula X or XI is an oxyhydrocarbyl group. Preferably the oxyhydrocarbyl group is $O(CH_2)_n C_6H_5$ wherein n is from 1 to 10, preferably 1 to 5, preferably 1, 2 or 3

Preferably the ring system will contain, inclusive of all substituents, a maximum of about 50 carbon atoms, more usually no more than about 30 to 40 carbon atoms.

For some applications, preferably the compounds have no, or a minimal, oestrogenic effect.

For some applications, preferably the compounds have an oestrogenic effect.

For some applications, preferably the compounds have a reversible action.

For some applications, preferably the compounds have an irreversible action.

In one embodiment, the compounds of the present invention are useful for the treatment of breast cancer.

The present invention also covers novel intermediates that are useful to prepare the compounds of the present invention. For example, the present invention covers novel alcohol precursors for the compounds. By way of further example, the present invention covers bis protected precursors for the compounds. Examples of each of these precursors are presented herein. The present invention also encompasses a process comprising each or both of those precursors for the synthesis of the compounds of the present invention.

One key aspect of the present invention is that the sulphamate compounds of the present invention can act as STS inhibitors.

Another aspect of the compounds of the present invention is that they may be potent in vivo.

Some of the compounds of the present invention may be non-oestrogenic compounds. Here, the term "non-oestrogenic" means exhibiting no or substantially no oestrogenic activity.

Another aspect is that some of the compounds may not be capable of being metabolised to compounds which display or induce hormonal activity.

Some of the compounds of the present invention are also advantageous in that they may be orally active.

Some of the compounds of the present invention may useful for the treatment of cancer, such as breast cancer, as well as (or in the alternative) non-malignant conditions, such as the prevention of auto-immune diseases, particularly when pharmaceuticals may need to be administered from an early age.

Thus, some of the compounds of the present invention are also believed to have therapeutic uses other than for the treatment of endocrine-dependent cancers, such as the treatment of autoimmune diseases.

The compounds of the present invention may also be useful as an inducer of apoptosis.

The compounds of the present invention may also be useful as a cell growth inhibitors.

Steroid Sulphatase

Steroid sulphatase—which is sometimes referred to as steroid sulfatase or steryl sulphatase or "STS" for short—hydrolyses several sulphated steroids, such as oestrone sulphate, dehydroepiandrosterone sulphate and cholesterol sulphate. STS has been allocated the enzyme number EC 3.1.6.2.

STS has been cloned and expressed. For example see Stein et al (J. Biol. Chem. 264:13865–13872 (1989)) and Yen et al (Cell 49:443–454(1987)).

STS is an enzyme that has been implicated in a number of disease conditions.

By way of example, workers have found that a total deficiency in STS produces ichthyosis. According to some workers, STS deficiency is fairly prevalent in Japan. The same workers (Sakura et al, J Inherit Metab Dis 1997 November; 20(6):807–10) have also reported that allergic diseases—such as bronchial asthma, allergic rhinitis, or atopic dermatitis—may be associated with a steroid sulphatase deficiency.

In addition to disease states being brought on through a total lack of STS activity, an increased level of STS activity may also bring about disease conditions. By way of example, and as indicated above, there is strong evidence to support a role of STS in breast cancer growth and metastasis.

STS has also been implicated in other disease conditions. By way of example, Le Roy et al (Behav Genet 1999 March; 29(2):131–6) have determined that there may be a genetic correlation between steroid sulphatase concentration and initiation of attack behaviour in mice. The authors conclude that sulphatation of steroids may be the prime mover of a complex network, including genes shown to be implicated in aggression by mutagenesis.

STS Inhibition

It is believed that some disease conditions associated with STS activity are due to conversion of a nonactive, sulphated oestrone to an active, nonsulphated oestrone. In disease conditions associated with STS activity, it would be desirable to inhibit STS activity.

Here, the term "inhibit" includes reduce and/or eliminate and/or mask and/or prevent the detrimental action of STS.

STS Inhibitor

In accordance with the present invention, the compound of the present invention is capable of acting as an STS inhibitor.

Here, the term "inhibitor" as used herein with respect to the compound of the present invention means a compound that can inhibit STS activity—such as reduce and/or eliminate and/or mask and/or prevent the detrimental action of STS. The STS inhibitor may act as an antagonist.

The ability of compounds to inhibit oestrone sulphatase activity can be assessed using either intact MCF-7 breast cancer cells or placental microsomes. In addition, an animal model may be used. Details on suitable Assay Protocols are presented in following sections. It is to be noted that other assays could be used to determine STS activity and thus STS inhibition. For example, reference may also be made to the teachings of WO-A-99/50453.

Preferably, for some applications, the compound is further characterised by the feature that if the sulphamate group were to be substituted by a sulphate group to form a sulphate derivative, then the sulphate derivative would be hydrolysable by an enzyme having steroid sulphatase (E.C. 3.1.6.2) activity—i.e. when incubated with steroid sulphatase EC 3.1.6.2 at pH 7.4 and 37° C.

In one preferred embodiment, if the sulphamate group of the compound were to be replaced with a sulphate group to form a sulphate compound then that sulphate compound would be hydrolysable by an enzyme having steroid sulphatase (E.C. 3.1.6.2) activity and would yield a Km value of less than 200 mmolar, preferably less than 150 mmolar, preferably less than 100 mmolar, preferably less than 75 mmolar, preferably less than 50 mmolar, when incubated with steroid sulphatase EC 3.1.6.2 at pH 7.4 and 37° C.

In a preferred embodiment, the compound of the present invention is not hydrolysable by an enzyme having steroid sulphatase (E.C. 3.1.6.2) activity.

For some applications, preferably the compound of the present invention has at least about a 100 fold selectivity to a desired target (e.g. STS), preferably at least about a 150 fold selectivity to the desired target, preferably at least about a 200 fold selectivity to the desired target, preferably at least about a 250 fold selectivity to the desired target, preferably at least about a 300 fold selectivity to the desired target, preferably at least about a 350 fold selectivity to the desired target.

It is to be noted that the compound of the present invention may have other beneficial properties in addition to or in the alternative to its ability to inhibit STS activity.

Group K

When X is a single ring it may be substituted with a hydrocarbyl Group K. Thus in this aspect the present provides a compound of Formula XII Formula XII

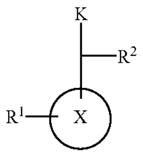

wherein X is a ring; K is a hydrocarbyl group; $R^1$ is any one of a sulphamate group, a phosphonate group, a thiophosphonate group, a sulphonate group or a sulphonamide group; $R^2$ is any one of a sulphamate group, a phosphonate group, a thiophosphonate group, a sulphonate group or a sulphonamide group; wherein when X is a steroidal structure and both of $R^1$ and $R^2$ are sulphamate groups, the steroidal ring system (X) represents an oestrogen; and wherein said compound is capable of inhibiting steroid sulphatase (STS) activity and/or is capable of acting as a modulator of cell cycling and/or as a modulator of apoptosis and/or as a modulator of cell growth.

Group K need not be a cyclic structure. In this regard, group K may be a linear structure that may have the ability to conform to a ring like structure when in in vivo.

In a preferred aspect, group K is cyclic—so as to form the cyclic group K.

Cyclic group K need not necessarily be fused to ring X. In this regard, they may be separated by a suitable spacer group—which may be a hydrocarbyl group.

In a preferred aspect, cyclic group K is fused to ring X.

Group K may be a polycyclic group, which need not be a fused polycycle.

Thus, in a preferred aspect, group K and ring X make up a polycyclic compound. As indicated, here the term "polycyclic" includes fused and non-fused ring structures including combinations thereof.

At least one of the cyclic groups K and X may be a heterocyclic group (a heterocycle) or a non-heterocyclic group.

At least one of the cyclic groups K and X may be a saturated ring structure or an unsaturated ring structure (such as an aryl group).

Preferably, at least one of the cyclic groups is an aryl ring.

If the cyclic group is polycyclic some or all of the ring components of the compound may be fused together or joined via one or more suitable spacer groups.

The polycyclic compound may comprise a number of fused rings. In this aspect the fused rings may comprise any combination of different size rings, such as 3 six-membered rings (6, 6, 6), a six-membered ring, a seven-membered ring and a six-membered ring (6, 7, 6), a six-membered ring and two eight-membered rings (6, 8, 8) etc.

In one aspect the present invention relates to compounds wherein the polycyclic compounds are other than (6, 6, 7) rings. In a further aspect, the present invention relates to compounds wherein the polycyclic compounds only contain rings having other than 7 members.

Preferably the polycyclic compound will contain, inclusive of all substituents, no more than 50 about carbon atoms, more usually no more than about 30 to 40 carbon atoms.

The polycyclic compound can comprise at least two ring components, or at least three ring components, or at least four ring components.

Preferably, the polycyclic compound comprises four ring components.

Preferred polycyclic compounds have a steroidal ring component, or bio-isosteres thereof.

Hydrocarbyl

The term "hydrocarbyl group" as used herein means a group comprising at least C and H and may optionally comprise one or more other suitable substituents. Examples of such substituents may include halo, alkoxy, nitro, an alkyl group, a cyclic group etc. In addition to the possibility of the substituents being a cyclic group, a combination of substituents may form a cyclic group. If the hydrocarbyl group comprises more than one C then those carbons need not necessarily be linked to each other. For example, at least two of the carbons may be linked via a suitable element or group. Thus, the hydrocarbyl group may contain hetero atoms. Suitable hetero atoms will be apparent to those skilled in the art and include, for instance, sulphur, nitrogen and oxygen. A non-limiting example of a hydrocarbyl group is an acyl group.

A typical hydrocarbyl group is a hydrocarbon group. Here the term "hydrocarbon" means any one of an alkyl group, an alkenyl group, an alkynyl group, which groups may be linear, branched or cyclic, or an aryl group. The term hydrocarbon also includes those groups but wherein they have been optionally substituted. If the hydrocarbon is a branched structure having substituent(s) thereon, then the substitution may be on either the hydrocarbon backbone or on the branch; alternatively the substitutions may be on the hydrocarbon backbone and on the branch.

Sulphamate Group

In one embodiment, the ring X has a sulphamate group as a substituent. The term "sulphamate" as used herein includes an ester of sulphamic acid, or an ester of an N-substituted derivative of sulphamic acid, or a salt thereof.

If $R^3$ is a sulphamate group then the compound of the present invention is referred to as a sulphamate compound.

Typically, the sulphamate group has the formula:

$$(R^4)(R^5)N—S(O)(O)—O—$$

wherein preferably $R^4$ and $R^5$ are independently selected from H, alkyl, cycloalkyl, alkenyl and aryl, or combinations thereof, or together represent alkylene, wherein the or each alkyl or cycloalkyl or alkenyl or optionally contain one or more hetero atoms or groups.

When substituted, the N-substituted compounds of this invention may contain one or two N-alkyl, N-alkenyl, N-cycloalkyl or N-aryl substituents, preferably containing or each containing a maximum of 10 carbon atoms. When $R^4$ and/or $R^5$ is alkyl, the preferred values are those where $R^4$ and $R^5$ are each independently selected from lower alkyl groups containing from 1 to 6 carbon atoms, that is to say methyl, ethyl, propyl etc. $R^4$ and $R^5$ may both be methyl. When $R^4$ and/or $R^5$ is aryl, typical values are phenyl and tolyl ($PhCH_3$; o). Where $R^4$ and $R^5$ represent cycloalkyl, typical values are cyclopropyl, cyclopentyl, cyclohexyl etc. When joined together $R^4$ and $R^5$ typically represent an alkylene group providing a chain of 4 to 6 carbon atoms, optionally interrupted by one or more hetero atoms or groups, e.g. to provide a 5 membered heterocycle, e.g. morpholino, pyrrolidino or piperidino.

Within the values alkyl, cycloalkyl, alkenyl and aryl substituted groups are included containing as substituents therein one or more groups which do not interfere with the sulphatase inhibitory activity of the compound in question. Exemplary non-interfering substituents include hydroxy, amino, halo, alkoxy, alkyl and aryl.

In some embodiments, the sulphamate group may form a ring structure by being fused to (or associated with) one or more atoms in or on group X.

In some embodiments, there may be more than one sulphamate group. By way of example, there may be two sulphamates (i.e. bis-sulphamate compounds). If these compounds are based on a steroidal nucleus, preferably the second (or at least one of the additional) sulphamate group is located at position 17 of the steroidal nucleus. These groups need not be the same.

In some preferred embodiments, at least one of $R^4$ and $R^5$ is H.

In some further preferred embodiments, each of $R^4$ and $R^5$ is H.

Phosphonate Group

If $R^3$ is a phosphonate group then the compound of the present invention is referred to as a phosphonate compound.

Typically, the phosphonate group has the formula:

$(R^6)—P(O)(OH)—O—$ wherein preferably $R^6$ is H, alkyl, cycloalkyl, alkenyl or aryl, or combinations thereof, wherein the or each alkyl or cycloalkyl or alkenyl or optionally contain one or more hetero atoms or groups.

When substituted, the N-substituted compounds of this invention may contain one or two N-alkyl, N-alkenyl, N-cycloalkyl or N-aryl substituents, preferably containing or each containing a maximum of 10 carbon atoms. When $R^6$ is alkyl, $R^6$ may be a lower alkyl groups containing from 1 to 6 carbon atoms, that is to say methyl, ethyl, propyl etc. By way of example, $R^6$ may be methyl. When $R^6$ is aryl, typical values are phenyl and tolyl ($PhCH_3$; o). Where $R^6$ represents cycloalkyl, typical values are cyclopropyl, cyclopentyl, cyclohexyl etc. $R^6$ may even comprise an alkylene group providing a chain of 4 to 6 carbon atoms, optionally interrupted by one or more hetero atoms or groups, e.g. to provide a 5 membered heterocycle, e.g. morpholino, pyrrolidino or piperidino.

Within the values alkyl, cycloalkyl, alkenyl and aryl substituted groups are included containing as substituents therein one or more groups which do not interfere with the sulphatase inhibitory activity of the compound in question. Exemplary non-interfering substituents include hydroxy, amino, halo, alkoxy, alkyl and aryl.

In some embodiments, the phosphonate group may form a ring structure by being fused to (or associated with) one or more atoms in or on group X.

In some embodiments, there may be more than one phosphonate group. By way of example, there may be two phosphonates (i.e. bis-phosphonate compounds). If these compounds are based on a steroidal nucleus, preferably the second (or at least one of the additional) phosphonate group is located at position 17 of the steroidal nucleus. These groups need not be the same.

Thiophosphonate Group

If $R^3$ is a thiophosphonate group then the compound of the present invention is referred to as a thiophosphonate compound.

Typically, the thiophosphonate group has the formula:

$(R^7)—P(S)(OH)—O—$ wherein preferably $R^7$ is H, alkyl, cycloalkyl, alkenyl or aryl, or combinations thereof, wherein the or each alkyl or cycloalkyl or alkenyl or optionally contain one or more hetero atoms or groups.

When substituted, the N-substituted compounds of this invention may contain one or two N-alkyl, N-alkenyl, N-cycloalkyl or N-aryl substituents, preferably containing or each containing a maximum of 10 carbon atoms. When $R^7$ is alkyl, $R^7$ may be a lower alkyl groups containing from 1 to 6 carbon atoms, that is to say methyl, ethyl, propyl etc. By way of example, $R^7$ may be methyl. When $R^7$ is aryl, typical values are phenyl and tolyl ($PhCH_3$; o). Where $R^7$ represents cycloalkyl, typical values are cyclopropyl, cyclopentyl, cyclohexyl etc. $R^7$ may even comprise an alkylene group providing a chain of 4 to 6 carbon atoms, optionally interrupted by one or more hetero atoms or groups, e.g. to provide a 5 membered heterocycle, e.g. morpholino, pyrrolidino or piperidino.

Within the values alkyl, cycloalkyl, alkenyl and aryl substituted groups are included containing as substituents therein one or more groups which do not interfere with the sulphatase inhibitory activity of the compound in question. Exemplary non-interfering substituents include hydroxy, amino, halo, alkoxy, alkyl and aryl.

In some embodiments, the thiophosphonate group may form a ring structure by being fused to (or associated with) one or more atoms in or on group X.

In some embodiments, there may be more than one thiophosphonate group. By way of example, there may be two thiophosphonates (i.e. bis-thiophosphonate compounds). If these compounds are based on a steroidal nucleus, preferably the second (or at least one of the additional) thiophosphonate group is located at position 17 of the steroidal nucleus. These groups need not be the same.

Sulphonate Group

If $R^3$ is a sulphonate group then the compound of the present invention is referred to as a sulphonate compound.

Typically, the sulphonate group has the formula:

$(R^8)—S(O)(O)—O—$ wherein preferably $R^8$ is H, alkyl, cycloalkyl, alkenyl or aryl, or combinations thereof, wherein the or each alkyl or cycloalkyl or alkenyl or optionally contain one or more hetero atoms or groups.

When substituted, the N-substituted compounds of this invention may contain one or two N-alkyl, N-alkenyl, N-cycloalkyl or N-aryl substituents, preferably containing or each containing a maximum of 10 carbon atoms. When $R^8$ is alkyl, $R^8$ may be a lower alkyl groups containing from 1 to 6 carbon atoms, that is to say methyl, ethyl, propyl etc. By way of example, $R^8$ may be methyl. When $R^8$ is aryl, typical values are phenyl and tolyl ($PhCH_3$; o). Where $R^8$ represents cycloalkyl, typical values are cyclopropyl, cyclopentyl, cyclohexyl etc. $R^8$ may even comprise an alkylene group providing a chain of 4 to 6 carbon atoms, optionally interrupted by one or more hetero atoms or groups, e.g. to provide a 5 membered heterocycle, e.g. morpholino, pyrrolidino or piperidino.

Within the values alkyl, cycloalkyl, alkenyl and aryl substituted groups are included containing as substituents therein one or more groups which do not interfere with the sulphatase inhibitory activity of the compound in question.

Exemplary non-interfering substituents include hydroxy, amino, halo, alkoxy, alkyl and aryl.

In some embodiments, the sulphonate group may form a ring structure by being fused to (or associated with) one or more atoms in or on group X.

In some embodiments, there may be more than one sulphonate group. By way of example, there may be two sulphonates (i.e. bis-sulphonate compounds). If these compounds are based on a steroidal nucleus, preferably the second (or at least one of the additional) sulphonate group is located at position 17 of the steroidal nucleus. These groups need not be the same.

Combination of Sulphonate/Phosphonate/Thiophosphonate/Sulphamate

For some compounds of the present invention there may be present one of a sulphonate as herein defined or a phosphonate as herein defined or a thiophosphonate as herein defined or a sulphamate as herein defined; and another of a sulphonate as herein defined or a phosphonate as herein defined or a thiophosphonate as herein defined or a sulphamate as herein defined. By way of example, the compound of the present invention may comprise one sulphamate group and one phosphonate group.

If these compounds of the present invention are based on a steroidal nucleus, preferably the other of said groups is located at position 17 of the steroidal nucleus.

Mimic

In one aspect, the ring system X or the single ring X in combination with K can be a mimic of a steroidal ring structure.

The term "mimic" as used herein means having a similar or different structure but having a similar functional effect. In other words, group K and ring X together may be a bio-isostere of the rings of a steroid, or an active part thereof.

In a preferred aspect, group K and ring X together may be a bio-isostere of the rings of oestrone, or a part thereof.

Steroidal Ring Structure

In one preferred aspect, the ring system X or the single ring X in combination with K make up a steroidal ring structure—that is to say a cyclopentanophenanthrene skeleton, or bio-isosteres thereof.

As it is well known in the art, a classical steroidal ring structure has the generic formula of:

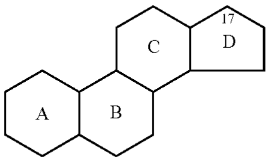

In the above formula, the rings have been labelled in the conventional manner.

An example of a bio-isostere is when any one or more of rings A, B, C and D is a heterocyclic ring and/or when any one or more of rings A, B, C and D has been substituted and/or when any one or more of rings A, B, C and D has been modified; but wherein the bio-isostere in the absence of the sulphamate group has steroidal properties.

In this regard, the structure of a preferred polycyclic structure can be presented as:

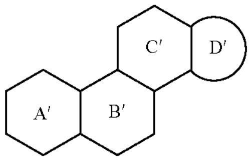

wherein each ring A', B', C' and D' independently represents a heterocyclic ring or a non-heterocyclic ring, which rings may be independently substituted or unsubstituted, saturated or unsaturated.

By way of example, any one or more of rings A', B', C' and D' may be independently substituted with suitable groups—such as an alkyl group, an aryl group, a hydroxy group, a halo group, a hydrocarbyl group, an oxyhydrocarbyl group etc.

An example of D' is a five or six membered non-heterocyclic ring having at least one substituent.

In one preferred embodiment, the ring D' is substituted with a ethinyl group.

If any one of rings A', B', C' and D' is a heterocyclic ring, then preferably that heterocyclic ring comprises a combination of C atoms and at least one N atom and/or at least one O atom. Other heterocyclic atoms may be present in the ring.

Examples of suitable, preferred steroidal nuclei rings A'–D' of the compounds of the present invention include rings A–D of dehydroepiandrosterone and oestrogens including oestrone.

Preferred steroidal nuclei rings A'–D' of the compounds of the present invention include rings A–D of:

Oestrones and Substituted Oestrones, Viz:
oestrone
2-OH-oestrone
4-OH-oestrone
6α-OH-oestrone
7α-OH-oestrone
16α-OH-oestrone
16β-OH-oestrone
2-MeO-oestrone
17-deoxyoestrone Oestradiols and Substituted Oestradiols, Viz:
4-OH-17β-oestradiol
6α-OH-17β-oestradiol
7α-OH-17β-oestradiol
4-OH-17α-oestradiol
6α-OH-17α-oestradiol
7α-OH-17α-oestradiol
16α-OH-17α-oestradiol
16α-OH-17β-oestradiol
16β-OH-17α-oestradiol
16β-OH-17β-oestradiol
17α-oestradiol
17β-oestradiol
17α-ethinyl-17β-oestradiol
17β-ethinyl-17α-oestradiol
17-deoxyoestradiol Oestriols and Substituted Oestriols, Viz:
oestriol
4-OH-oestriol
6α-OH-oestriol 7α-OH-oestriol
17-deoxyoestriol Dehydroepiandrosterones and Substituted Dehydroepiandrosterones, Viz:
dehydroepiandrosterones
6α-OH-dehydroepiandrosterone
7α-OH-dehydroepiandrosterone
16α-OH-dehydroepiandrosterone
16β-OH-dehydroepiandrosterone
androstenediol In general terms the ring system A'B'C'D' may contain a variety of non-interfering substituents. In particular, the ring system A'B'C'D' may contain one or more hydroxy, alkyl especially lower ($C_1$–$C_6$) alkyl, e.g. methyl, ethyl, n-propyl, isopropyl, n-butyl, sec-butyl, tert-butyl, n-pentyl and other pentyl isomers, and n-hexyl and other hexyl isomers, alkoxy especially lower ($C_1$–$C_6$) alkoxy, e.g. methoxy, ethoxy, propoxy etc., alkinyl, e.g. ethinyl, or halogen, e.g. fluoro substituents.

Non-Steroid Structures

In an alternative embodiment, the compound of the present invention may not contain or be based on a steroid nucleus. In this regard, the polycyclic compound may contain or be based on a non-steroidal ring system—such as diethylstilboestrol, stilboestrol, coumarins, flavonoids, combrestatin and other ring systems. Other suitable non-steroidal compounds for use in or as the composition of the present invention may be found in U.S. Pat. No. 5,567,831.

Other Substituents

The compound of the present invention may have substituents other than $R^1$ and $R^2$. By way of example, these other substituents may be one or more of: one or more sulphamate group(s), one or more phosphonate group(s), one or more thiophosphonate group(s), one or more sulphonate group(s), one or more sulphonamide group(s), one or more halo groups, one or more O groups, one or more hydroxy groups, one or more amino groups, one or more sulphur containing group(s), one or more hydrocarbyl group(s)—such as an oxyhydrocarbyl group.

Oxyhydrocarbyl

The term "oxyhydrocarbyl" group as used herein means a group comprising at least C, H and O and may optionally comprise one or more other suitable substituents. Examples of such substituents may include halo-, alkoxy-, nitro-, an alkyl group, a cyclic group etc. In addition to the possibility of the substituents being a cyclic group, a combination of substituents may form a cyclic group. If the oxyhydrocarbyl group comprises more than one C then those carbons need not necessarily be linked to each other. For example, at least two of the carbons may be linked via a suitable element or group. Thus, the oxyhydrocarbyl group may contain hetero atoms. Suitable hetero atoms will be apparent to those skilled in the art and include, for instance, sulphur and nitrogen.

In one embodiment of the present invention, the oxyhydrocarbyl group is a oxyhydrocarbon group.

Here the term "oxyhydrocarbon" means any one of an alkoxy group, an oxyalkenyl group, an oxyalkynyl group, which groups may be linear, branched or cyclic, or an oxyaryl group. The term oxyhydrocarbon also includes those groups but wherein they have been optionally substituted. If the oxyhydrocarbon is a branched structure having substituent(s) thereon, then the substitution may be on either the hydrocarbon backbone or on the branch; alternatively the substitutions may be on the hydrocarbon backbone and on the branch.

Typically, the oxyhydrocarbyl group is of the formula $C_{1-6}O$ (such as a $C_{1-3}O$).

Assay for Determining STS Activity Using Cancer Cells (Protocol 1)

Inhibition of Steroid Sulphatase Activity in MCF-7 Cells

Steroid sulphatase activity is measured in vitro using intact MCF-7 human breast cancer cells. This hormone dependent cell line is widely used to study the control of human breast cancer cell growth. It possesses significant steroid sulphatase activity (MacIndoe et al. Endocrinology, 123, 1281–1287 (1988); Purohit & Reed, Int. J. Cancer, 50, 901–905 (1992)) and is available in the U.S.A. from the American Type Culture Collection (ATCC) and in the U.K. (e.g. from The Imperial Cancer Research Fund).

Cells are maintained in Minimal Essential Medium (MEM) (Flow Laboratories, Irvine, Scotland) containing 20 mM HEPES, 5% foetal bovine serum, 2 mM glutamine, non-essential amino acids and 0.075% sodium bicarbonate. Up to 30 replicate 25 cm2 tissue culture flasks are seeded with approximately $1\times10^5$ cells/flask using the above medium. Cells are grown to 80% confluency and the medium is changed every third day.

Intact monolayers of MCF-7 cells in triplicate 25 $cm^2$ tissue culture flasks are washed with Earle's Balanced Salt Solution (EBSS from ICN Flow, High Wycombe, U.K.) and incubated for 3–4 hours at 37° C. with 5 pmol ($7\times10^5$ dpm) [6,7-3H]oestrone-3-sulphate (specific activity 60 Ci/mmol from New England Nuclear, Boston, Mass., U.S.A.) in serum-free MEM (2.5 ml) together with oestrone-3-sulphamate (11 concentrations: 0; 1 fM; 0.01 pM; 0.1 pM; 1 pM; 0.01 nM; 0.1 nM; 1 nM; 0.01 mM; 0.1 mM; 1 mM). After incubation each flask is cooled and the medium (1 ml) is pipetted into separate tubes containing [14C]oestrone (7×103 dpm) (specific activity 97 Ci/mmol from Amersham International Radiochemical Centre, Amersham, U.K.). The mixture is shaken thoroughly for 30 seconds with toluene (5 ml). Experiments have shown that >90% [14C] oestrone and <0.1% [3H]oestrone-3-sulphate is removed from the aqueous phase by this treatment. A portion (2 ml) of the organic phase is removed, evaporated and the 3H and 14C content of the residue determined by scintillation spectrometry. The mass of oestrone-3-sulphate hydrolysed was calculated from the 3H counts obtained (corrected for the volumes of the medium and organic phase used, and for recovery of [14C] oestrone added) and the specific activity of the substrate. Each batch of experiments includes incubations of microsomes prepared from a sulphatase-positive human placenta (positive control) and flasks without cells (to assess apparent non-enzymatic hydrolysis of the substrate). The number of cell nuclei per flask is determined using a Coulter Counter after treating the cell monolayers with Zaponin. One flask in each batch is used to assess cell membrane status and viability using the Trypan Blue exclusion method (Phillips, H. J. (1973) In: Tissue culture and applications, [eds: Kruse, D. F. & Patterson, M. K.]; pp. 406–408; Academic Press, New York).

Results for steroid sulphatase activity are expressed as the mean±1 S.D. of the total product (oestrone+oestradiol) formed during the incubation period (20 hours) calculated for 106 cells and, for values showing statistical significance, as a percentage reduction (inhibition) over incubations containing no oestrone-3-sulphamate. Unpaired Student's t-test was used to test the statistical significance of results.

Assay for Determining STS Activity Using Placental Microsomes (Protocol 2)

Inhibition of Steroid Sulphatase Activity in Placental Microsomes

Sulphatase-positive human placenta from normal term pregnancies are thoroughly minced with scissors and washed once with cold phosphate buffer (pH 7.4, 50 mM) then re-suspended in cold phosphate buffer (5 ml/g tissue). Homogenisation is accomplished with an Ultra-Turrax homogeniser, using three 10 second bursts separated by 2 minute cooling periods in ice. Nuclei and cell debris are removed by centrifuging (4° C.) at 2000 g for 30 minutes and portions (2 ml) of the supernatant are stored at 20° C. The protein concentration of the supernatants is determined by the method of Bradford (Anal. Biochem., 72, 248–254 (1976)).

Incubations (1 ml) are carried out using a protein concentration of 100 mg/ml, substrate concentration of 20 mM [6,7-3H]oestrone-3-sulphate (specific activity 60 Ci/mmol from New England Nuclear, Boston, Mass., U.S.A.) and an incubation time of 20 minutes at 37° C. If necessary eight concentrations of compounds are employed: 0 (i.e. control); 0.05 mM; 0.1 mM; 0.2 mM; 0.4 mM; 0.6 mM; 0.8 mM; 1.0 mM. After incubation each sample is cooled and the medium (1 ml) was pipetted into separate tubes containing [14C] oestrone (7×103 dpm) (specific activity 97 Ci/mmol from Amersham International Radiochemical Centre, Amersham, U.K.). The mixture is shaken thoroughly for 30 seconds with toluene (5 ml). Experiments have shown that >90% [14C] oestrone and <0.1% [3H]oestrone-3-sulphate is removed from the aqueous phase by this treatment. A portion (2 ml) of the organic phase was removed, evaporated and the 3H and 14C content of the residue determined by scintillation spectrometry. The mass of oestrone-3-sulphate hydrolysed is calculated from the 3H counts obtained (corrected for the volumes of the medium and organic phase used, and for recovery of [14C]oestrone added) and the specific activity of the substrate.

Animal Assay Model for Determining STS Activity (Protocol 3)

Inhibition of Oestrone Sulphatase Activity In Vivo

The compounds of the present invention may be studied using an animal model, in particular in ovariectomised rats. In this model compounds which are oestrogenic stimulate uterine growth.

The compound (0.1 mg/Kg/day for five days) is administered orally to rats with another group of animals receiving vehicle only (propylene glycol). At the end of the study samples of liver tissue were obtained and oestrone sulphatase activity assayed using 3H oestrone sulphate as the substrate as previously described (see PCT/GB95/02638).

Animal Assay Model for Determining Oestrogenic Activity (Protocol 4)

Lack of In Vivo Oestrogenicity

The compounds of the present invention may be studied using an animal model, in particular in ovariectomised rats. In this model, compounds which are oestrogenic stimulate uterine growth.

The compound (0.1 mg/Kg/day for five days) was administered orally to rats with another group of animals receiving vehicle only (propylene glycol). At the end of the study uteri were obtained and weighed with the results being expressed as uterine weight/whole body weight×100.

Compounds having no significant effect on uterine growth are not oestrogenic.

Biotechnological Assays for Determining STS Activity (Protocol 5)

The ability of compounds to inhibit oestrone sulphatase activity can also be assessed using amino acid sequences or nucleotide sequences encoding STS, or active fragments, derivatives, homologues or variants thereof in, for example, high-through put screens.

Any one or more of appropriate targets—such as an amino acid sequence and/or nucleotide sequence—may be used for identifying an agent capable of modulating STS in any of a variety of drug screening techniques. The target employed in such a test may be free in solution, affixed to a solid support, borne on a cell surface, or located intracellularly. The abolition of target activity or the formation of binding complexes between the target and the agent being tested may be measured.

The assay of the present invention may be a screen, whereby a number of agents are tested. In one aspect, the assay method of the present invention is a high through put screen.

Techniques for drug screening may be based on the method described in Geysen, European Patent Application 84/03564, published on Sep. 13, 1984. In summary, large numbers of different small peptide test compounds are synthesised on a solid substrate, such as plastic pins or some other surface. The peptide test compounds are reacted with a suitable target or fragment thereof and washed. Bound entities are then detected—such as by appropriately adapting methods well known in the art. A purified target can also be coated directly onto plates for use in a drug screening techniques. Alternatively, non-neutralising antibodies can be used to capture the peptide and immobilise it on a solid support.

This invention also contemplates the use of competitive drug screening assays in which neutralising antibodies capable of binding a target specifically compete with a test compound for binding to a target.

Another technique for screening provides for high throughput screening (HTS) of agents having suitable binding affinity to the substances and is based upon the method described in detail in WO 84/03564.

It is expected that the assay methods of the present invention will be suitable for both small and large-scale screening of test compounds as well as in quantitative assays.

In one preferred aspect, the present invention relates to a method of identifying agents that selectively modulate STS, which compounds have the formula (Ia).

Reporters

A wide variety of reporters may be used in the assay methods (as well as screens) of the present invention with preferred reporters providing conveniently detectable signals (e.g. by spectroscopy). By way of example, a reporter gene may encode an enzyme which catalyses a reaction which alters light absorption properties.

Other protocols include enzyme-linked immunosorbent assay (ELISA), radioimmunoassay (RIA) and fluorescent activated cell sorting (FACS). A two-site, monoclonal-based immunoassay utilising monoclonal antibodies reactive to two non-interfering epitopes may even be used. These and other assays are described, among other places, in Hampton R et al (1990, Serological Methods, A Laboratory Manual, APS Press, St Paul Minn.) and Maddox D E et al (1983, J Exp Med 15 8:121 1).

Examples of reporter molecules include but are not limited to (β-galactosidase, invertase, green fluorescent protein, luciferase, chloramphenicol, acetyltransferase, (-glucuronidase, exo-glucanase and glucoamylase. Alternatively, radiolabelled or fluorescent tag-labelled nucleotides can be incorporated into nascent transcripts which are then identified when bound to oligonucleotide probes.

By way of further examples, a number of companies such as Pharmacia Biotech (Piscataway, N.J.), Promega (Madison, Wis.), and US Biochemical Corp (Cleveland, Ohio) supply commercial kits and protocols for assay procedures. Suitable reporter molecules or labels include those radionuclides, enzymes, fluorescent, chemiluminescent, or chromogenic agents as well as substrates, cofactors, inhibitors, magnetic particles and the like. Patents teaching the use of such labels include U.S. Pat. No. 3,817,837; U.S. Pat. No. 3,850,752; U.S. Pat. No. 3,939,350; U.S. Pat. No. 3,996,345; U.S. Pat. No. 4,277,437; U.S. Pat. No. 4,275,149 and U.S. Pat. No. 4,366,241.

Host Cells

The term "host cell"—in relation to the present invention includes any cell that could comprise the target for the agent of the present invention.

Thus, a further embodiment of the present invention provides host cells transformed or transfected with a polynucleotide that is or expresses the target of the present invention. Preferably said polynucleotide is carried in a vector for the replication and expression of polynucleotides that are to be the target or are to express the target. The cells will be chosen to be compatible with the said vector and may for example be prokaryotic (for example bacterial), fungal, yeast or plant cells.

The gram negative bacterium *E. coli* is widely used as a host for heterologous gene expression. However, large amounts of heterologous protein tend to accumulate inside the cell. Subsequent purification of the desired protein from the bulk of *E. coli* intracellular proteins can sometimes be difficult.

In contrast to *E. coli*, bacteria from the genus Bacillus are very suitable as heterologous hosts because of their capability to secrete proteins into the culture medium. Other bacteria suitable as hosts are those from the genera *Streptomyces* and *Pseudomonas*.

Depending on the nature of the polynucleotide encoding the polypeptide of the present invention, and/or the desirability for further processing of the expressed protein, eukaryotic hosts such as yeasts or other fungi may be preferred. In general, yeast cells are preferred over fungal cells because they are easier to manipulate. However, some proteins are either poorly secreted from the yeast cell, or in some cases are not processed properly (e.g. hyperglycosylation in yeast). In these instances, a different fungal host organism should be selected.

Examples of suitable expression hosts within the scope of the present invention are fungi such as *Aspergillus* species (such as those described in EP-A-0184438 and EP-A-0284603) and *Trichoderma* species; bacteria such as *Bacillus* species (such as those described in EP-A-0134048 and EP-A-0253455), *Streptomyces* species and *Pseudomonas* species; and yeasts such as *Kluyveromyces* species (such as those described in EP-A-0096430 and EP-A-0301670) and *Saccharomyces* species. By way of example, typical expression hosts may be selected from *Aspergillus niger, Aspergillus niger* var. *tubigenis, Aspergillus niger* var. *awamori, Aspergillus aculeatis, Aspergillus nidulans, Aspergillus orvzae, Trichoderma reesei, Bacillus subtilis, Bacillus licheniformis, Bacillus amyloliquefaciens, Kluyveromyces lactis* and *Saccharomyces cerevisiae.*

The use of suitable host cells—such as yeast, fungal and plant host cells—may provide for post-translational modifications (e.g. myristoylation, glycosylation, truncation, lapidation and tyrosine, serine or threonine phosphorylation) as may be needed to confer optimal biological activity on recombinant expression products of the present invention.

Organism

The term "organism" in relation to the present invention includes any organism that could comprise the target according to the present invention and/or products obtained therefrom. Examples of organisms may include a fungus, yeast or a plant.

The term "transgenic organism" in relation to the present invention includes any organism that comprises the target according to the present invention and/or products obtained.

Transformation of Host Cells/Host Organisms

As indicated earlier, the host organism can be a prokaryotic or a eukaryotic organism. Examples of suitable prokaryotic hosts include *E. coli* and *Bacillus subtilis*. Teachings on the transformation of prokaryotic hosts is well documented in the art, for example see Sambrook et al (Molecular Cloning: A Laboratory Manual, 2nd edition, 1989, Cold Spring Harbor Laboratory Press) and Ausubel et al., Current Protocols in Molecular Biology (1995), John Wiley & Sons, Inc.

If a prokaryotic host is used then the nucleotide sequence may need to be suitably modified before transformation—such as by removal of introns.

In another embodiment the transgenic organism can be a yeast. In this regard, yeast have also been widely used as a vehicle for heterologous gene expression. The species *Saccharomyces cerevisiae* has a long history of industrial use, including its use for heterologous gene expression. Expression of heterologous genes in *Saccharomyces cerevisiae* has been reviewed by Goodey et al (1987, Yeast Biotechnology, D R Berry et al, eds, pp 401–429, Allen and Unwin, London) and by King et al (1989, Molecular and Cell Biology of Yeasts, E F Walton and G T Yarronton, eds, pp 107–133, Blackie, Glasgow).

For several reasons *Saccharomyces cerevisiae* is well suited for heterologous gene expression. First, it is non-pathogenic to humans and it is incapable of producing certain endotoxins. Second, it has a long history of safe use following centuries of commercial exploitation for various purposes. This has led to wide public acceptability. Third, the extensive commercial use and research devoted to the organism has resulted in a wealth of knowledge about the genetics and physiology as well as large-scale fermentation characteristics of *Saccharomyces cerevisiae.*

A review of the principles of heterologous gene expression in *Saccharomyces cerevisiae* and secretion of gene products is given by E Hinchcliffe E Kenny (1993, "Yeast as a vehicle for the expression of heterologous genes", Yeasts, Vol 5, Anthony H Rose and J Stuart Harrison, eds, 2nd edition, Academic Press Ltd.).

Several types of yeast vectors are available, including integrative vectors, which require recombination with the host genome for their maintenance, and autonomously replicating plasmid vectors.

In order to prepare the transgenic Saccharomyces, expression constructs are prepared by inserting the nucleotide sequence into a construct designed for expression in yeast. Several types of constructs used for heterologous expression have been developed. The constructs contain a promoter active in yeast fused to the nucleotide sequence, usually a promoter of yeast origin, such as the GAL1 promoter, is used. Usually a signal sequence of yeast origin, such as the sequence encoding the SUC2 signal peptide, is used. A terminator active in yeast ends the expression system.

For the transformation of yeast several transformation protocols have been developed. For example, a transgenic Saccharomyces according to the present invention can be prepared by following the teachings of Hinnen et al (1978, Proceedings of the National Academy of Sciences of the USA 75, 1929); Beggs, J D (1978, Nature, London, 275, 104); and Ito, H et al (1983, J Bacteriology 153, 163–168).

The transformed yeast cells are selected using various selective markers. Among the markers used for transformation are a number of auxotrophic markers such as LEU2, HIS4 and TRP1, and dominant antibiotic resistance markers such as aminoglycoside antibiotic markers, e.g. G418.

Another host organism is a plant. The basic principle in the construction of genetically modified plants is to insert genetic information in the plant genome so as to obtain a stable maintenance of the inserted genetic material. Several techniques exist for inserting the genetic information, the two main principles being direct introduction of the genetic information and introduction of the genetic information by use of a vector system. A review of the general techniques may be found in articles by Potrykus (Annu Rev Plant Physiol Plant Mol Biol [1991] 42:205–225) and Christou (Agro-Food-Industry Hi-Tech March/April 1994 17–27). Further teachings on plant transformation may be found in EP-A-0449375.

Thus, the present invention also provides a method of transforming a host cell with a nucleotide sequence that is to be the target or is to express the target. Host cells transformed with the nucleotide sequence may be cultured under conditions suitable for the expression of the encoded protein. The protein produced by a recombinant cell may be displayed on the surface of the cell. If desired, and as will be understood by those of skill in the art, expression vectors containing coding sequences can be designed with signal sequences which direct secretion of the coding sequences through a particular prokaryotic or eukaryotic cell membrane. Other recombinant constructions may join the coding sequence to nucleotide sequence encoding a polypeptide domain which will facilitate purification of soluble proteins (Kroll D J et al (1993) DNA Cell Biol 12:441–53).

Variants/Homologues/Derivatives

In addition to the specific amino acid sequences and nucleotide sequences mentioned herein, the present invention also encompasses the use of variants, homologue and derivatives thereof. Here, the term "homology" can be equated with "identity".

In the present context, an homologous sequence is taken to include an amino acid sequence which may be at least 75, 85 or 90% identical, preferably at least 95 or 98% identical. Although homology can also be considered in terms of similarity (i.e. amino acid residues having similar chemical properties/functions), in the context of the present invention it is preferred to express homology in terms of sequence identity.

Homology comparisons can be conducted by eye, or more usually, with the aid of readily available sequence comparison programs. These commercially available computer programs can calculate % homology between two or more sequences.

% homology may be calculated over contiguous sequences, i.e. one sequence is aligned with the other sequence and each amino acid in one sequence is directly compared with the corresponding amino acid in the other sequence, one residue at a time. This is called an "ungapped" alignment. Typically, such ungapped alignments are performed only over a relatively short number of residues.

Although this is a very simple and consistent method, it fails to take into consideration that, for example, in an otherwise identical pair of sequences, one insertion or deletion will cause the following amino acid residues to be put out of alignment, thus potentially resulting in a large reduction in % homology when a global alignment is performed. Consequently, most sequence comparison methods are designed to produce optimal alignments that take into consideration possible insertions and deletions without penalising unduly the overall homology score. This is achieved by inserting "gaps" in the sequence alignment to try to maximise local homology.

However, these more complex methods assign "gap penalties" to each gap that occurs in the alignment so that, for the same number of identical amino acids, a sequence alignment with as few gaps as possible—reflecting higher relatedness between the two compared sequences—will achieve a higher score than one with many gaps. "Affine gap costs" are typically used that charge a relatively high cost for the existence of a gap and a smaller penalty for each subsequent residue in the gap. This is the most commonly used gap scoring system. High gap penalties will of course produce optimised alignments with fewer gaps. Most alignment programs allow the gap penalties to be modified. However, it is preferred to use the default values when using such software for sequence comparisons. For example when using the GCG Wisconsin Bestfit package (see below) the default gap penalty for amino acid sequences is −12 for a gap and −4 for each extension.

Calculation of maximum % homology therefore firstly requires the production of an optimal alignment, taking into consideration gap penalties. A suitable computer program for carrying out such an alignment is the GCG Wisconsin Bestfit package (University of Wisconsin, U.S.A.; Devereux et al., 1984, Nucleic Acids Research 12:387). Examples of other software than can perform sequence comparisons include, but are not limited to, the BLAST package (see Ausubel et al., 1999 ibid—Chapter 18), FASTA (Atschul et al., 1990, J. Mol. Biol., 403–410) and the GENEWORKS suite of comparison tools. Both BLAST and FASTA are available for offline and online searching (see Ausubel et al., 1999 ibid, pages 7–58 to 7–60). However it is preferred to use the GCG Bestfit program.

A further useful reference is that found in FEMS Microbiol Lett 1999 May 15; 174(2):247–50 (and a published erratum appears in FEMS Microbiol Lett 1999 Aug. 1; 177(1):187–8).

Although the final % homology can be measured in terms of identity, the alignment process itself is typically not based on an all-or-nothing pair comparison. Instead, a scaled similarity score matrix is generally used that assigns scores to each pairwise comparison based on chemical similarity or evolutionary distance. An example of such a matrix commonly used is the BLOSUM62 matrix—the default matrix for the BLAST suite of programs. GCG Wisconsin programs generally use either the public default values or a custom symbol comparison table if supplied (see user manual for further details). It is preferred to use the public default values for the GCG package, or in the case of other software, the default matrix, such as BLOSUM62.

Once the software has produced an optimal alignment, it is possible to calculate % homology, preferably % sequence identity. The software typically does this as part of the sequence comparison and generates a numerical result.

The sequences may also have deletions, insertions or substitutions of amino acid residues which produce a silent change and result in a functionally equivalent substance. Deliberate amino acid substitutions may be made on the basis of similarity in polarity, charge, solubility, hydrophobicity, hydrophilicity, and/or the amphipathic nature of the residues as long as the secondary binding activity of the substance is retained. For example, negatively charged amino acids include aspartic acid and glutamic acid; positively charged amino acids include lysine and arginine; and amino acids with uncharged polar head groups having similar hydrophilicity values include leucine, isoleucine, valine, glycine, alanine, asparagine, glutamine, serine, threonine, phenylalanine, and tyrosine.

Conservative substitutions may be made, for example according to the Table below.

Amino acids in the same block in the second column and preferably in the same line in the third column may be substituted for each other:

| | | |
|---|---|---|
| ALIPHATIC | Non-polar | G A P |
| | | I L V |
| | Polar - uncharged | C S T M |
| | | NQ |
| | Polar - charged | D E |
| | | K R |
| AROMATIC | | H F W Y |

Expression Vectors

The nucleotide sequence for use as the target or for expressing the target can be incorporated into a recombinant replicable vector. The vector may be used to replicate and express the nucleotide sequence in and/or from a compatible host cell. Expression may be controlled using control sequences which include promoters/enhancers and other expression regulation signals. Prokaryotic promoters and promoters functional in eukaryotic cells may be used. Tissue specific or stimuli specific promoters may be used. Chimeric promoters may also be used comprising sequence elements from two or more different promoters described above.

The protein produced by a host recombinant cell by expression of the nucleotide sequence may be secreted or may be contained intracellularly depending on the sequence and/or the vector used. The coding sequences can be designed with signal sequences which direct secretion of the substance coding sequences through a particular prokaryotic or eukaryotic cell membrane.

Fusion Proteins

The target amino acid sequence may be produced as a fusion protein, for example to aid in extraction and purification. Examples of fusion protein partners include glutathione-S-transferase (GST), 6×His, GAL4 (DNA binding and/or transcriptional activation domains) and (-galactosidase. It may also be convenient to include a proteolytic cleavage site between the fusion protein partner and the protein sequence of interest to allow removal of fusion protein sequences. Preferably the fusion protein will not hinder the activity of the target.

The fusion protein may comprise an antigen or an antigenic determinant fused to the substance of the present invention. In this embodiment, the fusion protein may be a non-naturally occurring fusion protein comprising a substance which may act as an adjuvant in the sense of providing a generalised stimulation of the immune system. The antigen or antigenic determinant may be attached to either the amino or carboxy terminus of the substance.

In another embodiment of the invention, the amino acid sequence may be ligated to a heterologous sequence to encode a fusion protein. For example, for screening of peptide libraries for agents capable of affecting the substance activity, it may be useful to encode a chimeric substance expressing a heterologous epitope that is recognised by a commercially available antibody.

Therapy

The compounds of the present invention may be used as therapeutic agents—i.e. in therapy applications.

The term "therapy" includes curative effects, alleviation effects, and prophylactic effects.

The therapy may be on humans or animals, preferably female animals.

Pharmaceutical Compositions

In one aspect, the present invention provides a pharmaceutical composition, which comprises a compound according to the present invention and optionally a pharmaceutically acceptable carrier, diluent or excipient (including combinations thereof).

The pharmaceutical compositions may be for human or animal usage in human and veterinary medicine and will typically comprise any one or more of a pharmaceutically acceptable diluent, carrier, or excipient. Acceptable carriers or diluents for therapeutic use are well known in the pharmaceutical art, and are described, for example, in Remington's Pharmaceutical Sciences, Mack Publishing Co. (A. R. Gennaro edit. 1985). The choice of pharmaceutical carrier, excipient or diluent can be selected with regard to the intended route of administration and standard pharmaceutical practice. The pharmaceutical compositions may comprise as—or in addition to—the carrier, excipient or diluent any suitable binder(s), lubricant(s), suspending agent(s), coating agent(s), solubilising agent(s).

Preservatives, stabilisers, dyes and even flavouring agents may be provided in the pharmaceutical composition. Examples of preservatives include sodium benzoate, sorbic acid and esters of p-hydroxybenzoic acid. Antioxidants and suspending agents may be also used.

There may be different composition/formulation requirements dependent on the different delivery systems. By way of example, the pharmaceutical composition of the present invention may be formulated to be delivered using a minipump or by a mucosal route, for example, as a nasal spray or aerosol for inhalation or ingestable solution, or parenterally in which the composition is formulated by an injectable form, for delivery, by, for example, an intravenous, intramuscular or subcutaneous route. Alternatively, the formulation may be designed to be delivered by both routes.

Where the agent is to be delivered mucosally through the gastrointestinal mucosa, it should be able to remain stable during transit though the gastrointestinal tract; for example, it should be resistant to proteolytic degradation, stable at acid pH and resistant to the detergent effects of bile.

Where appropriate, the pharmaceutical compositions can be administered by inhalation, in the form of a suppository or pessary, topically in the form of a lotion, solution, cream, ointment or dusting powder, by use of a skin patch, orally in the form of tablets containing excipients such as starch or lactose, or in capsules or ovules either alone or in admixture with excipients, or in the form of elixirs, solutions or suspensions containing flavouring or colouring agents, or they can be injected parenterally, for example intravenously, intramuscularly or subcutaneously. For parenteral administration, the compositions may be best used in the form of a sterile aqueous solution which may contain other substances, for example enough salts or monosaccharides to make the solution isotonic with blood. For buccal or sublingual administration the compositions may be administered in the form of tablets or lozenges which can be formulated in a conventional manner.

Combination Pharmaceutical

The compound of the present invention may be used in combination with one or more other active agents, such as one or more other pharmaceutically active agents.

By way of example, the compounds of the present invention may be used in combination with other STS inhibitors and/or other inhibitors such as an aromatase inhibitor (such as for example, 4hydroxyandrostenedione (4-OHA)) and/or steroids—such as the naturally occurring sterneurosteroids dehydroepiandrosterone sulfate (DHEAS) and pregnenolone sulfate (PS) and/or other structurally similar organic compounds. Examples of other STS inhibitors may be found in the above references. By way of example, STS inhibitors for use in the present invention include EMATE, and either or both of the 2-ethyl and 2-methoxy 17-deoxy compounds.

In addition, or in the alternative, the compound of the present invention may be used in combination with a biological response modifier.

The term biological response modifier ("BRM") includes cytokines, immune modulators, growth factors, haematopoiesis regulating factors, colony stimulating factors, chemotactic, haemolytic and thrombolytic factors, cell surface receptors, ligands, leukocyte adhesion molecules, monoclonal antibodies, preventative and therapeutic vaccines, hormones, extracellular matrix components, fibronectin, etc. For some applications, preferably, the biological response modifier is a cytokine. Examples of cytokines include: interleukins (IL)—such as IL-1, IL-2, IL-3, IL-4, IL-5, IL-6, IL-7, IL-8, IL-9, IL-10, IL-11, IL-12, IL-19; Tumour Necrosis Factor (TNF)—such as TNF-α; Interferon alpha, beta and gamma; TGF-β. For some applications, preferably the cytokine is tumour necrosis factor (TNF). For some applications, the TNF may be any type of TNF—such as TNF-α, TNF-β, including derivatives or mixtures thereof. More preferably the cytokine is TNF-α. Teachings on TNF may be found in the art—such as WO-A-98/08870 and WO-A-98/13348.

Administration

Typically, a physician will determine the actual dosage which will be most suitable for an individual subject and it will vary with the age, weight and response of the particular patient. The dosages below are exemplary of the average case. There can, of course, be individual instances where higher or lower dosage ranges are merited.

The compositions of the present invention may be administered by direct injection. The composition may be formulated for parenteral, mucosal, intramuscular, intravenous, subcutaneous, intraocular or transdermal administration. Depending upon the need, the agent may be administered at a dose of from 0.01 to 30 mg/kg body weight, such as from 0.1 to 10 mg/kg, more preferably from 0.1 to 1 mg/kg body weight.

By way of further example, the agents of the present invention may be administered in accordance with a regimen of 1 to 4 times per day, preferably once or twice per day. The specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Aside from the typical modes of delivery—indicated above—the term "administered" also includes delivery by techniques such as lipid mediated transfection, liposomes, immunoliposomes, lipofectin, cationic facial amphiphiles (CFAs) and combinations thereof. The routes for such delivery mechanisms include but are not limited to mucosal, nasal, oral, parenteral, gastrointestinal, topical, or sublingual routes.

The term "administered" includes but is not limited to delivery by a mucosal route, for example, as a nasal spray or aerosol for inhalation or as an ingestable solution; a parenteral route where delivery is by an injectable form, such as, for example, an intravenous, intramuscular or subcutaneous route.

Thus, for pharmaceutical administration, the STS inhibitors of the present invention can be formulated in any suitable manner utilising conventional pharmaceutical formulating techniques and pharmaceutical carriers, adjuvants, excipients, diluents etc. and usually for parenteral administration. Approximate effective dose rates may be in the range from 1 to 1000 mg/day, such as from 10 to 900 mg/day or even from 100 to 800 mg/day depending on the individual activities of the compounds in question and for a patient of average (70 Kg) bodyweight. More usual dosage rates for the preferred and more active compounds will be in the range 200 to 800 mg/day, more preferably, 200 to 500 mg/day, most preferably from 200 to 250 mg/day. They may be given in single dose regimes, split dose regimes and/or in multiple dose regimes lasting over several days. For oral administration they may be formulated in tablets, capsules, solution or suspension containing from 100 to 500 mg of compound per unit dose. Alternatively and preferably the compounds will be formulated for parenteral administration in a suitable parenterally administrable carrier and providing single daily dosage rates in the range 200 to 800 mg, preferably 200 to 500, more preferably 200 to 250 mg. Such effective daily doses will, however, vary depending on inherent activity of the active ingredient and on the bodyweight of the patient, such variations being within the skill and judgement of the physician.

Cell Cycling

The compounds of the present invention may be useful in the method of treatment of a cell cycling disorder.

As discussed in "Molecular Cell Biology" 3rd Ed. Lodish et al. pages 177–181 different eukaryotic cells can grow and divide at quite different rates. Yeast cells, for example, can divide every 120 min., and the first divisions of fertilised eggs in the embryonic cells of sea urchins and insects take only 1530 min. because one large pre-existing cell is subdivided. However, most growing plant and animal cells take 10–20 hours to double in number, and some duplicate at a much slower rate. Many cells in adults, such as nerve cells and striated muscle cells, do not divide at all; others, like the fibroblasts that assist in healing wounds, grow on demand but are otherwise quiescent.

Still, every eukaryotic cell that divides must be ready to donate equal genetic material to two daughter cells. DNA synthesis in eukaryotes does not occur throughout the cell division cycle but is restricted to a part of it before cell division.

The relationship between eukaryotic DNA synthesis and cell division has been thoroughly analysed in cultures of mammalian cells that were all capable of growth and division. In contrast to bacteria, it was found, eukaryotic cells spend only a part of their time in DNA synthesis, and it is completed hours before cell division (mitosis). Thus a gap of time occurs after DNA synthesis and before cell division; another gap was found to occur after division and before the next round of DNA synthesis. This analysis led to the conclusion that the eukaryotic cell cycle consists of an M (mitotic) phase, a $G_1$ phase (the first gap), the S (DNA synthesis) phase, a $G_2$ phase (the second gap), and back to M. The phases between mitoses ($G_1$, S, and $G_2$) are known collectively as the interphase.

Many nondividing cells in tissues (for example, all quiescent fibroblasts) suspend the cycle after mitosis and just prior to DNA synthesis; such "resting" cells are said to have exited from the cell cycle and to be in the $G_0$ state.

It is possible to identify cells when they are in one of the three interphase stages of the cell cycle, by using a fluorescence-activated cell sorter (FACS) to measure their relative DNA content: a cell that is in $G_1$ (before DNA synthesis) has a defined amount x of DNA; during S (DNA replication), it has between x and 2x; and when in $G_2$ (or M), it has 2x of DNA.

The stages of mitosis and cytokinesis in an animal cell are as follows (a) Interphase. The $G_2$ stage of interphase immediately precedes the beginning of mitosis. Chromosomal DNA has been replicated and bound to protein during the S phase, but chromosomes are not yet seen as distinct structures. The nucleolus is the only nuclear substructure that is visible under light microscope. In a diploid cell before DNA replication there are two morphologic chromosomes of each type, and the cell is said to be 2n. In $G_2$, after DNA replication, the cell is 4n. There are four copies of each chromosomal DNA. Since the sister chromosomes have not yet separated from each other, they are called sister chromatids.

b) Early prophase. Centrioles, each with a newly formed daughter centriole, begin moving toward opposite poles of the cell; the chromosomes can be seen as long threads. The nuclear membrane begins to disaggregate into small vesicles.

(c) Middle and late prophase. Chromosome condensation is completed; each visible chromosome structure is composed of two chromatids held together at their centromeres. Each chromatid contains one of the two newly replicated daughter DNA molecules. The microtubular spindle begins to radiate from the regions just adjacent to the centrioles, which are moving closer to their poles. Some spindle fibres reach from pole to pole; most go to chromatids and attach at kinetochores.

(d) Metaphase. The chromosomes move toward the equator of the cell, where they become aligned in the equatorial plane. The sister chromatids have not yet separated.

(e) Anaphase. The two sister chromatids separate into independent chromosomes. Each contains a centromere that is linked by a spindle fibre to one pole, to which it moves. Thus one copy of each chromosome is donated to each daughter cell. Simultaneously, the cell elongates, as do the pole-to-pole spindles. Cytokinesis begins as the cleavage furrow starts to form.

(f) Telophase. New membranes form around the daughter nuclei; the chromosomes uncoil and become less distinct, the nucleolus becomes visible again, and the nuclear membrane forms around each daughter nucleus. Cytokinesis is nearly complete, and the spindle disappears as the microtubules and other fibres depolymerise. Throughout mitosis the "daughter" centriole at each pole grows until it is full-length. At telophase the duplication of each of the original centrioles is completed, and new daughter centrioles will be generated during the next interphase.

(g) Interphase. Upon the completion of cytokinesis, the cell enters the $G_1$ phase of the cell cycle and proceeds again around the cycle.

It will be appreciated that cell cycling is an extremely important cell process. Deviations from normal cell cycling can result in a number of medical disorders. Increased and/or unrestricted cell cycling may result in cancer. Reduced cell cycling may result in degenerative conditions. Use of the compound of the present invention may provide a means to treat such disorders and conditions.

Thus, the compound of the present invention may be suitable for use in the treatment of cell cycling disorders such as cancers, including hormone dependent and hormone independent cancers.

In addition, the compound of the present invention may be suitable for the treatment of cancers such as breast cancer, ovarian cancer, endometrial cancer, sarcomas, melanomas, prostate cancer, pancreatic cancer etc. and other solid tumours.

For some applications, cell cycling is inhibited and/or prevented and/or arrested, preferably wherein cell cycling is prevented and/or arrested. In one aspect cell cycling may be inhibited and/or prevented and/or arrested in the $G_2$/M phase. In one aspect cell cycling may be irreversibly prevented and/or inhibited and/or arrested, preferably wherein cell cycling is irreversibly prevented and/or arrested.

By the term "irreversibly prevented and/or inhibited and/or arrested" it is meant after application of a compound of the present invention, on removal of the compound the effects of the compound, namely prevention and/or inhibition and/or arrest of cell cycling, are still observable. More particularly by the term "irreversibly prevented and/or inhibited and/or arrested" it is meant that when assayed in accordance with the cell cycling assay protocol presented herein, cells treated with a compound of interest show less growth after Stage 2 of the protocol I than control cells. Details on this protocol are presented below.

Thus, the present invention provides compounds which: cause inhibition of growth of oestrogen receptor positive (ER+) and ER negative (ER−) breast cancer cells in vitro by preventing and/or inhibiting and/or arresting cell cycling; and/or cause regression of nitroso-methyl urea (NMU)-induced mammary tumours in intact animals (i.e. not ovariectomised), and/or prevent and/or inhibit and/or arrest cell cycling in cancer cells; and/or act in vivo by preventing and/or inhibiting and/or arresting cell cycling and/or act as a cell cycling agonist.

Cell Cycling Assay (Protocol 6)

Procedure

Stage 1

MCF-7 breast cancer cells are seeded into multi-well culture plates at a density of 105 cells/well. Cells were allowed to attach and grown until about 30% confluent when they are treated as follows:

Control—no treatment

Compound of Interest (COI) 20 μM

Cells are grown for 6 days in growth medium containing the COI with changes of medium/COI every 3 days. At the end of this period cell numbers were counted using a Coulter cell counter.

Stage 2

After treatment of cells for a 6-day period with the COI cells are re-seeded at a density of $10^4$ cells/well. No further treatments are added. Cells are allowed to continue to grow for a further 6 days in the presence of growth medium. At the end of this period cell numbers are again counted.

Cancer

As indicated, the compounds of the present invention may be useful in the treatment of a cell cycling disorder. A particular cell cycling disorder is cancer.

Cancer remains a major cause of mortality in most Western countries. Cancer therapies developed so far have included blocking the action or synthesis of hormones to inhibit the growth of hormone-dependent tumours. However, more aggressive chemotherapy is currently employed for the treatment of hormone-independent tumours.

Hence, the development of a pharmaceutical for anti-cancer treatment of hormone dependent and/or hormone independent tumours, yet lacking some or all of the side-effects associated with chemotherapy, would represent a major therapeutic advance.

It is known that oestrogens undergo a number of hydroxylation and conjugation reactions after their synthesis. Until recently it was thought that such reactions were part of a metabolic process that ultimately rendered oestrogens water soluble and enhanced their elimination from the body. It is now evident that some hydroxy metabolites (e.g. 2-hydroxy and 16alpha-hydroxy) and conjugates (e.g. oestrone sulphate, E1S) are important in determining some of the complex actions that oestrogens have in the body.

Workers have investigated the formation of 2- and 16-hydroxylated oestrogens in relation to conditions that alter the risk of breast cancer. There is now evidence that factors which increase 2-hydroxylase activity are associated with a reduced cancer risk, while those increasing 16alpha-hydroxylation may enhance the risk of breast cancer. Further interest in the biological role of oestrogen metabolites has been stimulated by the growing body of evidence that 2-methoxyoestradiol is an endogenous metabolite with anti-mitotic properties. 2-MeOE2 is formed from 2-hydroxy oestradiol (2-OHE2) by catechol oestrogen methyl transferase, an enzyme that is widely distributed throughout the body.

Workers have shown that in vivo 2-MeOE2 inhibits the growth of tumours arising from the subcutaneous injection of Meth A sarcoma, B16 melanoma or MDA-MB-435 oestrogen receptor negative (ER−) breast cancer cells. It also inhibits endothelial cell proliferation and migration, and in vitro angiogenesis. It was suggested that the ability of 2-MeOE2 to inhibit tumour growth in vivo may be due to its ability to inhibit tumour-induced angiogenesis rather than direct inhibition of the proliferation of tumour cells.

The mechanism by which 2-MeOE2 exerts its potent anti-mitogenic and anti-angiogenic effects is still being elucidated. There is evidence that at high concentrations it can inhibit microtubule polymerisation and act as a weak inhibitor of colchicine binding to tubulin. Recently, however, at concentrations that block mitosis, tubulin filaments in cells were not found to be depolymerised but to have an identical morphology to that seen after taxol treatment. It is possible, therefore, that like taxol, a drug that is used for breast and ovarian breast cancer therapy, 2-MeOE2 acts by stabilising microtubule dynamics.

While the identification of 2-MeOE2 as a new therapy for cancer represents an important advance, the bioavailability of orally administered oestrogens is poor. Furthermore, they can undergo extensive metabolism during their first pass through the liver. As part of a research programme to develop a steroid sulphatase inhibitor for breast cancer therapy, oestrone-3-O-sulphamate (EMATE) was identified as a potent active site-directed inhibitor. Unexpectedly, EMATE proved to possess potent oestrogenic properties with its oral uterotrophic activity in rats being a 100-times higher than that of oestradiol. Its enhanced oestrogenicity is thought to result from its absorption by red blood cells (rbcs) which protects it from inactivation during its passage through the liver and which act as a reservoir for its slow release for a prolonged period of time. A number of A-ring modified analogues were synthesised and tested, including 2-methoxyoestrone-3-O-sulphamate. While this compound was equipotent with EMATE as a steroid sulphatase inhibitor, it was devoid of oestrogenicity.

We believe that the compound of the present invention provides a means for the treatment of cancers and, especially, breast cancer.

In addition or in the alternative the compound of the present invention may be useful in the blocking the growth of cancers including leukaemias and solid tumours such as breast, endometrium, prostate, ovary and pancreatic tumours.

Therapy Concerning Oestrogen

We believe that some of the compounds of the present invention may be useful in the control of oestrogen, levels in the body—in particular in females. Thus, some of the compounds may be useful as providing a means of fertility control—such as an oral contraceptive tablet, pill, solution or lozenge. Alternatively, the compound could be in the form of an implant or as a patch.

Thus, the compounds of the present invention may be useful in treating hormonal conditions associated with oestrogen.

In addition or in the alternative the compound of the present invention may be useful in treating hormonal conditions in addition to those associated with oestrogen. Hence, the compound of the present invention may also be capable of affecting hormonal activity and may also be capable of affecting an immune response.

Neurodegenerative Diseases

We believe that some of the compounds of the present invention may be useful in the treatment of neurodenerative diseases, and similar conditions.

By way of example, it is believed that STS inhibitors may be useful in the enhancing the memory function of patients suffering from illnesses such as amnesia, head injuries, Alzheimer's disease, epileptic dementia, presenile dementia, post traumatic dementia, senile dementia, vascular dementia and post-stroke dementia or individuals otherwise seeking memory enhancement.

TH1

We believe that some of the compounds of the present invention may be useful in TH1 implications.

By way of example, it is believed that the presence of STS inhibitors within the macrophage or other antigen presenting cells may lead to a decreased ability of sensitised T cells to mount a TH1 (high IL-2, IFNγ low IL-4) response. The normal regulatory influence of other steroids such as glucocorticoids would therefore predominate.

Inflamatory Conditions

We believe that some of the compounds of the present invention may be useful in treating inflammatory conditions—such as conditions associated with any one or more of: autoimmunity, including for example, rheumatoid arthritis, type I and II diabetes, systemic lupus erythematosus, multiple sclerosis, myasthenia gravis, thyroiditis, vasculitis, ulcerative colitis and Crohn's disease, skin disorders e.g. psoriasis and contact dermatitis; graft versus host disease; eczema; asthma and organ rejection following transplantation.

By way of example, it is believed that STS inhibitors may prevent the normal physiological effect of DHEA or related steroids on immune and/or inflammatory responses.

The compounds of the present invention may be useful in the manufacture of a medicament for revealing an endogenous glucocorticoid-like effect.

Other Therapies

It is also to be understood that the compound/composition of the present invention may have other important medical implications.

For example, the compound or composition of the present invention may be useful in the treatment of the disorders listed in WO-A-99/52890—viz:

In addition, or in the alternative, the compound or composition of the present invention may be useful in the treatment of the disorders listed in WO-A-98/05635. For ease of reference, part of that list is now provided: cancer, inflammation or inflammatory disease, dermatological disorders, fever, cardiovascular effects, haemorrhage, coagulation and acute phase response, cachexia, anorexia, acute infection, HIV infection, shock states, graft–versus-host reactions, autoimmune disease, reperfusion injury, meningitis, migraine and aspirin-dependent anti-thrombosis; tumour growth, invasion and spread, angiogenesis, metastases, malignant, ascites and malignant pleural effusion; cerebral ischaemia, ischaemic heart disease, osteoarthritis, rheumatoid arthritis, osteoporosis, asthma, multiple sclerosis, neurodegeneration, Alzheimer's disease, atherosclerosis, stroke, vasculitis, Crohn's disease and ulcerative colitis; periodontitis, gingivitis; psoriasis, atopic dermatitis, chronic ulcers, epidermolysis bullosa; corneal ulceration, retinopathy and surgical wound healing; rhinitis, allergic conjunctivitis, eczema, anaphylaxis; restenosis, congestive heart failure, endometriosis, atherosclerosis or endosclerosis.

In addition, or in the alternative, the compound or composition of the present invention may be useful in the treatment of disorders listed in WO-A-98/07859. For ease of reference, part of that list is now provided: cytokine and cell proliferation/differentiation activity; immunosuppressant or immunostimulant activity (e.g. for treating immune deficiency, including infection with human immune deficiency virus; regulation of lymphocyte growth; treating cancer and many autoimmune diseases, and to prevent transplant rejection or induce tumour immunity); regulation of haematopoiesis, e.g. treatment of myeloid or lymphoid diseases; promoting growth of bone, cartilage, tendon, ligament and nerve tissue, e.g. for healing wounds, treatment of burns, ulcers and periodontal disease and neurodegeneration; inhibition or activation of follicle-stimulating hormone (modulation of fertility); chemotactic/chemokinetic activity (e.g. for mobilising specific cell types to sites of injury or infection); haemostatic and thrombolytic activity (e.g. for treating haemophilia and stroke); antiinflammatory activity (for treating e.g. septic shock or Crohn's disease); as antimicrobials; modulators of e.g. metabolism or behaviour; as analgesics; treating specific deficiency disorders; in treatment of e.g. psoriasis, in human or veterinary medicine.

In addition, or in the alternative, the composition of the present invention may be useful in the treatment of disorders listed in WO-A-98/09985. For ease of reference, part of that list is now provided: macrophage inhibitory and/or T cell inhibitory activity and thus, anti-inflammatory activity; anti-immune activity, i.e. inhibitory effects against a cellular and/or humoral immune response, including a response not associated with inflammation; inhibit the ability of macrophages and T cells to adhere to extracellular matrix components and fibronectin, as well as up-regulated fas receptor expression in T cells; inhibit unwanted immune reaction and inflammation including arthritis, including rheumatoid arthritis, inflammation associated with hypersensitivity, allergic reactions, asthma, systemic lupus erythematosus, collagen diseases and other autoimmune diseases, inflammation associated with atherosclerosis, arteriosclerosis, atherosclerotic heart disease, reperfusion injury, cardiac arrest, myocardial infarction, vascular inflammatory disorders, respiratory distress syndrome or other cardiopulmonary diseases, inflammation associated with peptic ulcer, ulcerative colitis and other diseases of the gastrointestinal tract, hepatic fibrosis, liver cirrhosis or other hepatic diseases, thyroiditis or other glandular diseases, glomerulonephritis or other renal and urologic diseases, otitis or other oto-rhino-laryngological diseases, dermatitis or other dermal diseases, periodontal diseases or other dental diseases, orchitis or epididimo-orchitis, infertility, orchidal trauma or other immune-related testicular diseases, placental dysfunction, placental insufficiency, habitual abortion, eclampsia, pre-eclampsia and other immune and/or inflammatory-related gynaecological diseases, posterior uveitis, intermediate uveitis, anterior uveitis, conjunctivitis, chorioretinitis, uveoretinitis, optic neuritis, intraocular inflammation, e.g. retinitis or cystoid macular oedema, sympathetic ophthalmia, scleritis, retinitis pigmentosa, immune and inflammatory components of degenerative fondus disease, inflammatory components of ocular trauma, ocular inflammation caused by infection, proliferative vitreo-retinopathies, acute ischaemic optic neuropathy, excessive scarring, e.g. following glaucoma filtration operation, immune and/or inflammation reaction against ocular implants and other immune and inflammatory-related ophthalmic diseases, inflammation associated with autoimmune diseases or conditions or disorders where, both in the central nervous system (CNS) or in any other organ, immune and/or inflammation suppression would be beneficial, Parkinson's disease, complication and/or side effects from treatment of Parkinson's disease, AIDS-related dementia complex HIV-related encephalopathy, Devic's disease, Sydenham chorea, Alzheimer's disease and other degenerative diseases, conditions or disorders of the CNS, inflammatory components of stokes, post-polio syndrome, immune and inflammatory components of psychiatric disorders, myelitis, encephalitis, subacute sclerosing pan-encephalitis, encephalomyelitis, acute neuropathy, subacute neuropathy, chronic neuropathy, Guillaim-Barre syndrome, Sydenham chora, myasthenia gravis, pseudo-tumour cerebri, Down's Syndrome, Huntington's disease, amyotrophic lateral sclerosis, inflammatory components of CNS compression or CNS trauma or infections of the CNS, inflammatory components of muscular atrophies and dystrophies, and immune and inflammatory related diseases, conditions or disorders of the central and peripheral nervous systems, post-traumatic inflammation, septic shock, infectious diseases, inflammatory complications or side effects of surgery, bone marrow transplantation or other transplantation complications and/or side effects, inflammatory and/or immune complications and side effects of gene therapy, e.g. due to infection with a viral carrier, or inflammation associated with AIDS, to suppress or inhibit a humoral and/or cellular immune response, to treat or ameliorate monocyte or leukocyte proliferative diseases, e.g. leukaemia, by reducing the amount of monocytes or lymphocytes, for the prevention and/or treatment of graft rejection in cases of transplantation of natural or artificial cells, tissue and organs such as cornea, bone marrow, organs, lenses, pacemakers, natural or artificial skin tissue.

Other Aspects

In other aspects the present invention provides use of a compound in the manufacture of a medicament for modulating cell cycling and/or modulating apoptosis and/or modulating of cell growth wherein the compound is of the formula

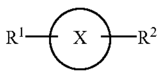

wherein: X is a ring system; $R^1$ is any one of a sulphamate group, a phosphonate group, a thiophosphonate group, a sulphonate group or a sulphonamide group; $R^2$ is any one of a sulphamate group, a phosphonate group, a thiophosphonate group, a sulphonate group or a sulphonamide group;

preferably when X is a steroidal structure and both of $R^1$ and $R^2$ are sulphamate groups, the steroidal ring system (X) represents an oestrogen;

preferably said compound is capable of inhibiting steroid sulphatase (STS) activity and/or is capable of acting as a modulator of cell cycling and/or as a modulator of apoptosis and/or as a modulator of cell growth preferably said medicament inhibits steroid sulphatase (STS)

a method for modulating cell cycling and/or modulating apoptosis and/or modulating of cell growth comprising administering a subject (optionally in need of said treatment) a compound of the formula

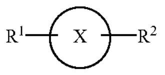

wherein: X is a ring system; $R^1$ is any one of a sulphamate group, a phosphonate group, a thiophosphonate group, a sulphonate group or a sulphonamide group; $R^2$ is any one of a sulphamate group, a phosphonate group, a thiophosphonate group, a sulphonate group or a sulphonamide group;

preferably when X is a steroidal structure and both of $R^1$ and $R^2$ are sulphamate groups, the steroidal ring system (X) represents an oestrogen;

preferably said compound is capable of inhibiting steroid sulphatase (STS) activity and/or is capable of acting as a modulator of cell cycling and/or as a modulator of apoptosis and/or as a modulator of cell growth;

preferably said compound inhibits steroid sulphatase (STS)

a compound of Formula II

Formula II

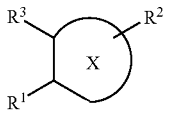

$R^1$ is any one of a sulphamate group, a phosphonate group, a thiophosphonate group, a sulphonate group or a sulphonamide group; $R^2$ is any one of a sulphamate group, a phosphonate group, a thiophosphonate group, a sulphonate group or a sulphonamide group; and $R^3$ is a group other than H preferably wherein said compound is capable of inhibiting steroid sulphatase (STS) activity and/or is capable of acting as a modulator of cell cycling and/or as a modulator of apoptosis and/or as a modulator of cell growth.

preferably $R^3$ is a hydrocarbyl or an oxyhydrocarbyl group, more preferably an oxyhydrocarbyl group, yet more preferably an alkoxy group (each of which terms are as defined herein)

Compound Preparation

The compounds of the present invention may be prepared by reacting an appropriate alcohol with a suitable chloride. By way of example, the sulphamate compounds of the present invention may be prepared by reacting an appropriate alcohol with a suitable sulfamoyl chloride, of the formula $R^4R^5NSO_2Cl$.

Typical conditions for carrying out the reaction are as follows.

Sodium hydride and a sulfamoyl chloride are added to a stirred solution of the alcohol in anhydrous dimethyl formamide at 0° C. Subsequently, the reaction is allowed to warm to room temperature whereupon stirring is continued for a further 24 hours. The reaction mixture is poured onto a cold saturated solution of sodium bicarbonate and the resulting aqueous phase is extracted with dichloromethane. The combined organic extracts are dried over anhydrous $MgSO_4$. Filtration followed by solvent evaporation in vacuo and co-evaporated with toluene affords a crude residue which is further purified by flash chromatography.

Preferably, the alcohol is derivatised, as appropriate, prior to reaction with the sulfamoyl chloride. Where necessary, functional groups in the alcohol may be protected in known manner and the protecting group or groups removed at the end of the reaction.

Preferably, the sulphamate compounds are prepared according to the teachings of Page et al (1990 Tetrahedron 46; 2059–2068).

The phosphonate compounds may be prepared by suitably combining the teachings of Page et al (1990 Tetrahedron 46; 2059–2068) and PCT/GB92/01586.

The sulphonate compounds may be prepared by suitably adapting the teachings of Page et al (1990 Tetrahedron 46; 2059–2068) and PCT/GB92/01586.

The thiophosphonate compounds may be prepared by suitably adapting the teachings of Page et al (1990 Tetrahedron 46; 2059–2068) and PCT/GB91/00270.

Preferred preparations are also presented in the following text.

SUMMARY

In summation, the present invention provides novel compounds for use as steroid sulphatase inhibitors and/or modulators of apoptosis and/or modulators of cell cycling and/or cell growth, and pharmaceutical compositions containing them.

EXAMPLES

The present invention will now be described only by way of example. However, it is to be understood that the examples also present preferred compounds of the present invention, as well as preferred routes for making same and useful intermediates in the preparation of same.

Syntheses

Preparation of 3-O-benzyl-17-□-O-sulfamoyl- and 3-O-benzyl-17-□-O-sulfamoyl-estradiol Starting from oestrone (commercially available, Aldrich), protection of the 3-O— position was done by benzylation to afford BLE99049. Reduction by sodium borohydride gave the 3-O-benzyl-17-□-estradiol BLE99051 in nearly quantitative manner.

Inversion of the configuration of the 17-position of oestradiol was achieved using a Misunobu reaction. The complex formed by triphenylphosphine and DEAD was reacted with the 3-O-benzyl-17-□-estradiol BLE99051 and p-nitrobenzoic acid at 80° C. in toluene to give the 3-O-benzyl-17-□-p-nitrobenzoate-estradiol BLE99053.

Hydrolysis of the ester moiety of BLE99053 using potassium carbonate afforded cleanly the 3-O-benzyl-17-□-estradiol BLE99056 in a 84.5% yield.

Sulfamoylation in the 17-position was carried out using a new method involving 1.2 equivalent of t-BuOK 1 M in THF as base and 5 equivalents of sulfamoyl chloride (0.7 M in toluene) which gave high yields of the sulphamates derivatives BLE99052 and BLE99059.

Bis-alkylation or acylation, hydrogenolysis and final sulphamoylation of the 17-□- and 17-□-estradiol derivatives Bis-alkylation with benzyl chloride of the 17-□ compound BLE99059 led to the bis-alkylated compound BLE99061 in a 47% yield, subsequent benzyl deprotection by hydrogenolysis afforded BLE99066 in a 90.5% yield.

PROTECTION OF ESTRADIOL AND INVERSION OF THE 17β-HYDROXY SUBSTITUENT BY MITSUNOBU REACTION

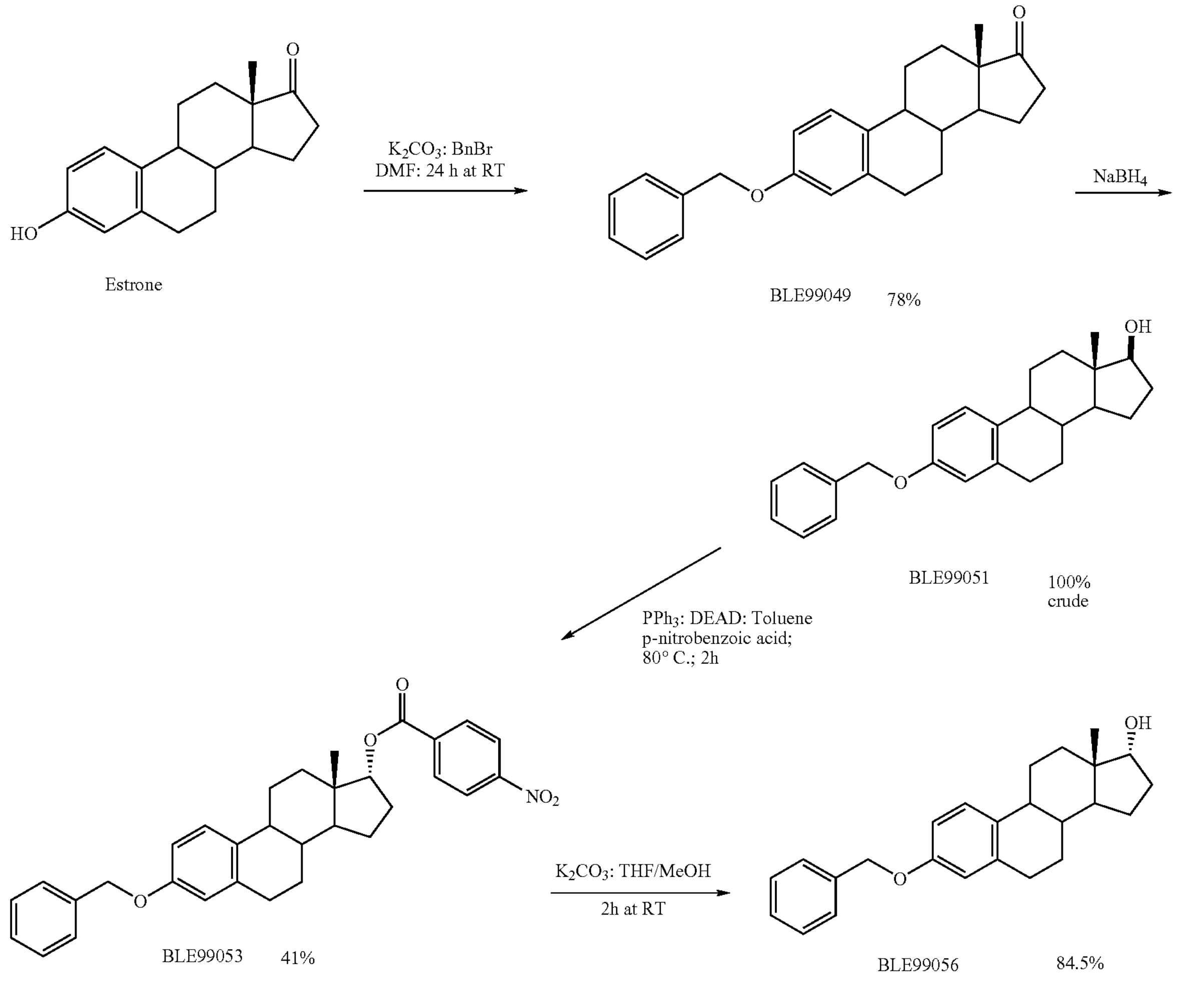

Estrone

BLE99049

BLE99051

BLE99053

BLE99056

17-α-Derivative: N-Alkylation and Deprotection

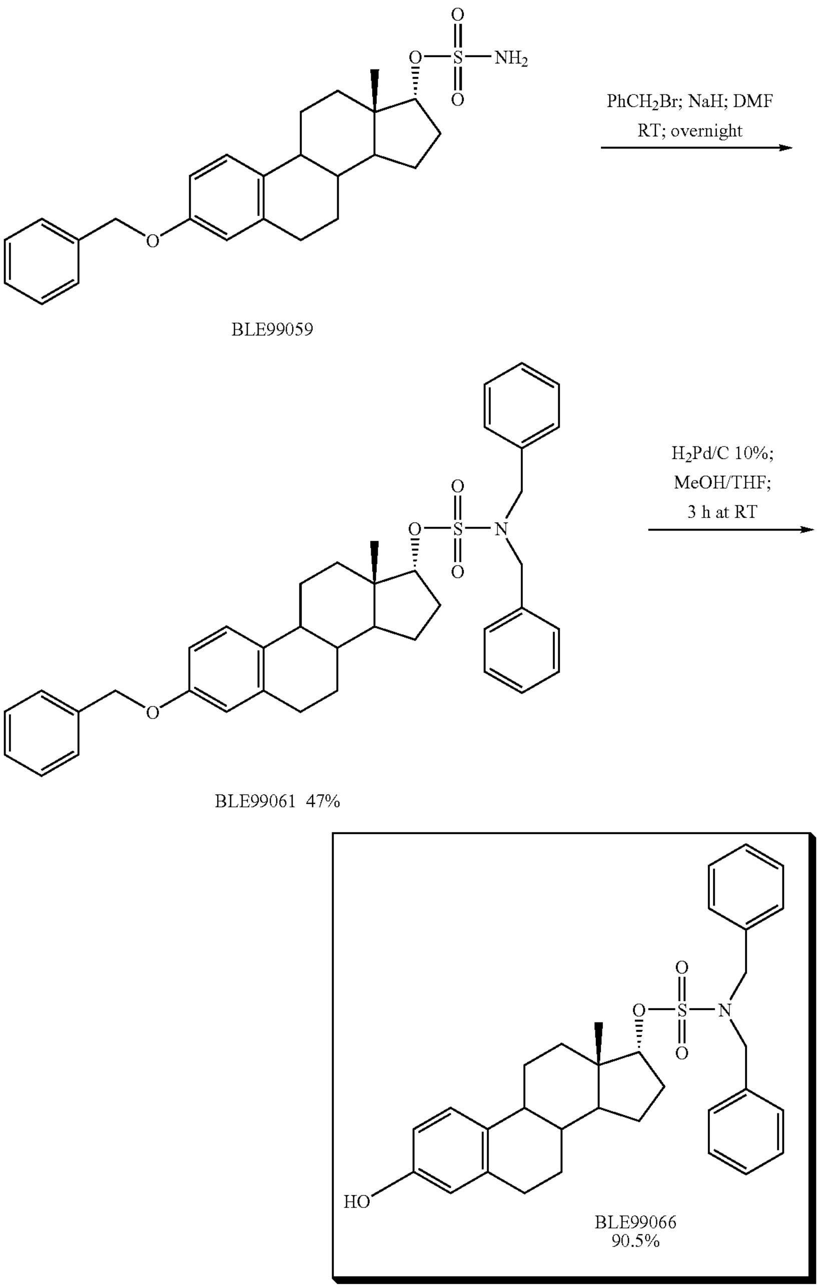

BLE99059

BLE99061 47%

BLE99066
90.5%

Bis-alkylation with benzyl chloride, methyl iodide and acylation with acetyl chloride of the 17-□ derivative BLE99052 gave, respectively, the desired compounds BLE99060, BLE99067 and BLE99058 in good yields. Subsequent benzyl deprotection by hydrogenolysis using $H_2$ Pd/C 10%, respectively, led to 17-sulfamated estradiols BLE99060, BLE99064 and BLE99058.

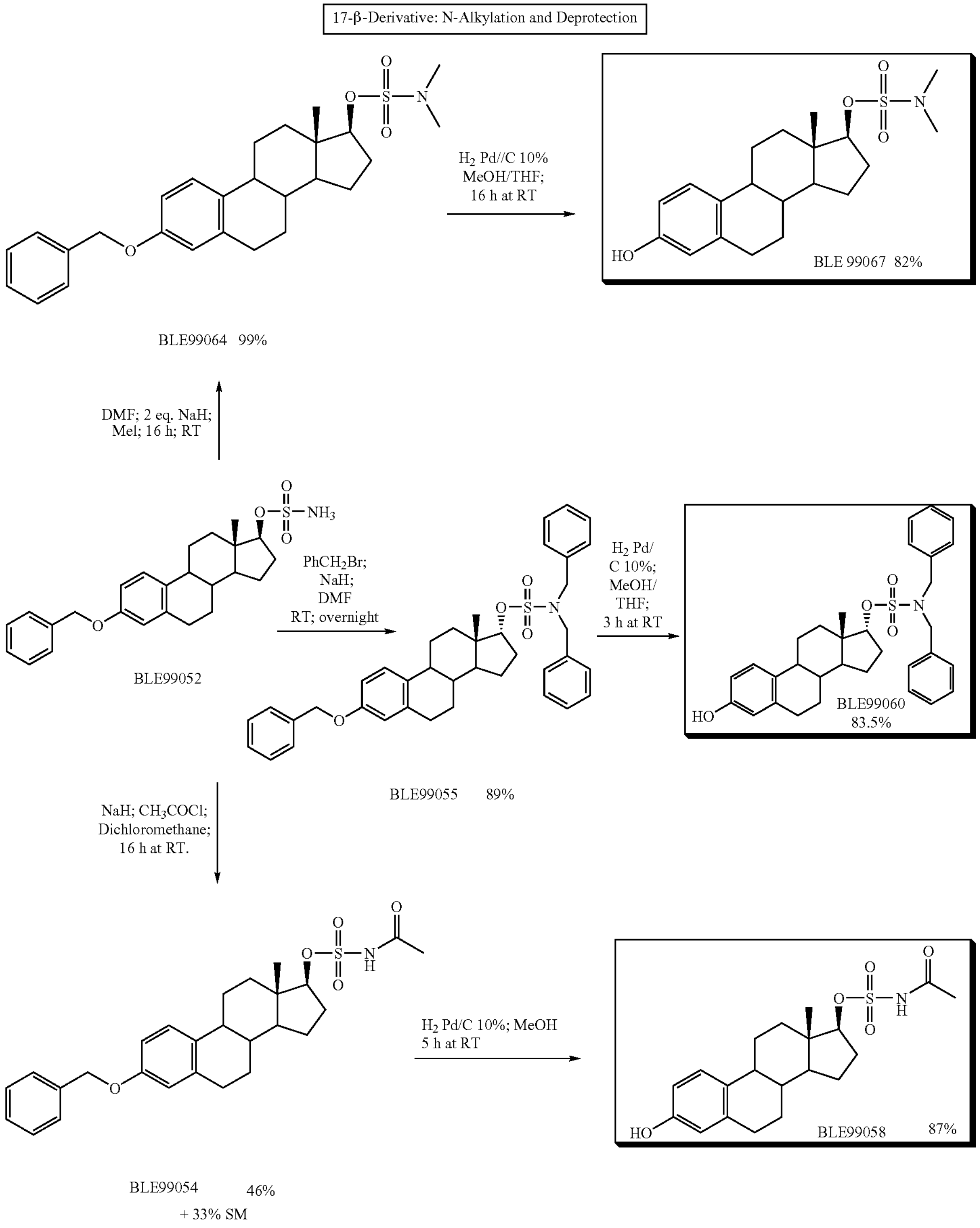
17-β-Derivative: N-Alkylation and Deprotection
H2 Pd//C 10%
MeOH/THF;
16 h at RT
BLE 99067 82%
BLE99064 99%
DMF; 2 eq. NaH;
MeI; 16 h; RT
PhCH2Br;
NaH;
DMF
RT; overnight
BLE99052
H2 Pd/
C 10%;
MeOH/
THF;
3 h at RT
BLE99060
83.5%
BLE99055 89%
NaH; CH3COCl;
Dichloromethane;
16 h at RT.
H2 Pd/C 10%; MeOH
5 h at RT
BLE99058 87%
BLE99054 46%
+ 33% SM Final sulphamoylation in the 3-O-position was done using 3 equivalents of DBMP as base in dichloromethane or dimethylformamide, depending of the solubility of the starting material, and 5 equivalents of sulfamoyl chloride 0.7 M in toluene.
Final 3-O-Sulfamoylation
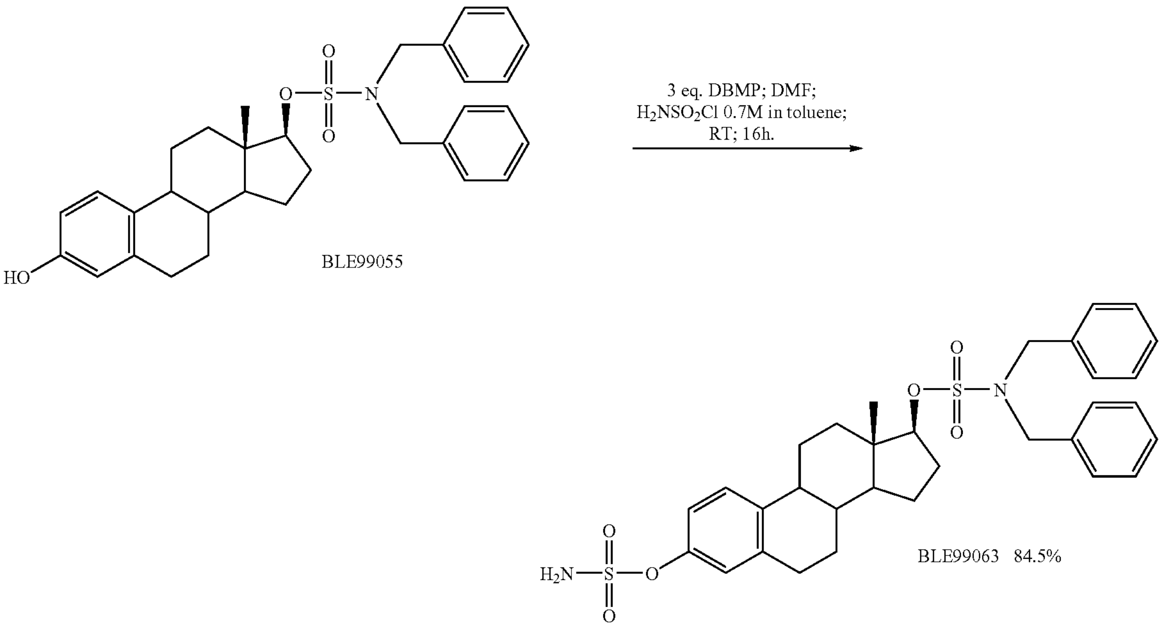
BLE99055
BLE99063 84.5%
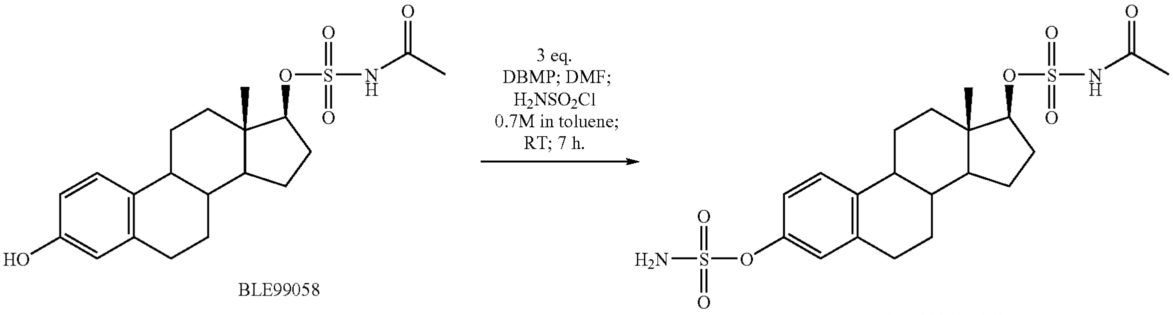
BLE99058
BLE99065 34%
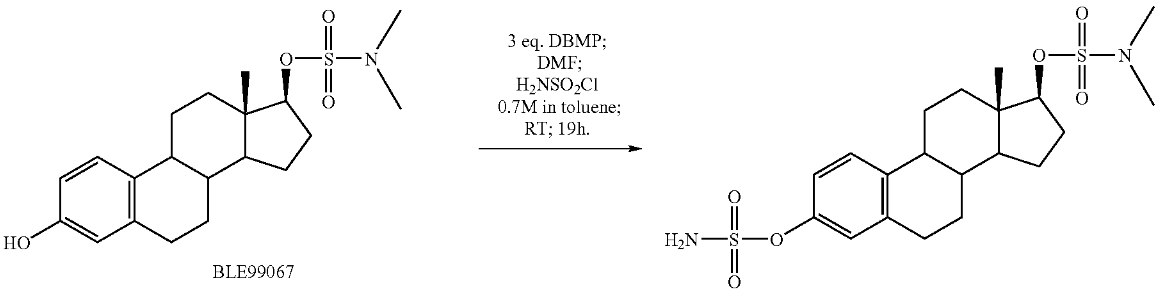
BLE99067
BLE99069 90%

-continued

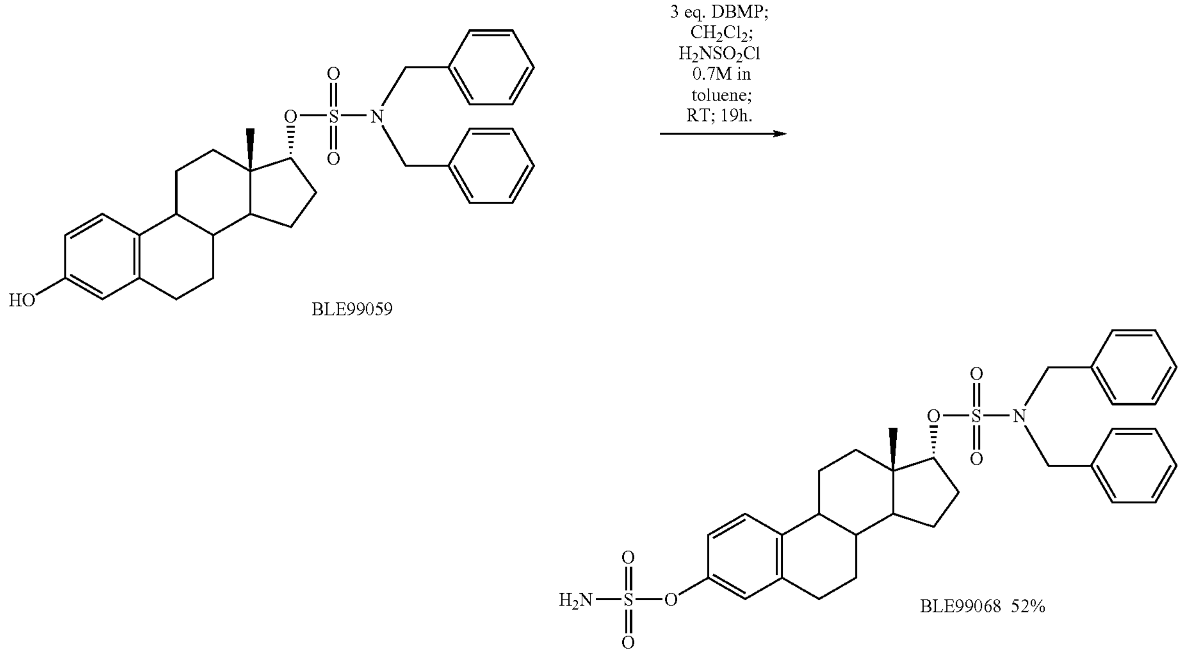

BLE99059

BLE99068 52%

Following the previous strategy (see above), we have prepared the two following compounds:

3-O-Sulfamoyl-estra-1,3,5(10)-trien-17β-O-(N,N-dipentyl) sulfamate BLE00074

3-O-Sulfamoyl-estra-1,3,5(10)-trien-17α-O-(N,N-dipentyl) sulfamate BLE00083A.

3-O-Sulfamoyl-estra-1,3,5(10)-trien-17□-O-(N,N-dipentyl) sulfamate BLE00074

Bis-alkylation with pentyl bromide of the 17-β-O-sulfamate BLE99070 (see preparation in report 2) led to the bis-alkylated compound BLE99072 in a 92.5% yield, subsequent benzyl deprotection by hydrogenolysis afforded BLE99073 in a 80% yield. Final sulfamoylation in the 3-O-position proceeded in 89% yield, using 3 equivalents of DBMP as base in dichloromethane and 5 equivalents of sulfamoyl chloride 0.7 M in toluene, to obtain the bisulfamate derivative BLE00074.

3-O-Sulfamoyl-estra-1,3,5(10)-trien-17 β -O-(N, N-dipentyl)sulfamate BLE00074

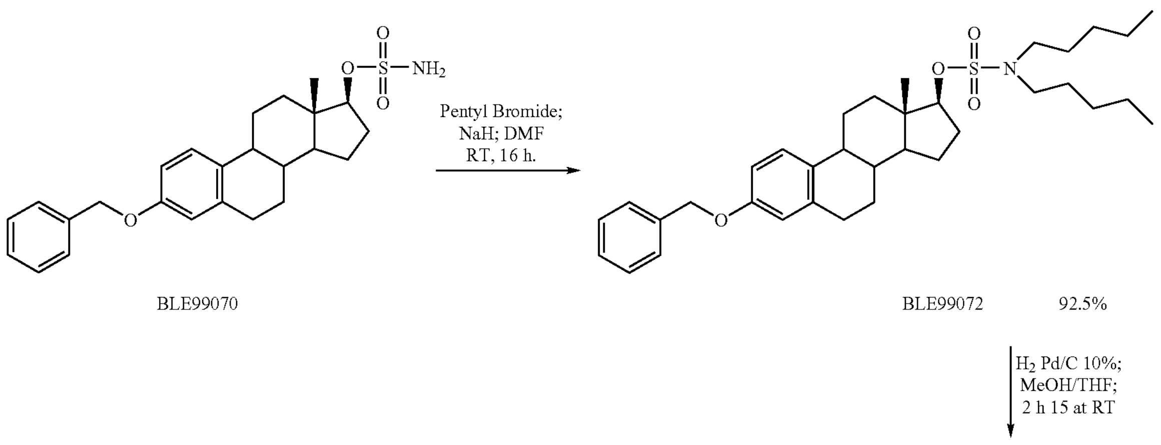

BLE99070

BLE99072 92.5%

-continued

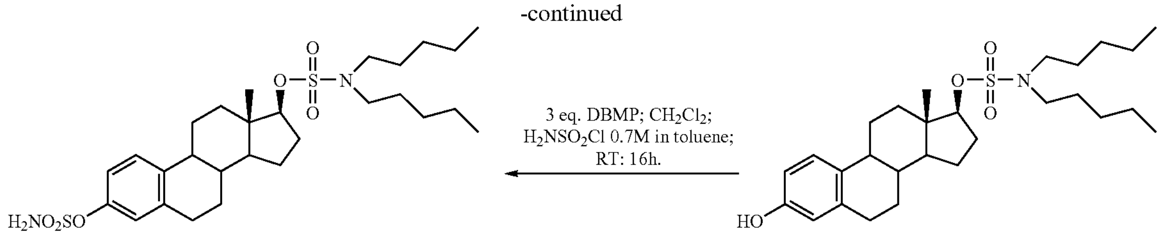

BLE99074 89% BLE99073 80%

3-O-Sulfamoyl-estra-1,3,5(10)-trien-17α-O-(N,N-dipentyl) sulfamate BLE00083B.

The route employed to prepare the bis-sulfamate BLE00083B is the same than for BLE00074. The lower yield of the alkylation of the 17-O-α-sulfamate BLE00077 compare to the 17-O-β-sulfamate BLE00070 stems from the fact that the 17-O-α-sulfamates oestradiol derivatives are not very stable in acidic media or polar solvent ($SiO_2$ or $CDCl_3$ are sometimes acidic enough to promote this degradation). In the final sulfamoylation of compound BLE00082, we isolated after purification by flash chromatography two 3-O-sulfamates: The 17-methyl-gona-1,3,5(10),13(17)-tetraen-3-O-sulfamate BLE00083A and the 3-O-sulfamoyl-estra-1,3,5(10)-trien-17α-O-(N,N-dipentyl) sulfamate BLE00083B.

3-O-Sulfamoyl-estra-1,3,5(10)-trien-17α-O-(N,N-dipentyl)sulfamate BLE00083B

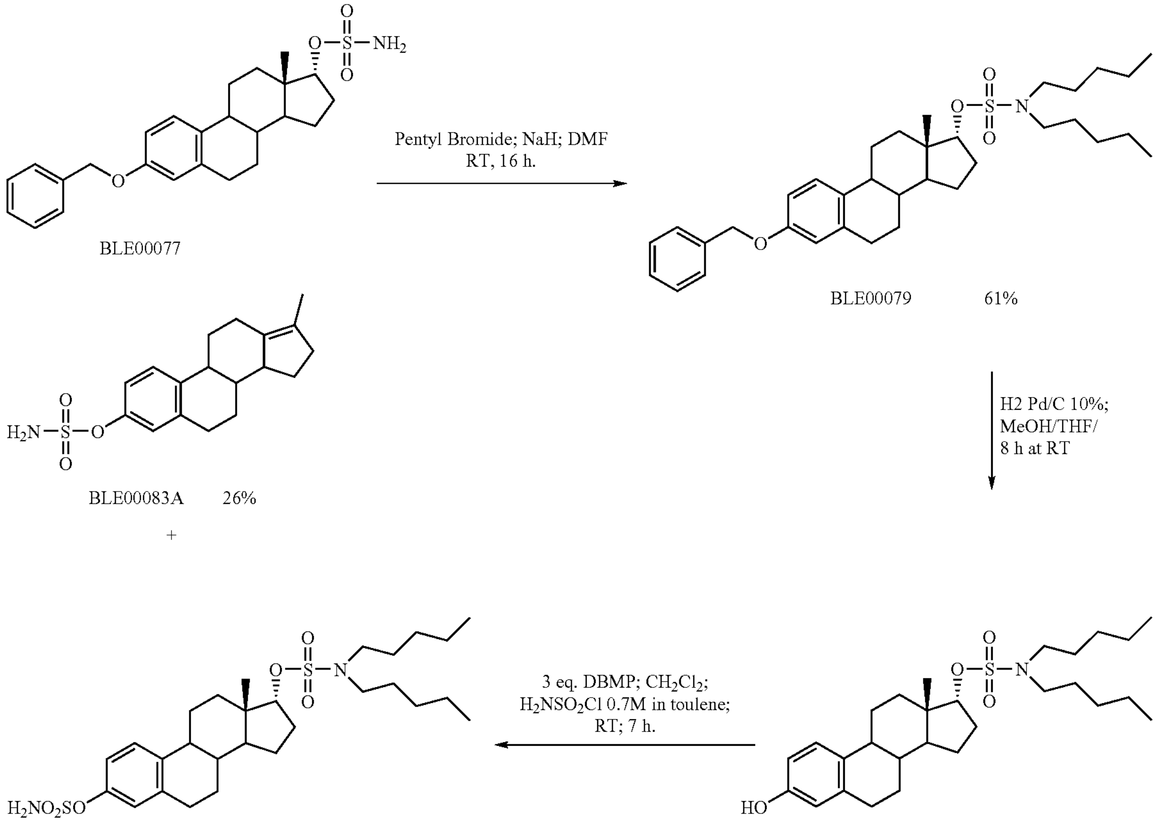

BLE00077

BLE00079 61%

BLE00083A 26%

+

BLE00083B 26%

BLE00082 80%

Experimental

3-Benzyloxyestra-1,3,5(10)-trien-17-one BLE99049

To a solution of oestrone (3.35 g, 12.39 mmol) in DMF (50 ml) were added potassium carbonate (3.45 g, 25 mmol) and benzyl bromide (2.25 ml, 18.75 mmol) at room temperature under an atmosphere of nitrogen. The reaction mixture was stirred for 24 h, then quenched with $H_2O$, and extracted with EtOAc. The combined organic layers were washed with $H_2O$, saturated aqueous NaCl, and then dried ($MgSO_4$). The desiccant was filtered and the solvent was evaporated at reduced pressure. The residue was triturated with $Et_2O$, filtered and evaporated to afford 3.48 g (78% yield) of 3-benzyloxyestra-1,3,5(10)-trien-17-one BLE99049 as a white solid.

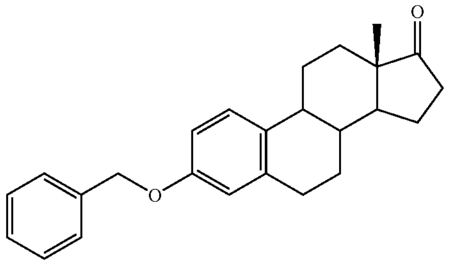

$C_{25}H_{28}O_2$ MW 360.50 Mp 127–130° C. (lit. 126–127° C.) SRI patent WO 99/33858, Tanabe et al. $^1$H NMR 270 MHz ($CDCl_3$): 0.91 (s, 3H, C-18-C$\underline{H}_3$), 1.35–1.75 (m, 6H), 1.85–2.60 (m, 7H), 2.80–3.00 (m, 2H), 5.03 (s, 2H, —$OCH_2$Ph), 6.73 (d, 1H, J=2.7 Hz, C-4-H), 6.79 (dd, 1H, J=2.7 and 8.6 Hz, C-2-H), 7.20 (d, 1H, J=8.6 Hz, C-1-H) and 7.27–7.49 (m, 5H, ArH). M/S m/z (+ve FAB, rel. int.): 360.3 [66, $M^+$], 91.1 (100). HRMS (+ve FAB) m/z calcd for $C_{25}H_{28}O_2$ ($M^+$) 360.20893. found 360.20876 $R_f$ 0.76 (EtOAc;hexane=1:2), SM Rf 0.52

3-Benzyloxyestra-1,3,5(10)-trien-17β-ol BLE99051

To a suspension of 3-benzyloxyestra-1,3,5(10)-trien-17-one BLE99049 (3.46 g, 9.59 mmol) in THF (15 ml) and MeOH (38 ml) was added sodium borohydride (0.36 g, 9.58 mmol) at 0° C. The reaction mixture was stirred for 30 min at room temperature, then quenched with 10 ml of saturated aqueous $NH_4Cl$ and 50 ml of $H_2O$ added. The precipitate was collected by filtration and washed with $H_2O$ to afford 3.50 g of 3-benzyloxyestra-1,3,5(10)-trien-17β-ol BLE99051 (100% crude yield) as a white solid.

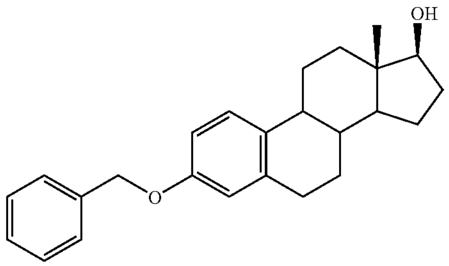

$C_{25}H_{30}O_2$ MW 362.50 Mp 93–95° C. (lit. 118–119° C.) SRI patent WO 99/33858, Tanabe et al. M/S m/z (+ve FAB, rel. int.): 362.2 (81, $M^+$), 345.2 (13), 91.1 (100). HRMS (+ve FAB) m/z calcd for $C_{25}H_{30}O_2$ ($M^+$) 362.22458. found 362.22522 Rf 0.49 (EtOAc:hexane=1:2), SM Rf 0.76

3-Benzyloxyestra-1,3,5(10)-trien-17β-O-sulfamate BLE99052

To a solution of 3-benzyloxyestra-1,3,5(10)-trien-17β-ol BLE99051 (1.20 g, 3.31 mmol) in 35 ml of anhydrous DMF was treated at 0° C. under $N_2$ atmosphere a solution of t-BuOK 1 M in THF (4 ml, 4.00 mmol). The reaction mixture was stirred for 15 min at 0° C., then a solution of sulphamoyl chloride about 0.7 M in toluene (24 ml, 16.32 mmol) was added dropwise at 0° C. The solution was stirred 2 h at room temperature. A saturated solution of $NH_4Cl$ was added at 0° C. (15 ml) then water (60 ml) and the solution was extracted with EtOAc (3×100 ml). The organic layer was washed with brine (3×100 ml), dried over $MgSO_4$, filtered and evaporated to give 1.48 g of a crude yellowish solid. Recrystallisation (2×) in EtOAc/hexane gave 1.29 g (88% yield) of white crystals, the 3-benzyloxyestra-1,3,5(10)-trien-17β-O-sulfamate BLE99052.

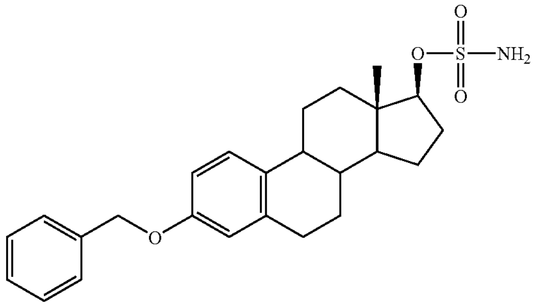

$C_{25}H_{31}NO_4S$ MW 441.58 Mp 108–109° C. $^1$H NMR 400 MHz ($CDCl_3$): 0.87 (s, 3H, C-18-C$\underline{H}_3$), 1.15–2.40 (m, 13H), 2.80–2.90 (m, 2H, C-6-H), 4.51 (t, 1H, J=8.2 Hz, 17□-H), 4.55–4.80 (s br, 2H exch. $D_2O$, —$NH_2$), 5.03 (s, 2H, —$OCH_2$Ph), 6.71 (d, 1H, J=2.3 Hz, C-4-H), 6.78 (dd, 1H, J=2.3 and 8.6 Hz, C-2-H), 7.19 (d, 1H, J=8.6 Hz, C-1-H) and 7.26–7.45 (m, 5H, ArH). M/S m/z (+ve FAB, rel. int.): 441.3 (41, $M^+$), 345.3 (19), 91.1 (100). M/S m/z (−ve FAB, rel. int.): 440.2 [100, $(M-H)^-$]. HRMS (+ve FAB) m/z calcd for $C_{25}H_{31}NO_4S$ ($M^+$) 441.19738. found 441.19769 Rf 0.45 (EtOAc:hexane=1:2), SM Rf 0.48

3-Benzyloxyestra-1,3,5(10)-trien-17α-O-p-nitrobenzoate BLE99053

To a solution of triphenylphosphine (2.10 g, 8.0 mmol) in dry toluene (13.3 ml) was added dropwise at 0–5° C. diethylazodicarboxylate (1.26 ml, 8.0 mmol) and the solution was stirred at 0–5° C. 1 h. A solution of 3-benzyloxyestra-1,3,5(10)-trien-17□-ol BLE99051 (1.45 g, 4.0 mmol) and p-nitrobenzoic acid (2.67 g, 16 mmol) were added at room temperature, then the reaction mixture was stirred for 2 h at 80° C. After the reaction mixture was cooled to room temperature, $H_2O$ was added and the mixture extracted with EtOAc (3×80 ml). The combined organic layers were washed with $H_2O$, saturated aqueous NaCl, and then dried ($MgSO_4$). The desiccant was filtered and the solvent was evaporated at reduced pressure. The residue was purified by column chromatography (column Ø=3 cm, h=23 cm) using as eluent hexane:EtOAc=10:1 to 7:1 gave (after recrystallisation in hexane:EtOAc), 0.85 g of a white/pale pink solid, the 3-benzyloxyestra-1,3,5(10)-trien-17α-O-p-nitrobenzoate BLE99053.

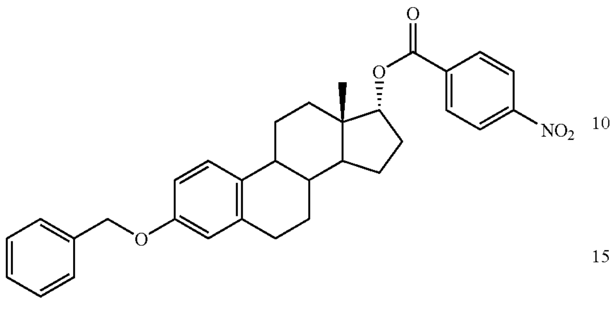

$C_{32}H_{33}NO_5$ MW 511.61 Mp 129–135° C. (litt. 135–136° C.) SRI patent WO 99/33858, Tanabe et al. $^1H$ NMR 400 MHz ($CDCl_3$): 0.88 (s, 3H, C-18-C$\underline{H}_3$), 1.20–1.82 (m, 8H), 1.90–2.02 (m, 2H), 2.20–2.44 (m, 3H), 2.78–2.96 (m, 2H, C-6-H), 5.03 (s, 2H, —$OCH_2Ph$), 5.15 (d, 1H, J=6.25 Hz, 17□-H), 6.73 (d, 1H, J=2.7 Hz, C-4-H), 6.78 (dd, 1H, J=2.7 and 8.6 Hz, C-2-H), 7.19 (d, 1H, J=8.6 Hz, C-1-H), 7.28–7.46 (m, 5H, ArH) and 8.18–8.34 (m, 4H, ArH). M/S m/z (+ve FAB, rel. int.): 511.3 (50, $M^+$), 345.3 (15), 91.1 (100). M/S m/z (−ve FAB, rel. int.): 511.2 (100, $M^-$). HRMS (+ve FAB) m/z calcd for $C_{32}H_{33}NO_5$ ($M^+$) 511.23587. found 511.23547 Rf 0.42 (EtOAc:hexane=7:1), SM Rf 0.09

3-Benzyloxyestra-1,3,5(10)-trien-17□-ol BLE99056

To a solution of 3-benzyloxyestra-1,3,5(10)-trien-17α-O-p-nitrobenzoate BLE99053 (0.82 g, 1.60 mmol) in THF (6 ml) and MeOH (6 ml) was added potassium carbonate (0.22 g, 1.60 mmol) and stirred for 2 h at room temperature. The reaction mixture was quenched with $H_2O$ (30 ml) and extracted with EtOAc (3×100 ml). The combined organic layers were washed with $H_2O$, saturated aqueous NaCl, and then dried ($MgSO_4$), filtered and evaporated in vacuo. The crude product was purified by flash chromatography (column Ø=3 cm, h=22 cm) using as eluent hexane:EtOAc=5:1 to 3:1 to afford 0.49 g (84.5% yield) of a white solid, the 3-benzyloxyestra-1,3,5(10)-trien-17□-ol BLE99056.

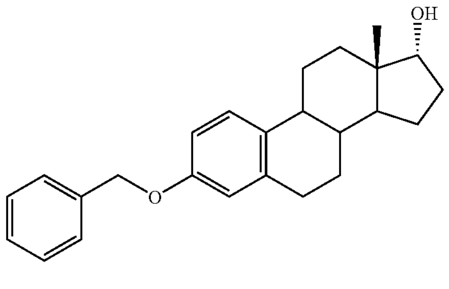

$C_{25}H_{30}O_2$ MW 362.50 Mp 84–85° C. (lit. 85–86° C.) SRI patent WO 99/33858, Tanabe et al. $^1H$ NMR 400 MHz ($CDCl_3$): 0.70 (s, 3H, C-18-C$\underline{H}_3$), 1.18–1.97 (m, 8H), 2.16–2.28 (m, 2H), 2.30–2.40 (m, 1H), 2.76–2.94 (m, 2H, C-6-H), 3.80 (d, 1H, J=5.86 Hz, 17□-H), 5.03 (s, 2H, —$OCH_2Ph$), 6.72 (d, 1H, J=2.7 Hz, C-4-H), 6.78 (dd, 1H, J=2.7 and 8.6 Hz, C-2-H), 7.22 (d, 1H, J=8.6 Hz, C-1-H) and 7.29–7.45 (m, 5H, ArH), not seen —OH. M/S m/z (+ve FAB, rel. int.): 362.3 (70, $M^+$), 345.2 (16), 91.1 (100). HRMS (+ve FAB) m/z calcd for $C_{25}H_{30}O_2$ ($M^+$) 362.22458. found 362.22425 Rf 0.15 (EtOAc;hexane=1:5), SM Rf 0.54

3-Benzyloxyestra-1,3,5(10)-trien-17□-O-sulfamate BLE99059

To a solution of 3-benzyloxyestra-1,3,5(10)-trien-17α-ol BLE99056 (0.49 g, 1.35 mmol) in 15 ml of anhydrous DMF was treated at 0° C. under $N_2$ atmosphere a solution of t-BuOK 1 M in THF (1.62 ml, 1.62 mmol). The reaction mixture was stirred 15 min at 0° C., then a solution of sulphamoyl chloride about 0.7 M in toluene (9.93 ml, 6.76 mmol) was added dropwise at 0° C. The solution was stirred 2 h at room temperature. A saturated solution of $NH_4Cl$ was added at 0° C. (5 ml) then water (20 ml) and the solution was extracted with EtOAc (3×70 ml). The organic layer was washed with brine (3×50 ml), dried over $MgSO_4$, filtered and evaporated to give 0.59 g (98% yield) of the 3-benzyloxyestra-1,3,5(10)-trien-17α-O-sulfamate BLE99059 as a white solid.

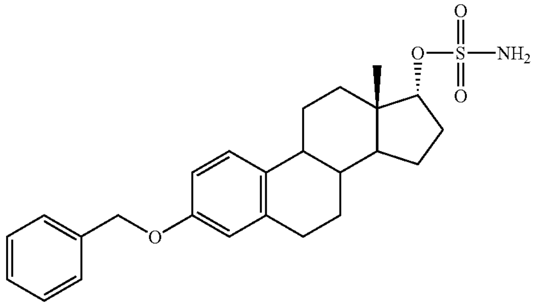

$C_{25}H_{31}NO_4S$ MW 441.58 Mp 91–93° C. $^1H$ NMR 270 MHz ($CDCl_3$): 0.80 (s, 3H, C-18-C$\underline{H}_3$), 1.20–2.45 (m, 13H), 2.70–2.95 (m, 2H, C-6-H), 4.26 (d, 1H, J=Hz, C-17□-H), 4.75 (s br, 2H exch. $D_2O$, $NH_2$), 5.03 (s, 2H, —$OCH_2Ph$), 6.72 (d, 1H, J=2.5 Hz, C-4-H), 6.78 (dd, 1H, J=2.5 and 8.6 Hz, C-2-H), 7.20 (d, 1H, J=8.6 Hz, C-1-H) and 7.30–7.50 (m, 5H, ArH). M/S m/z (+ve FAB, rel. int.): 441.2 (9, $M^+$), 344.3 (84), 91.1 (100). M/S m/z (−ve FAB, rel. int.): 440.2 [61, $(M-H)^-$], 402.1 (33), 249.0 (100), 171.0 (50), 96.0 (86). HRMS (+ve FAB) m/z calcd for $C_{25}H_{31}NO_4S$ ($M^+$) 441.19738. found 441.19757 Rf 0.34 (EtOAc:hexane=1:2), SM Rf 0.46

3-Benzyloxyestra-1,3,5(10)-trien-17β-O-(N,N-dibenzyl)sulfamate BLE99055

To a solution of 3-benzyloxyestra-1,3,5(10)-trien-17β-O-sulfamate BLE99052 (0.30 g, 0.68 mmol) and benzyl bromide (0.33 ml, 2.72 mmol) in 10 ml of anhydrous DMF was added, at room temperature under $N_2$ atmosphere, sodium hydride (60% in mineral oil, 0.06 g, 1.36 mmol) and the reaction mixture was stirred overnight. The reaction was diluted with EtOAc (50 ml) followed by addition of water (30 ml). Upon separation of the aqueous layer, the organic layer was further washed with brine (3×50 ml), dried ($MgSO_4$), filtered and evaporated to give a crude product which was purified by flash chromatography (column Ø=3 cm, h=23 cm) using as eluent hexane:EtOAc=5:1 to afford 0.38 g (89% yield) of a white solid, the 3-benzyloxyestra-1,3,5(10)-trien-17□-O-(N,N-dibenzyl)sulfamate BLE99055.

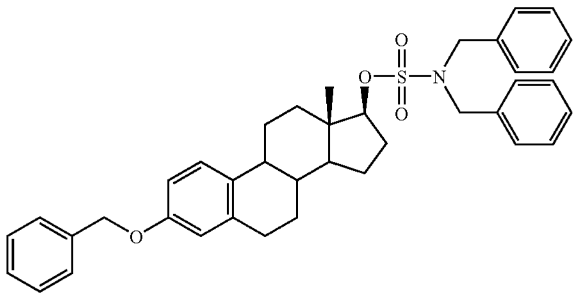

$C_{39}H_{43}NO_4S$ MW 621.83 Mp 92–93° C. $^1H$ NMR 400 MHz ($CDCl_3$): 0.78 (s, 3H, C-18-C$\underline{H}_3$), 1.16–2.34 (m, 13H), 2.78–2.93 (m, 2H), 4.32 (s, 4H, —$NCH_2Ph$), 4.48 (t, 1H, J=9 Hz, 17□-H), 5.03 (s, 2H, —$OCH_2Ph$), 6.71 (d, 1H, J=2.7 Hz, C-4-H), 6.78 (dd, 1H, J=2.7 and 8.6 Hz, C-2-H), 7.19 (d, 1H, J=8.6 Hz, C-1-H) and 7.28–7.45 (m, 15H, ArH). M/S m/z (+ve FAB, rel. int.): 621.3 (34, $M^+$), 345.2 (56), 91.1 (100). HRMS (+ve FAB) m/z calcd for $C_{39}H_{43}NO_4S$ ($M^+$) 621.29128. found 621.29056 Rf 0.46 (EtOAc:hexane=1:5), SM Rf 0.05

3-Benzyloxyestra-1,3,5(10)-trien-17α-O-(N,N-dibenzyl)sulfamate BLE99061

To a solution of 3-benzyloxyestra-1,3,5(10)-trien-17α-O-sulfamate BLE99059 (0.30 g, 0.68 mmol) and benzyl bromide (0.33 ml, 2.72 mmol) in 10 ml of anhydrous DMF was added, at room temperature under $N_2$ atmosphere, sodium hydride (60% in mineral oil, 0.06 g, 1.36 mmol) and the reaction mixture was stirred 28 h. The reaction was diluted with EtOAc (50 ml) followed by addition of water (50 ml). Upon separation of the aqueous layer, the organic layer was further washed with brine (3×50 ml), dried ($MgSO_4$), filtered and evaporated to give a crude product which was purified by flash chromatography (column Ø=3 cm, h=20 cm) using as eluent hexane:EtOAc=9:1 to afford 0.20 g (47% yield) of a white solid (after recrystallisation in hexane), the 3-benzyloxyestra-1,3,5(10)-trien-17□-O-(N,N-dibenzyl)sulfamate BLE99061.

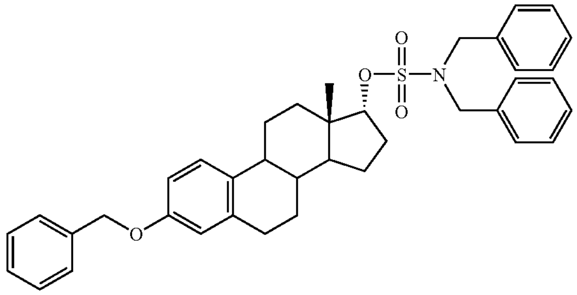

$C_{39}H_{43}NO_4S$ MW 621.83 Mp 115–116° C. $^1H$ NMR 400 MHz ($CDCl_3$): 0.73 (s, 3H, C-18-C$\underline{H}_3$), 1.20–2.34 (m, 13H), 2.78–2.94 (m, 2H, C-6-H), 4.26 (d, 2H, $J_{BA}$=15.6 Hz, 2×NC$\underline{H}_A H_B$Ph), 4.40 (d, 2H, $J_{AB}$=15.6 Hz, 2×NC$H_A\underline{H}_B$Ph), 4.60 (d, 1H, J=5.4 Hz, 17□-H), 5.04 (s, 2H, —OC$\underline{H}_2$Ph), 6.73 (d, 1H, J=2.7 Hz, C-4-H), 6.79 (dd, 1H, J=2.7 and 8.6 Hz, C-2-H), 7.20 (d, 1H, J=8.6 Hz, C-1-H) and 7.27–7.46 (m, 15H, ArH). M/S m/z (+ve FAB, rel. int.): 621.2 (32, $M^+$), 345.2 (78), 91.1 (100). HRMS (+ve FAB) m/z calcd for $C_{39}H_{43}NO_4S$ ($M^+$) 621.29128. found 621.29028 Rf 0.67 (EtOAc:hexane=1:4), SM Rf 0.00

3-Benzyloxyestra-1,3,5(10)-trien-17β-O-(N-acetyl)sulfamate BLE99054

To a solution of 3-benzyloxyestra-1,3,5(10)-trien-17β-O-sulfamate BLE99052 (0.30 g, 0.68 mmol) in 20 ml of anhydrous $CH_2Cl_2$ was added, at room temperature under $N_2$ atmosphere, sodium hydride (60% in mineral oil, 0.027 g, 0.68 mmol) and acetyl chloride (53.1 □l, 0.75 mmol). The reaction mixture was stirred 16 h. The solvent was removed in vacuo and the crude mixture was purified by flash chromatography (column Ø=3 cm, h=23 cm) using as eluent hexane:EtOAc=2:1 to 1:1 to afford 0.10 g (33% yield) of starting material BLE99052, then 0.15 g (46% yield) of a white solid the 3-benzyloxyestra-1,3,5(10)-trien-17β-O-(N-acetyl)sulfamate BLE99054.

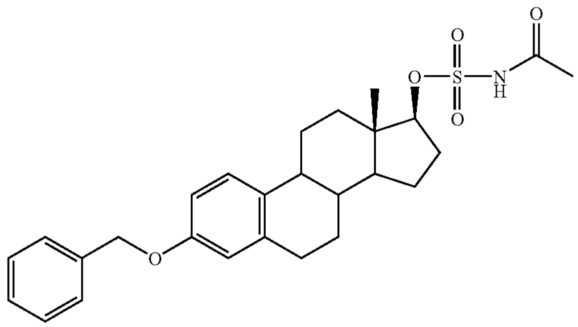

$C_{27}H_{33}NO_5S$ MW 483.62 Mp 82–85° C. $^1H$ NMR 400 MHz ($CDCl_3$): 0.89 (s, 3H, C-18-C$\underline{H}_3$), 1.20–2.36 (m, 13H), 2.23 (s, 3H, C$\underline{H}_3$CO—), 2.77–2.93 (m, 2H, C-6-H), 4.68 (t, 1H, J=8.4 Hz, 17□-H), 5.03 (s, 2H, —OC$\underline{H}_2$Ph), 6.72 (d, 1H, J=2.9 Hz, C-4-H), 6.78 (dd, 1H, J=2.9 and 8.6 Hz, C-2-H), 7.18 (d, 1H, J=8.6 Hz, C-1-H), 7.28–7.46 (m, 5H, ArH) and 8.70 (s br, 1H exch. $D_2O$, —N$\underline{H}$—). M/S m/z (+ve FAB, rel. int.): 483.3 (34, $M^+$), 345.3 (30), 91.1 (100). M/S m/z (−ve FAB, rel. int.): 482.2 [100, $(M-H)^-$]. HRMS (+ve FAB) m/z calcd for $C_{27}H_{33}NO_5S$ ($M^+$) 483.20794. found 483.20785 Rf 0.18 (EtOAc;hexane=1:1)

3-Benzyloxyestra-1,3,5(10)-trien-17β-O-(N,N-dimethyl)sulfamate BLE99064

To a solution of 3-benzyloxyestra-1,3,5(10)-trien-17β-O-sulfamate BLE99052 (0.30 g, 0.68 mmol) in 10 ml of anhydrous DMF was added, at room temperature under $N_2$ atmosphere, sodium hydride (60% in mineral oil, 0.060 g, 1.36 mmol) and methyl iodide (0.169 ml, 2.72 mmol). The reaction mixture was stirred overnight. The reaction was diluted with EtOAc (50 ml) followed by addition of water (50 ml). Upon separation of the aqueous layer, the organic layer was further washed with brine (3×50 ml), dried ($MgSO_4$), filtered and evaporated to give 0.31 g (99% crude yield) of a crude pale yellow solid, the 3-benzyloxyestra-1,3,5(10)-trien-17β-O-(N,N-dimethyl)sulfamate BLE99064.

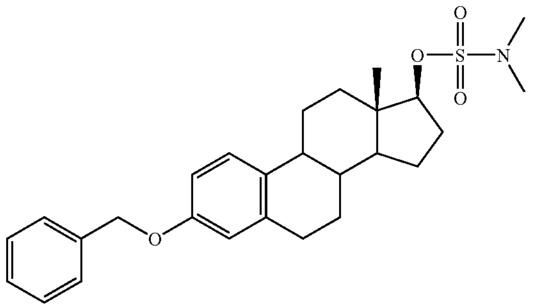

$C_{27}H_{35}NO_4S$ MW 469.64 Mp 117–121° C. $^1H$ NMR 270 MHz ($CDCl_3$): 0.86 (s, 3H, C-18-C$\underline{H}_3$), 1.15–2.40 (m, 13H), 2.23 (s, 3H, C$\underline{H}_3$CO—), 2.75–2.90 (m, 2H, C-6-H), 2.87 (s, 6H, —N($\underline{CH}_3$)$_2$), 4.46 (t, 1H, J=7.9 Hz, 17□-H), 5.03 (s, 2H, —OC$\underline{H}_2$Ph), 6.72 (d, 1H, J=2.7 Hz, C-4-H), 6.78 (dd, 1H, J=2.7 and 8.4 Hz, C-2-H), 7.19 (d, 1H, J=8.4 Hz, C-1-H) and 7.25–7.45 (m, 5H, ArH). M/S m/z (+ve FAB, rel. int.): 469.2 (50, $M^+$), 345.2 (45.6), 91.1 (100). HRMS (+ve FAB) m/z calcd for $C_{27}H_{35}NO_4S$ ($M^+$) 469.22868. found 469.22845 Rf 0.46 (AcOEt:hexane=1:4), SM Rf 0.13

3-Hydroxyestra-1,3,5(10)-trien-17β-O-(N,N-dibenzyl)sulfamate BLE99060

To a solution of 3-benzyloxyestra-1,3,5(10)-trien-17β-O-(N,N-dibenzyl)sulfamate BLE99055 (0.20 g, 0.38 mmol) in 20 ml MeOH was added 10% palladium on carbon (0.10 g). The reaction mixture was stirred 7 h under a hydrogen atmosphere at room temperature. After the catalyst was filtered, the solvent was evaporated at reduced pressure to afford 0.23 g (83.5% yield) of the 3-hydroxyestra-1,3,5(10)-trien-17β-O-(N,N-dibenzyl)sulfamate BLE99060 as a white solid.

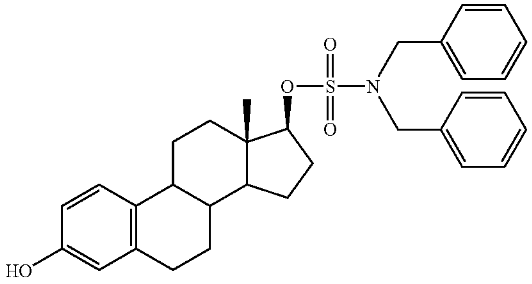

$C_{32}H_{37}NO_4S$ MW 531.71 Mp 60–63° C. $^1H$ NMR 400 MHz ($CDCl_3$) 0.78 (s, 3H, C-18-C$\underline{H}_3$), 1.27–2.34 (m, 13H), 2.76–2.84 (m, 2H), 4.32 (s, 4H, 2×—N($\underline{CH}_2$)—), 4.49 (t, 1H, J=8.5 Hz, 17□-H), 6.56 (d, 1H, J=2.7 Hz, C-4-H), 6.63 (dd, 1H, J=2.7 and 8.2 Hz, C-2-H), 7.14 (d, 1H, J=8.2 Hz, C-1-H), 7.28–7.39 (m, 10H, ArH) and not seen —OH. M/S m/z (+ve FAB, rel. int.): 531.2 (28, $M^+$), 255.2 (100), 91.1 (84). M/S m/z (−ve FAB, rel. int.): 530.2 [56, $(M-H)^-$], 276.1 (100). HRMS (+ve FAB) m/z calcd for $C_{32}H_{37}NO_4S$ ($M^+$) 531.24433. found 531.24232 Rf 0.15 (EtOAc:hexane=1:5), SM Rf 0.43

3-Hydroxyestra-1,3,5(10)-trien-17α-O-(N,N-dibenzyl)sulfamate BLE99066

To a solution of 3-benzyloxyestra-1,3,5(10)-trien-17α-O-(N,N-dibenzyl)sulfamate BLE99061 (0.195 g, 0.31 mmol) in 10 ml MeOH and 5 ml of THF was added 10% palladium on carbon (0.075 g). The reaction mixture was stirred 3 h under a hydrogen atmosphere at room temperature. After the catalyst was filtered, the solvent was evaporated at reduced pressure to afford 0.15 g (90.5% yield) of the 3-hydroxyestra-1,3,5(10)-trien-17α-O-(N,N-dibenzyl)sulfamate BLE99066 as a white solid.

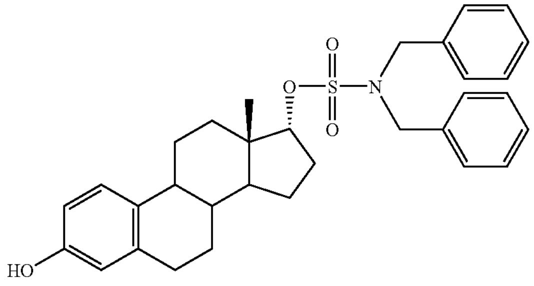

$C_{32}H_{37}NO_4S$ MW 531.71 Mp 57–60° C. $^1H$ NMR 270 MHz ($CDCl_3$): 0.73 (s, 3H, C-18-C$\underline{H}_3$), 1.20–2.40 (m, 13H), 2.75–3.00 (m, 2H), 4.26 (d, 2H, $J_{BA}$=15.4 Hz, 2×NC$\underline{H}_A$$H_B$Ph), 4.40 (d, 2H, $J_{AB}$=15.4 Hz, 2×NC$H_A$$\underline{H}_B$Ph), 4.59 (d, 1H, J=5.5 Hz, 17□-H), 6.55–6.70 (m, 2H, C-4-H and C-2-H), 7.15 (d, 1H, J=8.4 Hz, C-1-H) and 7.25–7.45 (m, 10H, ArH) and not seen —OH. M/S m/z (+ve FAB, rel. int.): 531.3 (10, $M^+$), 255.2 (100), 91.1 (98). M/S m/z (−ve FAB, rel. int.): 530.2 [6, $(M-H)^-$], 276.1 (100). HRMS (+ve FAB) m/z calcd for $C_{32}H_{37}NO_4S$ ($M^+$) 531.24433. found 531.24255 Rf 0.43 (EtOAc:hexane=1:4), SM Rf 0.66

3-Hydroxyestra-1,3,5(10)-trien-17β-O-(N-acetyl)sulfamate BLE99058

To a solution of 3-benzyloxyestra-1,3,5(10)-trien-17βO-(N-acetyl)sulfamate BLE99054 (0.11 g, 0.23 mmol) in 10 ml MeOH was added 10% palladium on carbon (0.05 g). The reaction mixture was stirred 5 h under a hydrogen atmosphere at room temperature. After the catalyst was filtered, the solvent was evaporated at reduced pressure to afford 0.09 g (87% yield) of the 3-hydroxyestra-1,3,5(10)-trien-17β-O-(N-acetyl)sulfamate BLE99058 as a white solid.

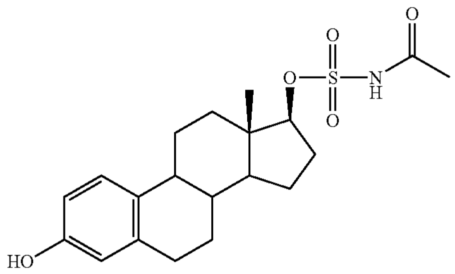

$C_{20}H_{27}NO_5S$ MW 393.50 Mp 130–134° C. (dec.) $^1H$ NMR 400 MHz ($CD_3OD/CDCl_3$): 0.88 (s, 3H, C-18-C$\underline{H}_3$), 1.18–2.34 (m, 13H), 2.13 (s, 3H, C$\underline{H}_3$CO—), 2.70–2.90 (m, 2H, C-6-H), 3.48 (s br, 2H exch. $D_2O$, —N$\underline{H}$— & —O$\underline{H}$), 4.63 (dd, 1H, J=7.8 and J=9.4 Hz, 17□-H), 6.56 (s, 1H, J=2.7 Hz, C-4-H), 6.63 (dd, 1H, J=2.7 and 8.6 Hz, C-2-H) and 7.11 (d, 1H, J=8.6 Hz, C-1-H). M/S m/z (+ve FAB, rel. int.): 393.2 (86, $M^+$), 255.2 (100). M/S m/z (−ve FAB, rel. int.): 392.1 [100, $(M-H)^-$]. HRMS (+ve FAB) m/z calcd for $C_{20}H_{27}NO_5S$ ($M^+$) 393.16099. found 393.16132 Rf 0.12 (EtOAc:hexane=1:1) SM Rf 0.18

3-Hydroxyestra-1,3,5(10)-trien-17β-O-(N,N-dimethyl)sulfamate BLE99067

To a solution of 3-benzyloxyestra-1,3,5(10)-trien-17βO-(N,N-dimethyl)sulfamate BLE99064 (0.31 g, 0.66 mmol) in 20 ml MeOH and 5 ml THF was added 10% palladium on carbon (0.15 g). The reaction mixture was stirred overnight under a hydrogen atmosphere at room temperature. After the catalyst was filtered, the solvent was evaporated at reduced pressure to afford 0.205 g (82% yield) of the 3-hydroxyestra-1,3,5(10)-trien-17β-O-(N,N-dimethyl)sulfamate BLE99067 as a white solid.

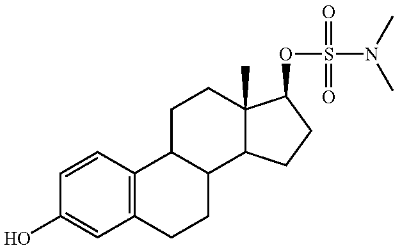

$C_{20}H_{29}NO_4S$ MW 379.51 Mp 170–173° C. $^1$H NMR 400 MHz ($CDCl_3$): 0.86 (s, 3H, C-18-C$\underline{H}_3$), 1.18–2.36 (m, 13H), 2.13 (s, 3H, C$\underline{H}_3$CO—), 2.74–2.90 (m, 2H, C-6-H), 2.87 (s, 6H, —N$\underline{Me}_2$), 4.63 (dd, 1H, J=7.8 and J=9.4 Hz, 17□-H), 6.56 (s, 1H, J=2.7 Hz, C-4-H), 6.63 (dd, 1H, J=2.7 and 8.6 Hz, C-2-H) and 7.11 (d, 1H, J=8.6 Hz, C-1-H) and not seen —OH. M/S m/z (+ve FAB, rel. int.): 379.2 (16, $M^+$), 255.2 (58), 111.1 (59), 97.1 (100). M/S m/z (−ve FAB, rel. int.): 378.1 [100, $(M-H)^-$], 124 (52). HRMS (+ve FAB) m/z calcd for $C_{20}H_{29}NO_4S$ ($M^+$) 379.18173. found 379.18177

3-O-Sulfamoyl-estra-1,3,5(10)-trien-17β-O-(N,N-dibenzyl)sulfamate BLE99063

To a solution of 3-hydroxyestra-1,3,5(10)-trien-17β-O-(N,N-dibenzyl)sulfamate BLE99060 (0.20 g, 0.38 mmol) in anhydrous dichloromethane (10 ml) was added at room temperature 2,6-di-tert-butyl-4-methylpyridine (DBMP) (0.23 g, 1.13 mmol) and dropwise, via syringe, a solution of sulfamoyl chloride 0.7 M in toluene (2.77 ml, 1.88 mmol). The reaction mixture was stirred at room temperature 16 h. Dichloromethane was added (40 ml) and $H_2O$ (40 ml). Upon separation of the aqueous layer, the organic layer was washed with brine (2×50 ml), dried ($MgSO_4$), filtered and evaporated to give a colorless oil which was fractionated by flash chromatography (column Ø=3 cm, h=20 cm) using as eluent hexane: EtOAc=4:1 to 3:2 to afford 0.194 g (84.5% yield) of a white solid (foam), the 3-O-sulfamoyl-estra-1,3,5(10)-trien-17β-O-(N,N-dibenzyl)sulfamate BLE99063.

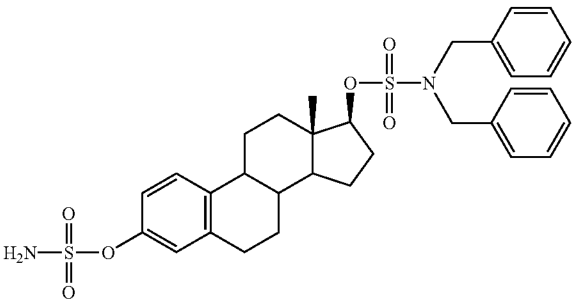

$C_{32}H_{38}N_2O_6S_2$ MW 610.78 Mp 58–62° C. $^1$H NMR 400 MHz ($CDCl_3$): 0.78 (s, 3H, C-18-C$\underline{H}_3$), 1.18–2.32 (m, 13H), 2.85–2.92 (m, 2H, C-6-H), 4.32 (s, 4H, —$NCH_2Ph$), 4.49 (t, J=8.4 Hz, 17□-H), 4.88 (s, 2H exch. $D_2O$, —$NH_2$), 7.04 (d, 1H, J=2.3 Hz, C-4-H), 7.08 (dd, 1H, J=2.3 and J=8.4 Hz, C-2-H) and 7.28–7.38 (m, 11H, ArH and C1-H). M/S m/z (+ve FAB, rel. int.): 611.1 [7, $(M+H)^+$], 334.1 (100), 91.1 (91.1). M/S m/z (−ve FAB, rel. int.): 609.1 [100, $(M-H)^-$]. HRMS (−ve FAB) m/z calcd for $C_{32}H_{37}N_2O_6S_2$ $(M-H)^-$ 609.20931. found 609.20914 Rf 0.60 (EtOAc;hexane=2:3), SM Rf 0.75

| | | | | | | |
|---|---|---|---|---|---|---|
| Microanalysis Found: | % C | 62.80 | % H | 6.32 | % N | 4.53 |
| Theor. | | 62.93 | | 6.27 | | 4.59 |

3-O-Sulfamoyl-estra-1,3,5(10)-trien-17α-O-(N,N-dibenzyl)sulfamate BLE99068

To a solution of 3-hydroxyestra-1,3,5(10)-trien-17α-O-(N,N-dibenzyl)sulfamate BLE99066 (0.122 g, 0.23 mmol) in anhydrous dichloromethane (7 ml) was added at room temperature 2,6-di-tert-butyl-4-methylpyridine (DBMP) (0.14 g, 0.69 mmol) and dropwise, via syringe, a solution of sulfamoyl chloride 0.7 M in toluene (1.69 ml, 1.15 mmol). The reaction mixture was stirred at room temperature 19 h. Dichloromethane was added (30 ml) and $H_2O$ (30 ml). Upon separation of the aqueous layer, the organic layer was washed with brine (2×50 ml), dried ($MgSO_4$), filtered and evaporated to give a colorless oil which was fractionated by flash chromatography (column Ø=3 cm, h=20 cm) using as eluent hexane:EtOAc=4:1 to 3:2 to afford 0.073 g (52% yield) of a white solid, the 3-O-sulfamoyl-estra-1,3,5(10)-trien-17β-O-(N,N-dibenzyl)sulfamate BLE99068.

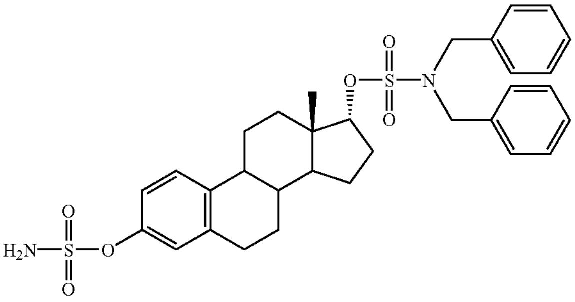

$C_{32}H_{38}N_2O_6S_2$ MW 610.78 Mp 60–64° C. $^1$H NMR 400 MHz ($CDCl_3$): 0.74 (s, 3H, C-18-C$\underline{H}_3$), 1.18–2.36 (m, 13H), 2.85–2.92 (m, 2H, C-6-H), 4.27 (d, 2H, $J_{BA}$=15.2 Hz, 2×NC$\underline{H}_A H_B$Ph), 4.40 (d, 2H, JAB=15.2 Hz, 2×NC$H_A\underline{H}_B$Ph), 4.59 (t, J=5.4 Hz, 17□-H), 4.90 (s br, 2H exch. $D_2O$, —$NH_2$), 7.05 (d, 1H, J=2.7 Hz, C-4-H), 7.09 (dd, 1H, J=2.7 and J=8.6 Hz, C-2-H), 7.14 (d, 1H, J=8.6 Hz, C-1-H) and 7.28–7.38 (m, 10H, ArH). M/S m/z (–ve FAB, rel. int.): 609.1 [40, $(M-H)^-$], 332.1 (15), 276.1 (100), 181.1 (4), 106.1 (4), 78.0 (12). HRMS (–ve FAB) m/z calcd for $C_{32}H_{37}N_2O_6S_2$, $(M-H)^-$ 609.20931. found 609.20840

| | | | | | | |
|---|---|---|---|---|---|---|
| Microanalysis Found: | % C | 62.70 | % H | 6.29 | % N | 4.44 |
| Theor. | | 62.93 | | 6.27 | | 4.59 |

3-O-Sulfamoyl-estra-1,3,5(10)-trien-17β-O-(N-acetyl)sulfamate BLE99065

To a solution of 3-hydroxyestra-1,3,5(10)-trien-17β-O-(N-acetyl)sulfamate BLE99058 (67 mg, 0.17 mmol) in anhydrous dimethylformamide (5 ml) was added at room temperature 2,6-di-tert-butyl-4-methylpyridine (DBMP) (0.105 g, 0.51 mmol) and dropwise, via syringe, a solution of sulfamoyl chloride 0.7 M in toluene (1.25 ml, 0.85 mmol). The reaction mixture was stirred at room temperature 7 h. EtOAc was added (50 ml) and $H_2O$ (40 ml). Upon separation of the aqueous layer, the organic layer was washed with brine (3×40 ml), dried ($MgSO_4$), filtered and evaporated to give an oil which was fractionated by flash chromatography (column Ø=1.5 cm, h=23 cm) using as eluent hexane:EtOAc=2:1 to afford 27 mg (34% yield) of a orange pale solid the 3-O-sulfamoyl-estra-1,3,5(10)-trien-17□-O-(N-acetyl)sulfamate BLE99065.

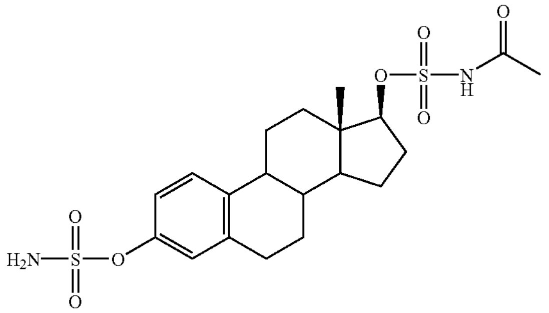

$C_{20}H_{28}N_2O_7S_2$ MW 472.58 Mp 76–80° C. (dec.) $^1H$ NMR 400 MHz ($CDCl_3$): 0.89 (s, 3H, C-18-C$\underline{H}_3$), 1.20–2.38 (m, 13H), 2.24 (s, 3H, $\underline{CH}_3$CO—), 2.80–2.86 (m, 2H, C-6-H), 4.69 (t, 1H, J=8.7 Hz, C-17□-H), 4.95 (s br, 2H exch. $D_2O$, —$NH_2$), 7.04 (d, 1H, J=2.7 Hz, C-4-H), 7.08 (dd, 1H, J=2.7 and J=8.6 Hz, C-2-H), 7.28 (d, 1H, J=8.6 Hz, C-1-H) and 8.12 (s br, 1H exch. $D_2O$, —NHAc). M/S m/z (+ve FAB, rel. int.): 472.2 (20, $M^+$), 420.3 (22), 393.3 (14), 334.2 (86), 255.3 (46), 239.2 (30), 219.2 (38), 203.2 (26), 183.2 (30), 173.2 (58), 157.2 (40), 133.1 (48), 111.2(61), 97.1 (100), 84.1 (30), 73.1 (92). M/S m/z (–ve FAB, rel. int.): 471.1 [100, $(M-H)^-$], 403.1 (20), 392.2 (15), 332.1 (46), 250.1 (64), 97 (74). HRMS (–ve FAB) m/z calcd for $C_{20}H_{28}N_2O_7S_2$ $(M-H)^-$ 471.12597. found 471.12579

3-O-Sulfamoyl-estra-1,3,5(10)-trien-17β-O-(N,N-dimethyl)sulfamate BLE99069

To a solution of 3-hydroxyestra-1,3,5(10)-trien-17β-O-(N,N-dimethyl)sulfamate BLE99067 (180 mg, 0.47 mmol) in anhydrous $CH_2Cl_2$ (5 ml) was added at room temperature 2,6-di-tert-butyl-4-methylpyridine (DBMP) (0.292 g, 1.42 mmol) and dropwise, via syringe, a solution of sulfamoyl chloride 0.7 M in toluene (3.49 ml, 2.37 mmol). The reaction mixture was stirred at room temperature 19 h. EtOAc was added (50 ml) and $H_2O$ (40 ml). Upon separation of the aqueous layer, the organic layer was washed with brine (3×40 ml), dried ($MgSO_4$), filtered and evaporated to give an oil which was fractionated by flash chromatography (column Ø=3 cm, h=20 cm) using as eluent hexane: EtOAc=3:1 to afford 0.195 g (90% yield) of a white solid the 3-O-sulfamoyl-estra-1,3,5(10)-trien-17β-O-(N,N-dimethyl) sulfamate BLE99069.

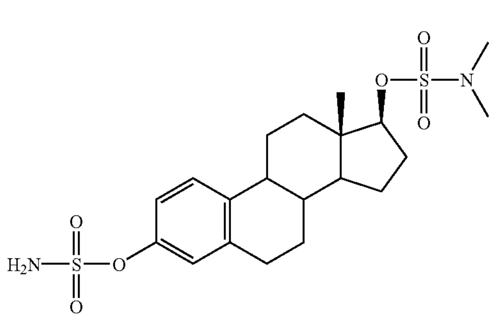

$C_{20}H_{30}N_2O_6S_2$ MW 458.59 Mp 140–142° C. $^1H$ NMR 400 MHz ($CDCl_3$): 0.86 (s, 3H, C-18-C$\underline{H}_3$), 1.20–2.38 (m, 13H), 2.24 (s, 3H, $\underline{CH}_3$CO—), 2.80–2.92 (m, 2H, C-6-H), 2.88 (s, 6H, —$NMe_2$), 4.69 (t, 1H, J=7.8 Hz, C-17□-H), 4.89 (s br, 2H exch. $D_2O$, —$NH_2$), 7.04 (d, 1H, J=2.7 Hz, C-4-H), 7.08 (dd, 1H, J=2.7 and J=8.6 Hz, C-2-H) and 7.31 (d, 1H, J=8.6 Hz, C-1-H). M/S m/z (+ve FAB, rel. int.):458.2 (18, $M^+$), 334.2 (100), 255.3 (13), 238.1 (17), 212.1 (9), 173.2 (12), 133.1 (12), 97.1 (12). HRMS (+ve FAB) m/z calcd for $C_{20}H_{30}N_2O_6S_2$ $M^+$ 458.15453. found 458.15371

| | | | | | | |
|---|---|---|---|---|---|---|
| Microanalysis Found: | % C | 52.40 | % H | 6.63 | % N | 6.06 |
| Theor. | | 52.38 | | 6.59 | | 6.11 |

3-Benzyloxyestra-1,3,5(10)-trien-17β-O-(N,N-di-pentyl)sulfamate BLE99072

To a solution of 3-benzyloxyestra-1,3,5(10)-trien-17β-O-sulfamate BLE99070 (0.40 g, 0.91 mmol) and pentyl bromide (0.45 ml, 3.62 mmol) in 12 ml of anhydrous DMF was added, at room temperature under $N_2$ atmosphere, sodium hydride (60% in mineral oil, 72.5 mg, 1.81 mmol) and the reaction mixture was stirred for 16 h. The reaction was diluted with EtOAc (50 ml) followed by addition of water (30 ml). Upon separation of the aqueous layer, the organic layer was further washed with brine (3×50 ml), dried ($MgSO_4$), filtered and evaporated to give a crude product which was purified by flash chromatography (column Ø=3 cm, h=20 cm) using as eluent hexane then hexane: EtOAc=9:1 to afford 0.49 g (92.5% yield) of a white solid, the 3-benzyloxyestra-1,3,5(10)-trien-17β-O-(N,N-dipentyl) sulfamate BLE99072.

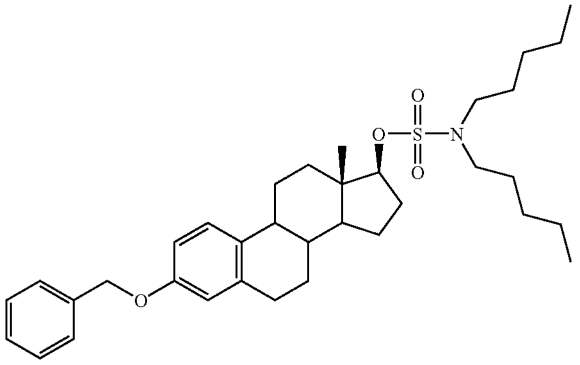

$C_{35}H_{51}NO_4S$ MW 581.85 Mp 55–56° C. $^1H$ NMR 270 MHz ($CDCl_3$): 0.83 (s, 3H, C-18-$CH_3$), 0.91 (t, 6H, J=7.8 Hz, 2×$CH_3CH_2$—), 1.10–2.40 (m, 25H), 2.75–2.90 (m, 2H, C-6-H), 3.10–3.25 (m, 4H, 2×N($CH_2$)), 4.42 (t, 1H, J=8.5 Hz, C-17□-H), 5.03 (s, 2H, —O$CH_2$Ph), 6.71 (d, 1H, J=2.7 Hz, C-4-H), 6.78 (dd, 1H, J=2.7 and 8.6 Hz, C-2-H), 7.19 (d, 1H, J=8.2 Hz, C-1-H) and 7.26–7.48 (m, 5H, ArH). M/S m/z (+ve FAB, rel. int.): 581.2 (28, $M^+$), 345.3 (65), 249.2 (8), 91.1 (100). HRMS (+ve FAB) m/z calcd for $C_{35}H_{51}NO_4S$ $M^+$ 581.35388. found 581.35217 Rf 0.69 (EtOAc:hexane=3:17), SM Rf 0.00

3-Benzyloxyestra-1,3,5(10)-trien-17α-O-(N,N-dipentyl)sulfamate BLE00079

To a solution of 3-benzyloxyestra-1,3,5(10)-trien-17α-O-sulfamate BLE00077 (0.40 g, 0.91 mmol) and pentyl bromide (0.45 ml, 3.62 mmol) in 12 ml of anhydrous DMF was added, at room temperature under $N_2$ atmosphere, sodium hydride (60% in mineral oil, 72.5 mg, 1.81 mmol) and the reaction mixture was stirred for 16 h. The reaction was diluted with EtOAc (50 ml) followed by addition of water (30 ml). Upon separation of the aqueous layer, the organic layer was further washed with brine (3×50 ml), dried ($MgSO_4$), filtered and evaporated to give a crude product which was purified by flash chromatography (column Ø=3 cm, h=22 cm) using as eluent hexane then hexane: EtOAc=40:3 to 8:1 to afford 0.32 g (61% yield) of an uncolourless oil, the 3-benzyloxyestra-1,3,5(10)-trien-17α-O-(N,N-dipentyl)sulfamate BLE00079.

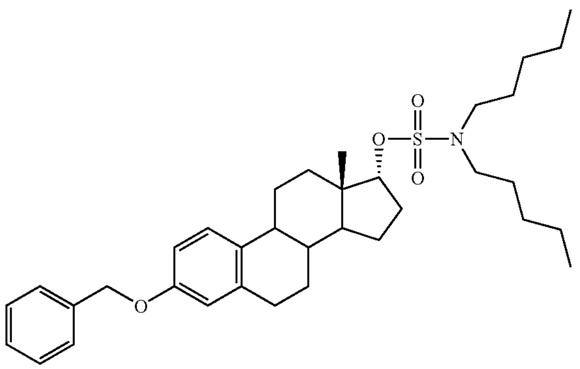

$C_{35}H_{51}NO_4S$ MW 581.85 $^1H$ NMR 400 MHz (DMSO-$d_6$): 0.74 (s, 3H, C-18-$CH_3$), 0.87 (t, 6H, J=7.0 Hz, 2×$CH_3CH_2$—), 1.18–2.40 (m, 25H), 2.70–2.84 (m, 2H, C-6-H), 3.11–3.19 (m, 4H, 2×N($CH_2$)), 4.43 (d, 1H, J=5.5 Hz, C-17□-H), 5.04 (s, 2H, —O$CH_2$Ph), 6.70 (d, 1H, J=2.7 Hz, C-4-H), 6.75 (dd, 1H, J=2.7 and 8.6 Hz, C-2-H), 7.18 (d, 1H, J=8.6 Hz, C-1-H) and 7.28–7.50 (m, 5H, ArH). M/S m/z (+ve FAB, rel. int.): 581.3 (18, $M^+$), 345.3 (100), 249.2 (8), 91.1 (96). HRMS (+ve FAB) m/z calcd for $C_{35}H_{51}NO_4S$ $M^+$ 581.35388. found 581.35399 Rf 0.62 (EtOAc:hexane=2:20), SM Rf 0.00

3-Benzyloxyestra-1,3,5(10)-trien-17α-O-(N,N-dimethyl)sulfamate BLE00078

To a solution of 3-benzyloxyestra-1,3,5(10)-trien-17α-sulfamate BLE00077 (0.40 g, 0.91 mmol) and methyl iodide (0.225 ml, 3.62 mmol) in 10 ml of anhydrous DMF was added, at room temperature under $N_2$ atmosphere, sodium hydride (60% in mineral oil, 80 mg, 1.99 mmol) and the reaction mixture was stirred overnight. The reaction was diluted with EtOAc (50 ml) followed by addition of water (30 ml). Upon separation of the aqueous layer, the organic layer was further washed with brine (3×50 ml), dried ($MgSO_4$), filtered and evaporated to give a crude product which was purified by flash chromatography (column Ø=3 cm, h=20 cm) using as eluent hexane then hexane: EtOAc=5:1 to afford 0.25 g (59% yield) of a white solid, the 3-benzyloxyestra-1,3,5(10)-trien-17α-O-(N,N-dimethyl) sulfamate BLE00078.

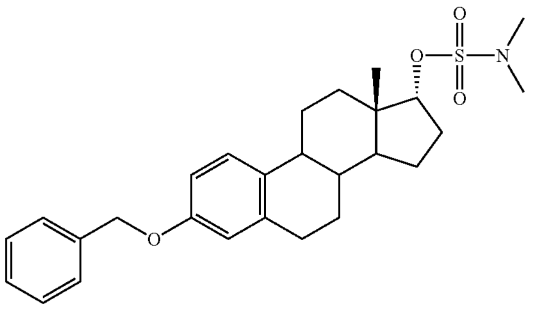

$C_{27}H_{35}NO_4S$ MW 469.64 Mp 82–86° C. (dec.) $^1H$ NMR 400 MHz (DMSO-$d_6$): 0.74 (s, 3H, C-18-$CH_3$), 0.87 (t, 6H, J=7.0 Hz, 2×$CH_3CH_2$—), 1.18–2.40 (m, 25H), 2.70–2.84 (m, 2H, C-6-H), 3.11–3.19 (m, 4H, 2×N($CH_2$)), 4.43 (d, 1H, J=5.5 Hz, C-17□-H), 5.04 (s, 2H, —O$CH_2$Ph), 6.70 (d, 1H, J=2.7 Hz, C-4-H), 6.75 (dd, 1H, J=2.7 and 8.6 Hz, C-2-H), 7.18 (d, 1H, J=8.6 Hz, C-1-H) and 7.28–7.50 (m, 5H, ArH). M/S m/z (+ve FAB, rel. int.): 469.2 (18, $M^+$), 344.2 (73), 91.1 (100). HRMS (+ve FAB) m/z calcd for $C_{27}H_{35}NO_4S$ $M^+$ 469.22868. found 469.22822

3-Hydroxyestra-1,3,5(10)-trien-17β-O-(N,N-dipentyl)sulfamate BLE99073

To a solution of 3-benzyloxyestra-1,3,5(10)-trien-17β-O-(N,N-dipentyl)sulfamate BLE99072 (0.46 g, 0.79 mmol) in 20 ml MeOH and 7 ml THF was added 10% palladium on carbon (0.15 g). The reaction mixture was stirred for 2 h15 under a hydrogen atmosphere at room temperature. After the catalyst was filtered, the solvent was evaporated at reduced pressure to afford 0.31 g (80% yield) of the 3-hydroxyestra- 1,3,5(10)-trien-17β-O-(N,N-dipentyl)sulfamate BLE99073 as a white solid.

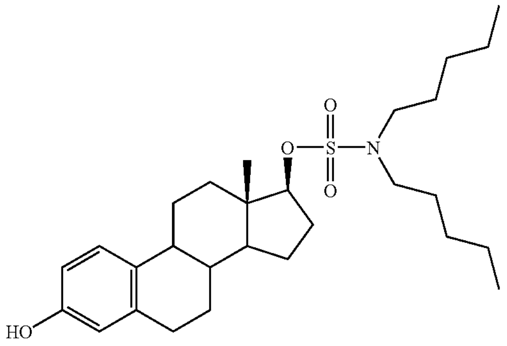

$C_{28}H_{45}NO_4S$ MW 491.73 Mp 93–96° C. $^1H$ NMR 400 MHz ($CDCl_3$): 0.83 (s, 3H, C-18-$CH_3$), 0.91 (t, 6H, J=7.0 Hz, 2×$CH_3CH_2$—), 1.18–2.34 (m, 25H), 2.76–2.86 (m, 2H, C-6-H), 3.12–3.24 (m, 4H, 2×N($CH_2$)), 4.42 (t, 1H, J=8.5 Hz, C-17□-H), 4.58 (s br, 1H exch. $D_2O$, —OH), 6.56 (d, 1H, J=2.7 Hz, C-4-H), 6.62 (dd, 1H, J=2.7 and 8.2 Hz, C-2-H) and 7.14 (d, 1H, J=8.2 Hz, C-1-H). M/S m/z (+ve FAB, rel. int.): 491.3 (16, $M^+$), 255.2 (100), 159.2 (24), 133.1 (13). HRMS (+ve FAB) m/z calcd for $C_{28}H_{45}NO_4S$ $M^+$ 491.30693. found 491.30741 Rf 0.28 (AcOEt:hexane=3:17), SM Rf 0.69

3-Hydroxyestra-1,3,5(10)-trien-17α-O-(N,N-dipentyl)sulfamate BLE00082

To a solution of 3-benzyloxyestra-1,3,5(10)-trien-17α-O-(N,N-dipentyl)sulfamate BLE00079 (0.31 g, 0.53 mmol) in 15 ml MeOH and 8 ml THF was added 10% palladium on carbon (0.10 g). The reaction mixture was stirred for 8 h under a hydrogen atmosphere at room temperature. After the catalyst was filtered, the solvent was evaporated at reduced pressure to afford 0.31 g (80% yield) of the 3-hydroxyestra-1,3,5(10)-trien-17α-O-(N,N-dipentyl)sulfamate BLE00082 as a white solid.

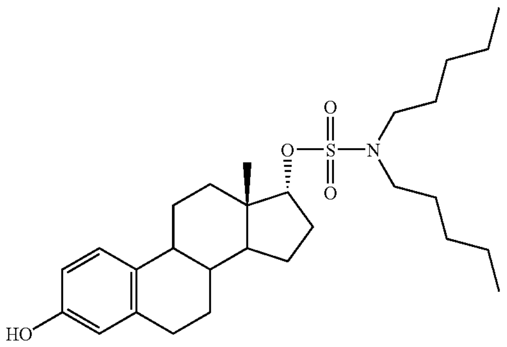

$C_{28}H_{45}NO_4S$ MW 491.73 Mp 104–107° C. $^1H$ NMR 270 MHz ($CD_3OD$): 0.83 (s, 3H, C-18-$CH_3$), 0.91 (t, 6H, J=6.8 Hz, 2×$CH_3CH_2$—), 1.20–2.42 (m, 25H), 2.65–2.85 (m, 2H, C-6-H), 3.18–3.30 (m, 4H, 2×N($CH_2$)), 4.51 (d, 1H, J=5.8 Hz, C-17□-H), 6.52 (d, 1H, J=2.7 Hz, C-4-H), 6.60 (dd, 1H, J=2.7 and 8.4 Hz, C-2-H), 7.12 (d, 1H, J=8.4 Hz, C-1-H), 7.96 (s br, 1H exch. $D_2O$, —OH). M/S m/z (+ve FAB, rel. int.): 491.3 (3, $M^+$), 475.2 (9), 391.3 (2), 255.2 (100), 159.2 (2). M/S m/z (−ve FAB, rel. int.) 490.2 [3, $(M-H)^-$], 335.1 (10), 236.2 (100), 80.0 (12). HRMS (−ve FAB) m/z calcd for $C_{28}H_{44}NO_4S$ $(M-H)^-$ 490.29911. found 490.29850 Rf 0.40 (AcOEt:hexane=1:4)

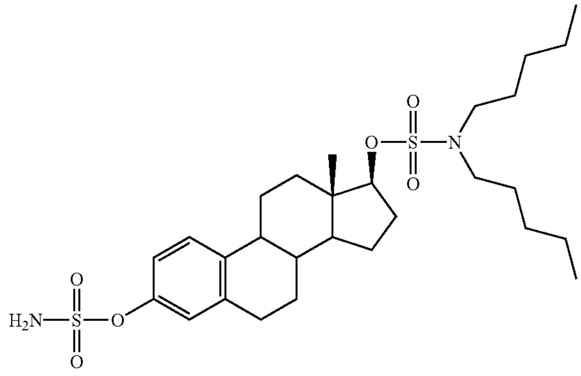

3-O-Sulfamoyl-estra-1,3,5(10)-trien-17β-O-(N,N-dipentyl)sulfamate BLE00074

To a solution of 3-hydroxyestra-1,3,5(10)-trien-17β-O-(N,N-dipentyl)sulfamate BLE99073 (0.26 g, 0.54 mmol) in anhydrous $CH_2Cl_2$ (15 ml) was added at room temperature 2,6-di-tert-butyl-4-methylpyridine (DBMP) (0.33 g, 1.61 mmol) and dropwise, via syringe, a solution of sulfamoyl chloride 0.7 M in toluene (3.95 ml, 2.69 mmol). The reaction mixture was stirred at room temperature 18 h. EtOAc was added (50 ml) and $H_2O$ (50 ml). Upon separation of the aqueous layer, the organic layer was washed with brine (3×50 ml), dried ($MgSO_4$), filtered and evaporated to give an oil which was fractionated by flash chromatography (column Ø=3 cm, h=21 cm) using as eluent hexane:EtOAc=5:1 to afford 0.27 g (89% yield) of a white solid the 3-O-sulfamoyl-estra-1,3,5(10)-trien-17□-O-(N,N-dipentyl)sulfamate BLE00074.

$C_{28}H_{46}N_2O_6S_2$ MW 570.80 Mp 105–107° C. $^1H$ NMR 400 MHz ($CDCl_3$): 0.83 (s, 3H, C-18-$CH_3$), 0.91 (t, 6H, J=7.0 Hz, 2×$CH_3CH_2$—), 1.18–2.38 (m, 25H), 2.82–2.93 (m, 2H, C-6-H), 3.12–3.26 (m, 4H, 2×N($CH_2$)), 4.43 (t, 1H, J=7.8 Hz, 17□-H), 4.89 (s br, 2H exch. $D_2O$, —$NH_2$), 7.04 (d, 1H, J=2.7 Hz, C-4-H), 7.08 (dd, 1H, J=2.7 and 8.6 Hz, C-2-H) and 7.31 (d, 1H, J=8.6 Hz, C-1-H). M/S m/z (+ve FAB, rel. int.): 569.2 (2, $[M-H]^+$), 491.3 (2), 335.1 (100), 255.3 (9), 238.1 (18), 212.1 (7), 159.2 (8), 133.1 (6). M/S m/z (−ve FAB, rel. int.): 569.2 [100, $(M-H)^-$], 236.2 (32), 96.0 (6), 78.0 (28). HRMS (−ve FAB) m/z calcd for $C_{28}H_{45}N_2O_6S_2$ $(M-H)^-$ 569.27191. found 569.27386

| | | | | | | |
|---|---|---|---|---|---|---|
| Microanalysis Found: | % C | 59.10 | % H | 4.84 | % N | 8.29 |
| Theor. | | 58.92 | | 4.91 | | 8.12 |

3-O-Sulfamoyl-estra-1,3,5(10)-trien-17α-O-(N,N-dipentyl)sulfamate BLE00083

To a solution of 3-hydroxyestra-1,3,5(10)-trien-17α-O-(N,N-dipentyl)sulfamate BLE00082 (0.17 g, 0.34 mmol) in anhydrous $CH_2Cl_2$ (10 ml) was added at room temperature 2,6-di-tert-butyl-4-methylpyridine (DBMP) (0.21 g, 0.10 mmol) and dropwise, via syringe, a solution of sulfamoyl chloride 0.7 M in toluene (2.51 ml, 1.71 mmol). The reaction mixture was stirred at room temperature 7 h. EtOAc was added (50 ml) and $H_2O$ (50 ml). Upon separation of the aqueous layer, the organic layer was washed with brine (3×50 ml), dried ($MgSO_4$), filtered and evaporated to give an oil which was fractionated by flash chromatography (column Ø=3 cm, h=20 cm) using as eluent hexane:EtOAc=1:4 then 1:3 to afford 0.03 g (26% yield) of a white solid, the 17-methyl-gona-1,3,5(10),13(17)-tetraen-3-O-sulfamate BLE00083A and 0.05 g (26% yield) of an uncolourless oil the 3-O-sulfamoyl-estra-1,3,5(10)-trien-17α-O-(N,N-dipentyl)sulfamate BLE00083B.

17-Methyl-gona-1,3,5(10),13(17)-tetraen-3-O-sulfamate BLE00083A.

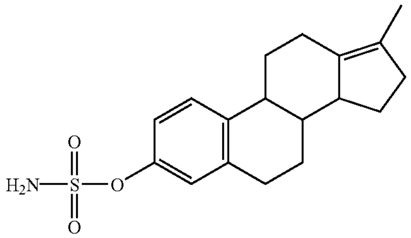

$C_{18}H_{23}NO_3S$ MW 333.45 Mp 172–176° C. $^1$H NMR 400 MHz ($CDCl_3$): 0.96–1.43 (m, 4H), 1.64 (s, 3H, C-17-$CH_3$), 1.92–2.51 (m, 8H), 2.68 (m, 1H, C-12□-H), 2.83 (m, 2H, C-6□,□-H), 4.88 (s br, 2H exch. $D_2O$, —$\underline{NH}_2$), 7.02 (d, 1H, J=2.7 Hz, C-4-H), 7.08 (dd, 1H, J=2.7 and 8.6 Hz, C-2-H) and 7.35 (d, 1H, J=8.6 Hz, C-1-H). M/S m/z (+ve FAB, rel. int.): 333.2 (100, $M^+$), 254.2 (12), 236.1 (15), 157.1 (11), 133.1 (10). HRMS (+ve FAB) m/z calcd for $C_{18}H_{23}NO_3S$ $M^+$ 333.139866. found 333.13900

| | | | | | | |
|---|---|---|---|---|---|---|
| Microanalysis Found: | % C | 64.50 | % H | 6.99 | % N | 4.13 |
| Theor. | | 64.84 | | 6.95 | | 4.20 |

Rf 0.42 (AcOEt:hexane=1:3), SM Rf 0.47

3-O-Sulfamoyl-estra-1,3,5(10)-trien-17α-O-(N,N-dipentyl)sulfamate BLE00083B.

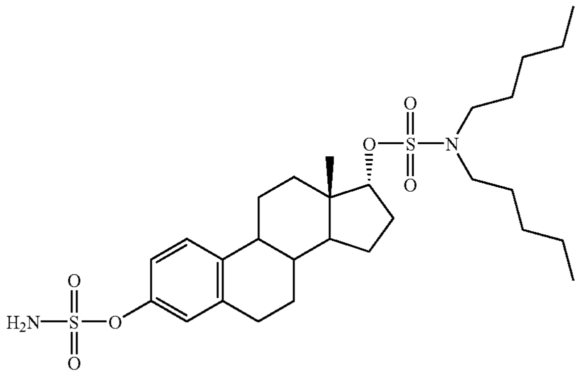

$C_{28}H_{46}N_2O_6S_2$ MW 570.80 $^1$H NMR 400 MHz ($CDCl_3$): 0.77 (s, 3H, C-18-$C\underline{H}_3$), 0.91 (t, 6H, J=7.0 Hz, 2× $\underline{CH}_3CH_2$—), 1.20–2.42 (m, 25H), 2.78–2.94 (m, 2H, C-6-H), 3.12–3.26 (m, 4H, 2×N($\underline{CH}_2$)), 4.54 (d, 1H, J=5.9 Hz, C-17□-H), 5.08 (s br, 2H exch. $D_2O$, —$\underline{NH}_2$), 7.04 (d, 1H, J=2.7 Hz, C-4-H), 7.08 (dd, 1H, J=2.7 and 8.6 Hz, C-2-H) and 7.31 (d, 1H, J=8.6 Hz, C-1-H). M/S m/z (−ve FAB, rel. int.): 569.3 [100, $(M-H)^-$], 334.2 (5), 236.2 (66), 78.0 (24). HRMS (−ve FAB) m/z calcd for $C_{28}H_{45}N_2O_6S_2$ $(M-H)^-$ 570.27191. found 569.27272 Rf 0.40 (AcOEt:hexane=1:3), SM Rf 0.47

Biological Data

Biological data were determined in accordance with the above STS Protocols and in accordance with the following Assays.

Microvessel Formation Assay

This assay is performed using the "AngioKit".

The Angiokit is a 24 well plate with HUVECs co-cultured within a bed of adult human fibroblasts in optimised medium (TCS Cellworks, UK).

The AngioKit was incubated at 37° C. with 5% $CO_2$ humidified atmosphere throughout the experiment. On Day 1 the medium was aspirated and replaced by the experimental medium (pre-equilibrated at 37° C. with 5% $CO_2$ humidified atmosphere for 30 mins) and drug dilutions made up in the warmed optimised medium. On days 4, 7 and 9 the medium was changed and fresh drugs added as on day 1. Suramin (20 μM) was used as a negative control and VEGF (2 ng/ml) as a positive control.

On day 11, cells were fixed and stained. The medium was aspirated and each well washed with 1 ml washing buffer Dulbecco's Phosphate Buffered Saline. 1 ml of 70% ethanol (−20° C.) was added to each well to fix the cells. The wells were then washed with 1 ml blocking buffer (1× wash buffer supplemented with 1% BSA (Sigma, UK)). Cells were stained for von Willebrand Factor. 0.5 ml diluted (1:200 in blocking buffer) primary antibody (sheep anti-human von Willebrand TCS cellworks, UK) was added to each well and the, plate was incubated at 37° C. for 1 hour. The wells were then washed three times with 1 ml blocking buffer before 0.5 ml diluted (1:400 in blocking buffer) secondary antibody conjugate (donkey anti-sheep IgG Horseredish Peroxidase conjugate TCS cellworks, UK) was added to each well. The plate was incubated for a further hour at 37° C. After this the wells were washed three times with distilled $H_2O$. Then 0.5 ml of 3,3'-Diamino-Benzidine tetrahydrochloride (DAB) metal substrate 1:10 in substrate buffer (TCS Cellworks, UK) were added to each well, this was incubated at 37° C. until tubules developed a dark brown colour (approx. 30 mins) The wells were then washed three times with 1 ml distilled $H_2O$ and left to air dry.

The extent of tubule formation was then scored manually by eye. A grid was drawn on the back of the plate using a fine marker pen (see FIG. 2.1). A chalkley eyepiece graticule (Pyser SGI Ltd., UK) was fitted to the microscope and low power was used to scan 24 potential counting areas (where the grid lines intersect), and the five that appear to have the most tubule formation were counted. The eyepiece has 25 spots, each spot that overlaps a tubule counts as one. This was repeated for every well.

Colchicine Displacement Assay

The protocol for this assay for tubulin binding is given below.

MES buffer (pH 6.7)+3H Colchicine (10–12 nM)

↓

Competitors (20 μM)

↓

±Tubulin (0.125 mg)

(Total assay mixture is 250 μl @ this stage)

↓

Incubation @ 37° C. for 15 min.

↓

+50 μl ice cold 5% DCC

↓

Incubation on ice for 15 min.

↓

Spin @ 5000 rpm for 5 min

↓

150 μl of the supernatant counted. (½ the total vol.)

Suitable blanks, controls are maintained at the same time and total counts added is determined.

Results

| MCF-7 cell STS assay | |
|---|---|
| 2-EtE2BisMATE | IC50-33 nM |
| **MDA Cell Proliferation assay** | |
| 2-MeOE2BisMATE | IC50-0.45□M |
| 2-EtE2BisMATE | IC50-0.32□M |

Microvessel Formation Assay (HUVECs+fibroblast co-culture)

| Compound | IC50 |
|---|---|
| 2-MeOE2MATE | 0.1 μM |
| 2-EtE2MATE | 0.07 μM |
| 2-MeOBisMATE | 0.06 μM |
| 2-EtBisMATE | <0.05 μM |

Colchicine Displacement Assay (%)

| | |
|---|---|
| Colchicine | 79 |
| 2-MeOE2 | 41 |
| 2-MeOE2MATE | 60 |
| 2-MeOE2BisMATE | 55 |
| 2-EtE2 | 6 |
| 2-EtE2MATE | 80 |
| 2-EtE2BisMATE | 60 |

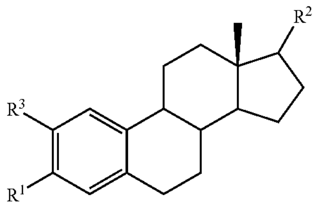

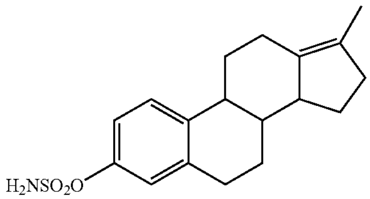

BLE00083A
BLE00086

| | | | | | T47D cell growth, % inhibition | | Placental Microcsomes % inhibition | | Plate assay % inhibition | | |
|---|---|---|---|---|---|---|---|---|---|---|---|
| $R^2$ | $R^3$ | $R^1$ | Cpd Code | STX | 10 μM | 10 nM | 1 μM | 10 nM | 0.1 μM | 1 μM | 10 μM |
| OH | H | β-$OSO_2NH_2$, α-H | BLE99031A | 48 | | | 5.1[1] | 0.5[1] | 21 | 24 | 46 |
| OH | H | β-$OSO_2$NHAc, α-H | BLE99058 | 42 | | | 7.8[1] | 0.9[1] | 4 | 1 | 20 |
| OH | H | β-$OSO_2N(Me)_2$, α-H | BLE99067 | 43 | | | 8.7[1] | −0.1[1] | −5 | −1 | 50 |
| OH | H | β-$OSO_2N(pentyl)_2$, α-H | BLE99073 | 22 | | | −11.8[2] | 1.2[2] | | | |
| OH | H | α-$OSO_2N(pentyl)_2$, β-H | BLE00082 | 23 | | | −22.0 | −28.0 | 6 | 24 | 7 |
| OH | H | β-$OSO_2N(Bn)_2$, α-H | BLE99060 | 40 | | | 1.36[2] | −3.2[2] | | | |
| OH | H | α-$OSO_2N(Bn)_2$, β-H | BLE99066 | 41 | | | 4.5[1] | 1.4[1] | 11 | 5 | 27 |
| $OSO_2NH_2$ | H | β-OH, α-H | BLE00084 | 28 | | | | | 4 | 14 | 23 |
| $OSO_2NH_2$ | H | β-$OSO_2NH_2$, α-H | BLE99031B | 49 | | | IC50 20 nM | | 7 | 12 | 32 |

-continued

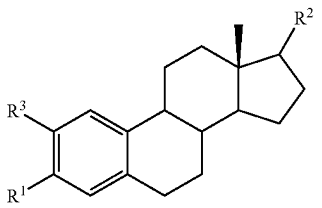

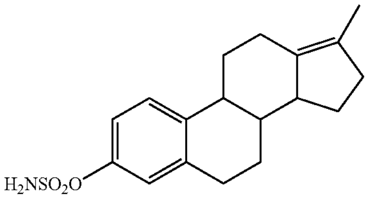

BLE00083A
BLE00086

| $R^2$ | $R^3$ | $R^1$ | Cpd Code | STX | T47D cell growth, % inhibition 10 µM | T47D cell growth, % inhibition 10 nM | Placental Microcsomes % inhibition 1 µM | Placental Microcsomes % inhibition 10 nM | Plate assay % inhibition 0.1 µM | Plate assay % inhibition 1 µM | Plate assay % inhibition 10 µM |
|---|---|---|---|---|---|---|---|---|---|---|---|
| $OSO_2NH_2$ | H | β-$OSO_2$NHAc, α-H | BLE99065 | 46 | | | 91.0[1] | 9.8[1] | 7 | 5 | 23 |
| $OSO_2NH_2$ | H | β-$OSO_2N(Me)_2$, α-H | BLE99069 | 47 | | | 96.3[1] | 30.3[1] | 3 | 10 | 73 |
| $OSO_2NH_2$ | H | β-$OSO_2$N(pentyl)$_2$, α-H | BLE99074 | | | | 23.7[2] | −9.3[2] | | | |
| $OSO_2NH_2$ | H | α-$OSO_2$N(pentyl)$_2$, β-H | BLE00083B | 25 | | | 52.5 | −9.3 | 8 | 1 | 24 |
| $OSO_2NH_2$ | H | β-$OSO_2N(Bn)_2$, α-H | BLE99063 | 44 | | | 38.2[1] | −1.9[1] | 0 | 15 | 69 |
| $OSO_2NH_2$ | H | α-$OSO_2N(Bn)_2$, β-H | BLE99068 | 45 | | | 58.2[1] | 4.9[1] | −18 | −1 | 39 |
| OH | OMe | β-OH, α-Bn | BLE01014 | 98 | | | | | −14 | −14 | ND |
| $OSO_2NH_2$ | OMe | β-OH, α-Bn | BLE01018 | 100 | | | IC50 430 nM | | −19 | −12 | ND |
| OH | OMe | β-OH, α-(4'-$^t$Bu)Bn | BLE01008 | 99 | | | | | −12 | −15 | ND |
| $OSO_2NH_2$ | OMe | β-OH, α-(4'-$^t$Bu)Bn | BLE01016 | 101 | | | IC50 4300 nM | | −14 | −10 | −3 |
| $OSO_2NH_2$ | OMe | β-$OSO_2NH_2$, α-H | | | | | IC50 32 nM | | 7 | 12 | 32 |
| $OSO_2NH_2$ | OEt | β-$OSO_2NH_2$, α-H | | | | | IC50 1 µM | | 7 | 12 | 32 |
| | | | BLE00086 | 26 | 93.2 | | | | 8 | 3 | 14 |
| | | | 2-MeOE1 | | | | | | 6 | 7 | 73 |
| | | | 2-MeOEMATE | | | | | | 15 | 42 | 88 |
| | | | 2-MeOE2 | | | | | | −2 | 19 | 66 |
| | | | 2-EtE1 | | | | | | −1 | −2 | 66 |
| | | | 2-EtEMATE | | | | | | 36 | 51 | 60 |
| | | | Taxol | | | | | | 46 | 96 | 91 |

[1]667COUMATE 1 µM 99.3, 10 nM 89.9; EMATE 1 µ98.0, 10 nM 56.1
[2]EMATE 1 µM 96.9, 10 nM 30.4-ve % means stimulation The invention will now by further described by the following numbered paragraphs:

1. A compound of Formula I

Formula I

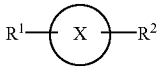

wherein:

X is a ring system;

$R^1$ is any one of a sulphamate group, a phosphonate group, a thiophosphonate group, a sulphonate group or a sulphonamide group;

$R^2$ is any one of a sulphamate group, a phosphonate group, a thiophosphonate group, a sulphonate group or a sulphonamide group;

wherein when X is a steroidal structure and both of $R^1$ and $R^2$ are sulphamate groups, the steroidal ring system (X) represents an oestrogen;

and wherein said compound is capable of inhibiting steroid sulphatase (STS) activity and/or is capable of acting as a modulator of cell cycling and/or as a modulator of apoptosis and/or as a modulator of cell growth.

2. A compound according to paragraph 1 wherein the ring system is a polycyclic system.

3. A compound according to paragraph 2 wherein the ring system is of the formula

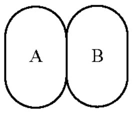

4. A compound according to paragraph 1 or 2 wherein the ring system comprises at least three rings.

5. A compound according to paragraph 4 wherein the ring system is of the formula

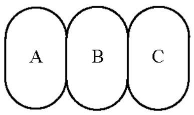

6. A compound according to paragraph 1, 2 or 3 wherein the ring system comprises at lest four rings.

7. A compound according to paragraph 6 wherein the ring system is of the formula

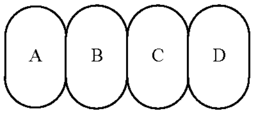

8. A compound according to any one of paragraphs 3, 5 or 7 wherein $R^1$ is attached to ring A.

9. A compound according to paragraph 3 wherein $R^2$ is attached to ring B.

10. A compound according to paragraph 5 wherein $R^2$ is attached to ring C.

11. A compound according to paragraph 6 wherein $R^2$ is attached to ring D.

12. A compound according to any one of paragraphs 1 to 11 wherein the ring system is a steroidal or mimics a steroidal ring.

13. A compound according to paragraph 12 wherein the ring system is a steroidal.

14. A compound according to paragraph 13 wherein the ring system oestrogenic.

15. A compound according to paragraph 13 wherein the ring system is an oestrogen.

16. A compound according to paragraph 15 wherein the ring system is selected from oestrone and oestradiol.

17. A compound according to any one of the preceding paragraphs wherein the compound has the Formula Ia Formula Ia

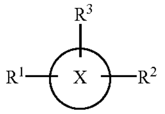

wherein $R^3$ is a hydrocarbyl or oxyhydrocarbyl group.

18. A compound according to any one of the preceding paragraphs wherein the compound has the Formula II Formula II

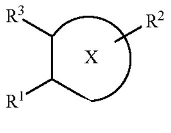

wherein $R^3$ is a hydrocarbyl or oxyhydrocarbyl group.

19. A compound according to paragraph 17 or 18 wherein $R^3$ is an oxyhydrocarbon group.

20. A compound according to paragraph 17 or 18 wherein $R^3$ is an alkoxy group.

21. A compound according to paragraph 20 wherein the alkoxy group is methoxy.

22. A compound according paragraph 17 or 18 wherein $R^3$ is an hydrocarbyl group.

23. A compound according to paragraph 22 wherein $R^3$ is an alkyl group.

24. A compound according to paragraphs 23 wherein the alkyl group is methyl or ethyl.

25. A compound according to any one of the preceding paragraphs having Formula IV Formula IV

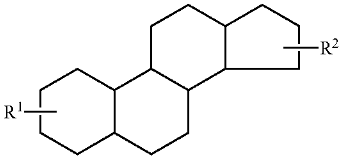

26. A compound according to any one of the preceding paragraphs having Formula V Formula V

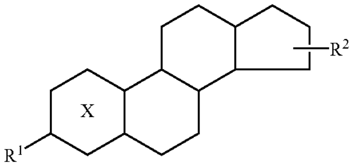

27. A compound according to any one of the preceding paragraphs having Formula VI Formula VI

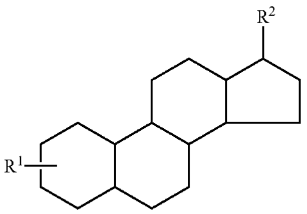

28. A compound according to any one of the preceding paragraphs having Formula VII Formula VII

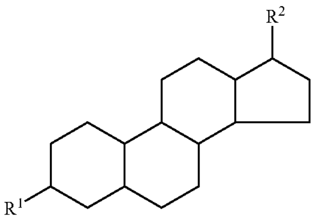

29. A compound according to any one of the preceding paragraphs wherein $R^1$ is a sulphamate group.

30. A compound according to any one of the preceding paragraphs wherein $R^2$ is a sulphamate group.

31. A compound according to any one of the preceding paragraphs wherein $R^1$ and $R^2$ are sulphamate groups.

32. A compound according to paragraph 1 wherein the compound comprises at least two sulphamate groups, wherein said sulphamate groups are not on the same ring.

33. A compound according to any one of the preceding paragraphs wherein the sulphamate group is of the formula

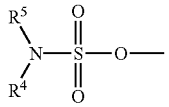

wherein each of $R^4$ and $R^5$ is independently selected from H and hydrocarbyl.

34. A compound according to paragraph 33 wherein each of $R^4$ and $R^5$ is independently selected from H, alkyl, cycloalkyl, alkenyl and aryl, or together represent alkylene optionally containing one or more hetero atoms or groups in the alkylene chain.

35. A compound according to paragraph 33 or 34 wherein at least one of $R^4$ and $R^5$ is H.

36. A compound according to paragraph 33, 34 or 35 wherein both of $R^4$ and $R^5$ are H.

37. A compound of Formula VIII

Formula VIII

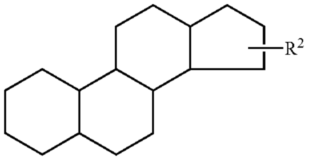

wherein:

$R^2$ is any one of a sulphamate group, a phosphonate group, a thiophosphonate group, a sulphonate group or a sulphonamide group;

and wherein said compound is capable of inhibiting steroid sulphatase (STS) activity and/or is capable of acting as a modulator of cell cycling and/or as a modulator of apoptosis and/or as a modulator of cell growth.

38. A compound according to paragraph 37 of Formula IX

Formula IX

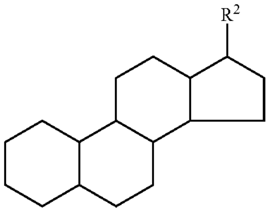

39. A compound according to paragraph 37 or 38 wherein $R^2$ is a sulphamate group.

40. A compound according to any one paragraphs 37 to 39 wherein the sulphamate group is of the formula

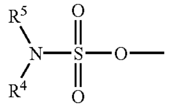

wherein each of $R^4$ and $R^5$ is independently selected from H and hydrocarbyl.

41. A compound according to paragraph 40 wherein each of $R^4$ and $R^5$ is independently selected from H, alkyl, cycloalkyl, alkenyl, C(O)alkyl, aryl, arylalkyl or together represent alkylene optionally containing one or more hetero atoms or groups in the alkylene chain.

42. A compound according to paragraph 40 or 41 wherein at least one of $R^4$ and $R^5$ is H.

43. A compound according to paragraph 40 or 41 wherein both of $R^4$ and $R^5$ are H.

44. A compound according to paragraph 40 wherein each of $R^4$ and $R^5$ is independently selected from H, $C(O)CH_3$, $(CH2)_4CH_3$, $CH_2C_6H_5$, and $CH_3$.

45. A compound according to any one of paragraph 37 to 44 of Formula X

Formula X

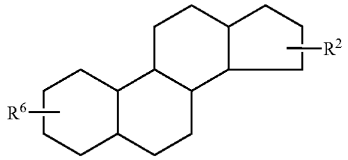

wherein $R^6$ is OH or an oxyhydrocarbyl group

46. A compound according to paragraph 37 of Formula XI

Formula XI

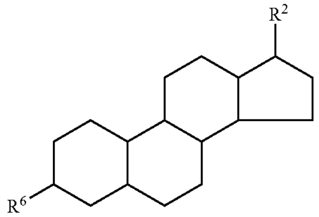

wherein $R^6$ is OH or an oxyhydrocarbyl group

47. A compound according to paragraph 45 or 46 wherein $R^6$ is an oxyhydrocarbyl group.

48. A compound according to paragraph 47 wherein the oxyhydrocarbyl group is $O(CH_2)_nC_6H_5$ wherein n is from 1 to 10, preferably 1 to 5, preferably 1, 2 or 3

49. A method comprising (a) performing a steroid sulphatase assay with one or more candidate compounds having the formula as defined in any one of the preceding paragraphs; (b) determining whether one or more of said candidate compounds is/are capable of modulating STS activity and/or cell cycling and/or cell growth and/or apoptosis; and (c) selecting one or more of said candidate compounds that is/are capable of modulating STS activity and/or cell cycling and/or cell growth and/or apoptosis.

50. A method comprising (a) performing a steroid sulphatase assay with one or more candidate compounds having the formula as defined in any one of paragraphs 1 to 48; (b) determining whether one or more of said candidate compounds is/are capable of inhibiting STS activity; and (c) selecting one or more of said candidate compounds that is/are capable of inhibiting STS activity and/or cell cycling and/or cell growth and/or apoptosis.

51. A compound identified by the method according to paragraph 49 or paragraph 50.

52. A compound according to any one of paragraphs 1 to 48 for use in medicine.

53. A pharmaceutical composition comprising the compound according to any one paragraphs 1 to 48 optionally admixed with a pharmaceutically acceptable carrier, diluent, excipient or adjuvant.

54. Use of a compound according to any one of paragraphs 1 to 48 in the manufacture of a medicament for use in the therapy of a condition or disease associated with STS and/or cell cycling and/or apoptosis and/or cell growth.

55. Use of a compound according to any one paragraphs 1 to 48 in the manufacture of a medicament for use in the therapy of a condition or disease associated with adverse STS levels and/or cell cycling and/or apoptosis and/or cell growth.

All publications and patents and patent applications mentioned in the above specification are herein incorporated by reference.

Various modifications and variations of the present invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in chemistry, biology or related fields are intended to be within the scope of the following claims.

APPENDIX A

Synthesis of Benzomate (STX232) and its carbinol derivative 4,4'-Bis-sulphamoyloxybenzophenone (LWO02141, STX232)

STX232

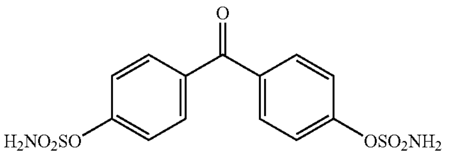

To a solution of 4,4'-dihydroxybenzophenone (1.5 g, 6.93 2 mmol) in dimethylacetamide (15 mL) at ice/water temperature was added sulphamoyl chloride in toluene (~0.69 M, 40 mL, 27.73 mmol, concentrated to ~3 ml before use). The resulting clear pale yellow mixture was stirred at room temperature under nitrogen for 3 h. At the end of this period, the reaction mixture was diluted with ethyl acetate (100 mL) and the organic layer washed with brine (100 mL, 4×50 mL), dried ($MgSO_4$), filtered and evaporated to give a creamy residue (2.5 g). To a solution of this crude in acetone (10 mL) was added chloroform dropwise (20 mL) and upon standing gave LWO02141 as fine white crystals (2.13 g, 83%); m.p. 182–185° C. [Lit. (Hatem's thesis compound number 36), 182–184° C.]; $^1H$ (400 MHz, DMSO-$d_6$) 7.47 (4H, AA'BB'), 7.85 (4H, AA'BB') and 8.24 (4H, s, exchanged with $D_2O$, $2{\times}NH_2$).

Bis-(4-sulphamoyloxyphenyl)methanol LWO02142, STX5 87)

STX587

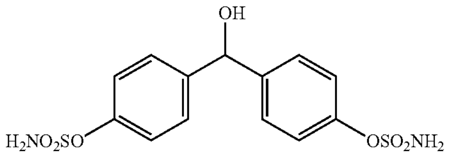

To a stirred solution of LWO02141 (500 mg, 1.343 mmol) in THF (20 mL) at ice/water was added sodium borohydride (410 mg, 10.74 mmol). The resulting milky mixture was stirred at room temperature overnight and then poured onto ice containing 5 M HCl (~8.5 mL). Ethyl acetate (100 mL) was then added and the organic layer that separated was washed with brine (100 mL, 4×50 mL), dried ($MgSO_4$), filtered and evaporated to give a clear light yellow syrup (490 mg). This crude product was fractionated on silica by flash chromatography (chloroform/ethyl acetate, 2:1 to neat ethyl acetate, gradient) and the main fraction collected upon evaporation gave LWO02142 as a sticky light brown mass which solidified to a light brown wax (377 mg, 75%) upon standing at room temperature after a few days; m.p. 135–138° C.; $R_f$ 0.36 (EtOAc/$CHCl_3$, 2:1), c.f. 0.58 (LWO02141); $\nu_{max}$ (KBr) 3740–3000, 1502, 1376, 1201, 1178, 1154 $cm^{-1}$; $^1H$ (400 MHz, DMSO-$d_6$) 5.76 (1H, d, J 3.9 Hz, reduced to s upon $D_2O$ exchange, CH), 6.05 (1H, d, J 3.9 Hz, exchanged with $D_2O$, OH), 7.21 (4H, AA'BB'), 7.46 (4H, AA'BB') and 7.95 (4H, s, exchanged with $D_2O$, $2{\times}NH_2$); LRMS (FAB+) 391.2 (25), 374.0 (8, $M^+$), 357.0 [100, $(M+H-H_2O)^+$], 295.0 [6, $(M+H-H_2NSO_2)^+$], 278.0 [15, $(M+H-H_2O-H_2NSO_2)^+$], 215.1 [6, $(M+H-2H_2NSO_2)^+$]; HRMS (FAB+) 374.02307, $C_3H_4N_2O_7S_2$ requires 374.02425. Found: C 41.7, H 3.81, N 7.35%; $C_{13}H_{14}N_2O_7S_2$ requires C 41.70, H 3.77, N 7.48%.

APPENDIX B

Synthesis, In Vitro and In Vivo Activity of Benzophenone-Based Inhibitors of Steroid Sulphatase Hatem A M Hejaz[a], Lawrence W L WOQ[a], Alan Purohit[b], Michael J Reed[b] and Barry V L Potter[a*]

[a]Department of Pharmacy and Pharmacology and Sterix Ltd., University of Bath, Bath BA2 7AY, UK

[b]Endocrinology and Metabolic Medicine and Sterix Ltd., Faculty of Medicine, Imperial College, St Mary's Hospital, London W2 iNY, UK

SUMMARY

Attempts to design and synthesise nonsteroidal E1-STS inhibitors, in the light of the potent oestrogenicity of oestrone 3-O-sulphamate (EMATE), has led to the development of 5benzophenone-4,4'-O,O-bis-sulphamate (BENZOMATE, 3) which is a significant improvement over our initial lead nonsteroidal candidates such as tetrahydronaphthalene 2-O-sulphamate and bicyclic coumarin sulphamates as a steroid sulphatase inhibitor. Although it is less potent than EMATE in vitro, BENZOMATE, a non-fused bicyclic sulphamate, is a potent inhibitor of steroid sulphatase inhibiting STS activity in intact MCF-7 breast cancer cells by >70% at 0.1 1iM and placental microsomes E1-STS by >98% at 10 µM. This agent inhibits in vivo rat liver steroid sulphatase activity by 84% and 93% 24 h after a single oral dose of 1 mg/kg and 10 mg/kg respectively. Several modifications were made to the structure of BENZOMATE. These structure-activity relationships studies conducted on BENZOMATE clearly show that its carbonyl group is pivotal for inhibition of E1-STS and that conformational flexibility is not required. BENZOMATE, with its bis-sulphamoyl moiety, therefore represents an important new class of non-steroidal steroid sulphatase inhibitor and a lead compound for future drug design.

INTRODUCTION

Since the discovery of oestrone 3-O-sulphamate (EMATE) as a highly potent irreversible inhibitor of steroid sulphatase (STS), a considerable progress has been made in developing a number of potent nonsteroidal/steroidal STS inhibitors. Those highly potent steroidal analogues reported to date include some A-ring[Purohit 1998 JSBMB] and D-ring modified[Li 1998 Steroids; Ciobanu 1999 JMC, Boivin 1999 steroids] derivatives of EMATE. As common with other steroidal compounds, many of these EMATE derivatives are potentially oestrogenic in vivo.

The primary aim for developing STS inhibitors when they were at their infancy has been for the treatment of hormone dependent breast cancer as a stand-alone agent or in conjunction with aromatase inhibitors. However, the therapeutic potentials for STS inhibitors have now been widened as recent evidence has suggested that inhibition of STS might have a clinical role in androgen-dependent skin diseases,[Hoffmann 2001 JID, Hoffmann 2000 EJD] cognitive dysfunction[Li 1995 CBR, Johnson 2000 BR] and also immune functions[Suitters 1997 Immunology]. For this reason, much emphasis has been placed on the development of non-steroidal inhibitors that either themselves, or through their metabolites, are unlikely to exert unwanted endocrinological effects.

Some impressive inhibitory activities have been observed with coumarin sulphamates especially those compounds from the tricyclic series with 667COUMATE[Woo C&B 2000] being shown to be some 3-fold more potent than EMATE against STS in a placental microsomes preparation. 667COUMATE retains all the essential features of EMATE such as oral activity and irreversible inactivation except that it lacks oestrogenic activities. Since only a non-estrogenic STS inhibitor will be of use in endocrine therapy, 667COUMATE has been selected as a Phase I trial candidate for treating hormone dependent breast cancer.

Recent work by Poirier et. al. has shown that 1-(p-sulphamoyloxyphenyl)-5-(p-tert-butylbenzyl)-5-undecanol and related congeners are highly potent STS inhibitors in vitro.[Ciobanu 2002 JSBMB] These findings support our proposed pharmacophore for STS inhibitors that the minimal structural requirement for STS inhibition is a phenol sulphamate ester and that substituents which exploit favourable hydrophobic interactions with the enzyme active site will confer higher potency to the inhibitors.[Woo 1998 JMC] In addition, our work, on coumarin sulphamates[Woo C&B 2000] and 4-nitro analogue of EMATE[Purohit 1998 JSBMB] has clearly demonstrated that sulphamoylated inhibitors that transfer more effectively their sulphamoyl group to an essential amino acid residue in the enzyme active site during the inactivation process are more potent STS inhibitors. It has been reasoned that such sulphamoyl group transfer ability of an aryl sulphamate and hence its inhibitory activity of STS are related to the leaving group ability of the parent phenol. A substantial decrease in the inhibitory activities of analogues was observed in our SAR studies on coumarin sulphamates[Woo JMC 1998] when the conjugated coumarin ring system was disrupted such as via the saturation of their C3–C4 double bond. The overall effect of these disruptions is an increase in the pKa of the resulting phenols rendering the parent coumarins a poorer leaving group and hence their sulphamates weaker inhibitors of STS.

Our initial studies to develop a nonsteroidal sulphatase inhibitor involved the sulphamoylation of diethylstilboestrol (DES), which has two non-fused aryl rings. The mono-sulphamate (1, FIG. 1) and bis-sulphamate (2, FIG. 1) derivatives of DES[Reed 1996 ERC] were considerably more potent inhibitors than the fused bicyclic tetrahydronaphthol (THIN) sulphamates.[Howarth 1994 JMC] DES-bis-sulphamate (2) was found to have an $IC_{50}$ of 10 nM as assessed in intact MCF-7 breast cancer cells.[Reed 1996 ERC, 205] Despite these encouraging results, diethyistilboestrol is a known potent oestrogen and toxic compound which would restrict the use of its bis-sulphamoylated compound in treating hormone-dependent breast cancer. However, the finding that it was not necessary to have a fused ring system for sulphatase inhibition has encouraged us to synthesise a series of sulphamate analogues with a non-fused ring structure. In addition, our prime focus is also to introduce functionalities that would increase the sulphamoyl group transfer ability of the inhibitors. We now report studies that show that benzophenone sulfamates, and their analogues, are potent inhibitors of steroid sulfatase with in vivo activity. Structural modifications to the lead inhibitor have also been made in order to understand more fully the structure-activity relationships for this class of non-steroidal STS inhibitors.

CHEMISTRY

Sulphamates derivatives of 4,4'-dihydroxybenzophenone (3–5, Scheme 1) were synthesised as follows. When 4',4-dihydroxybenzophenone in dimethylformamide (DMF) was treated with 3 equivalent of sodium hydride followed by an excess of sulphamoyl chloride, benzophenone 4',4-O,O-bis-sulphamate (3, BENZOMATE), was obtained as the major product. From the same reaction, a minor product was also isolated (7%) and it was subsequently identified as the azomethine adduct (4) which was formed between (3) and the reaction medium DMF. Similar reaction between a sulphamate and DMF in the presence of a base and the possible mechanism involved have already been observed and reported in the synthesis of 2-nitrophenol-O-sulphamate under a similar condition.[Woo JMC 1998.] When 4,4'-dihydroxybenzophenone was sulphamoylated after treating with only 1 equivalent of sodium hydride, the mono-sulphamate (4'-hydroxybenzophenone-4-O-Sulphamate 5) was obtained as the major product and its separation from the bis-sulphamate derivative (3) and the starting material, was achieved by preparative TLC.

The synthesis of compounds 6–11, 14–16 and 20–21 (FIG. 2) were achieved by sulphamoylating the corresponding commercially available parent phenols in the usual manner and where applicable, the bis- and mono-sulphamates were separated by flash chromatography.

Benzo[b]naphtho[2,3-d]-furan-6,11-dione-3-O-sulphamate (13, Scheme 2) was prepared from the parent compound 12 which was obtained by reacting 2,3-dichloro-1,4-naphthoquinone with resorcinol in ethanolic sodium ethoxide solution.[Cheng 1993 JMC]

The 4',4-dihydroxydiphenylmethane (17, Scheme 3) was prepared by catalytic hydrogenation of a solution of 4',4-dihydroxybenzophenone in ethanol in the presence of Pd-C (10%) at RT at balloon pressure for 6 h.[Levine 1957 JOC]

Suiphamoylation of 17 (Scheme 3) in the usual manner gave a mixture of 18 and 19 which were separated by flash chromatography.

For the preparation of 25 (Scheme 4), 4',4-dihydroxybenzophenone was first protected by two tert-butyldimethylsilyl (TBDMS) groups to give the disilylated 22, which was reacted with cyclohexyl magnesium chloride to give the substituted benzhydrol 23. The TBDMS groups of 23 were cleaved by tetrabutylammonium fluoride (TBAF) in THF to give the tri-hydroxylated parent compound 24 which, as a solution in dichloromethane, was sulphamoylated by reacting with sulphamoyl chloride in the presence of 2,6-di-tert-butyl-4-methylpyridine (DBMP) to give 25. The $^1$H NMR of 25 has shown a downfield shift for the C3, C3', C5 and C5' protons in comparison with those of 24 which is indicative of the presence of sulphamate group at both the 4 and 4'-position. The fact that 25 was isolated as the main product has strongly suggested that the tertiary alcohol has not been sulphamoylated as anticipated in the conditions adopted because of steric hindrance and the use of only a weak base.

Nitration of benzophenone with a mixture of nitric acid and sulphuric acid gave 3',3-dinitrobenzophenone in 53% yield (26, Scheme 5). Reduction of 26 with stannous chloride in HCl followed by hydroxydeamination of the crude salt by sodium nitrite in sulphuric acid gave 3',3-dihydroxybenzophenone 27.[Klemm 1958 JACS] Sulphamoylation of 27 gave a mixture of the corresponding bis-(28) and mono-(29) sulphamate (Scheme 5).

RESULTS AND DISCUSSION

Our earlier programme of developing new classes of nonsteroidal STS inhibitors has identified that the mono- (1, FIG. 1) and bis-sulphamate (2, FIG. 1) derivatives of diethylstilboestrol (DES) were moderate STS inhibitors. These findings have indicated that it is not necessary to have a fused ring system for STS inhibition. Although the reason for the inhibitory activities observed for sulphamate derivatives of DES is not clear, it is possible that their conjugated stilbene system facilitates the inactivation of STS via sulphamoylation. Because of the toxicities associated with diethylstilboestrol which rules out further modifications to the structure for enhancing potency, we replaced instead the alkene moiety of this class of compounds with a carbonyl group to produce the sulphamate derivatives of 4,4'-dihydroxybenzophenone. The mesomeric effect of the benzophenone system is expected to lower the pKa of the bis-phenol rendering their sulphamate a more effective sulphamoyl group transferring agent. Indeed, the pKa of 4,4'-dihydroxybenzophenone in a solution of 50% v/v aqueous methanol as determined by potentiometric titration was found to be 9.11±0.24. In contrast, a pKa value of 10.96±0.13 (c.f. 11.22, 48% v/v aq. Ethanol[Meyers JACS 1962]) was obtained under the same conditions for its unconjugated congener, bis-(4-hydroxyphenyl)methane. These observations have prompted us to investigate if sulphamate derivatives of 4,4'-dihydroxybenzophenone will also show high potency against STS since these compounds should have a better sulphamoyl group transferring potential.

The inhibitions of oestrone sulphatase (E1-STS) activity in intact MCF-7 breast cancer cells and in a placental microsomes preparation by sulphamates 3–5 were tabulated in Table 1 and Table 2 respectively. The best compound in this series has been BENZOMATE (3) which showed >70% inhibition of STS activity in intact MCF-7 breast cancer cells at 0.1 μM and >98% inhibition of placental microsomes E1-STS at 10 μM. The other members of the series were slightly less potent than 3 suggesting that a sulphamate group at both the 4- and 4'-positions of benzophenone are required for maximising the inhibitory activity for this type of non-steroidal STS inhibitor. We have observed that the azomethine adduct of 667COUMATE is inactive as an STS inhibitor (unpublished result). By the same token, the STS inhibitory activity observed for compound 4 is anticipated to be primarily the result of its mono-sulphamate group inactivating the enzyme via a sulphamoyl transfer.

Having identified 3 as a potent E1-STS inhibitor, we prepared a range of compounds in order to establish the structure-activity relationships for this compound. These analogues include benzophenone-4-O-sulphamate where one of the two phenyl rings has not been substituted (6, FIG. 2); chalcone sulphamates (7 and 8, FIG. 2) where the distance between the two non-fused-rings has been extended; dibenzofuran-2-O-sulphamate (9, FIG. 2), 2,6-anthraquinone bis- (10, FIG. 2) and mono-(11) sulphamate and benzo[b]naphtho[2,3 -d]furan-6,11-dione-3-O-sulphamate (13, Scheme 2) where the molecules have been conformationally restricted; sulphonyldiphenyl-4',4-O,O-bis-sulphamate (14, FIG. 2), and thiodiphenyl bis- (15, FIG. 2) and mono-(16) sulphamate where the carbonyl group has been replaced by other functionalities; diphenylmethane 4,4'-O,O-bissulphamate (18, Scheme 3) and 4'-hydroxy-diphenylmethane 4-O-sulphamate (19, Scheme 3) where the carbonyl group has been removed; (1,3-adamantanediyl) diphenyl bis-(20, FIG. 2) and mono-(21) sulphamate, and 1-cyclohexyl-1,1-(4',4-bis-sulphamoyloxyphenyl)methanol (25, Scheme 4) where an extra ring (aliphatic and aromatic) has been introduced; benzophenone 3,3'-O,O-bis-sulphamate (28, Scheme 5) and 3'-hydroxybenzophenone-3-O-sulphamate (29, Scheme 5) where the sulpharnate group(s) have been relocated.

Upon examination of the abilities of these BENZOMATE analogues (6–11, 13–16, 18–21, 25, and 28–29 to inhibit E1-STS activity (Tables 1 and 2), almost all of them were found to be less effective inhibitors of E1-STS than BENZOMATE, with the exception of the sulphamate derivatives (10 and 11) of 2,6-anthraquinone and benzophenone-3',3-bis-sulphamate 28, which were found to inhibit the E1-STS activity stronger than or to a similar extent to BENZOMATE in MCF-7 breast cancer cells. Although compounds 10 and 11 were again found to be of similar potencies to BENZOMATE as E1-STS inhibitors in the placental microsomes preparation, compound 28 was clearly less potent in this enzyme system. This finding has provided further evidence to support our reasoning that BENZOMATE is a highly potent E1-STS inhibitor because of a more efficient sulphamoyl group transfer by its sulphamate groups in the presence of the carbonyl group in a position para to them. Such effect would have been diminished by the relocation of its sulphamate groups to the 3,3'-position as in 28 rendering the compound a weaker E1-STS inhibitor.

The in vitro results here also show a general pattern that compounds which poorly inhibit E1-STS activity in intact MCF-7 breast cancer cells (Table 1) also perform poorly when examined in placental microsomes (Table 2). In addition, the bis-sulphamates of compounds are in general more potent than their corresponding mono-sulphamates, e.g. 3 vs 5 and 6, 15 vs 16 and 18 vs 19. Although it is still unclear why such pattern exists, this further demonstrates that the sulphamate group is the key chemical structural requirement for potent sulphatase inhibition.

The sulphamate derivatives (7 and 8) of chalcone are analogues of compound 6 where the distance between the two non-fused-phenyl rings has been extended without disrupting the conjugation between the ring system bearing the sulphamate and the carbonyl group. The weak inhibitions observed for 7 and 8 have shown the importance of the benzophenone scaffold for the biological activities of BENZOMATE.

Replacement of the carbonyl group of BENZOMATE by methylene (18) or the whole carbonyl group by divalent sulphur (15) or a sulphonyl group (14) or aliphatic rings (20) or substitution with a cyclohexyl ring (25) significantly reduces the inhibitory activity of the sulphamate. Since, the carbonyl group of BEZOMATE is clearly required for potent activity, this might be to do with extra binding to the enzyme active site or conjugation with the phenyl ring with activation of the sulphamate group. Substituting the carbonyl group with a bulky ring (adamantanediyl, 20, cyclohexyl 25) abolishes the inhibitory activities of the BENZOMATE. These results therefore highlight the presumed limited tolerance of the enzyme to these bulky rings. It is possible that these rings may shift the sulphamate groups at the 4 and 4'-positions away from the position occupied by the sulphamate groups of BENZOMATE in the binding site, and hence the analogue might not be activated effectively for the sulphamoylation of the enzyme. These rings may also conceivably shield any sulphamate proton abstraction, and thus the first vital step proposed for the mechanism of E1-STS inhibition by EMATE,[Woo 2000 C&B] is prevented from occurring. These rings may of course simply be so large, that the molecule cannot fit into the enzyme active site.

The anthraquinone derivatives and 3-hydroxybenzo[b]naphtho[2,3-d]furan-6,11-dione (12) are intercalating cytostatic agents and have anti-tumour properties. However, we considered that introduction of the sulphamate group (the key chemical structural requirement for potent sulphatase inhibition) into the structure of these compounds, might significantly engender sulphatase inhibitory activity and, might provide new leads for sulphatase inhibitors. Additionally, anthraquinones could serve as conformationally restricted analogue of BENZOMATE, to explore details of the potential active binding mode. The corresponding sulphamates (10, 11 and 13) of these compounds have been prepared and examined in MCF-7 cells and placental microsomes for E1-STS inhibition. They were found to be potent sulphatase inhibitors (Tables 1 and 2). The bis- (10) and mono-(11) sulphamates of anthraquinone were found to inhibit E1-STS activity in MCF-7 cells by 93% and >99% at 0.1 μM respectively (Table 1) and in placental microsomes by 91% and 86% at 10 μM respectively (Table 2). Therefore, it is reasoned that the conformationally restricted analogues of BENZOMATE (anthraquinones) possess similar E1-STS inhibitory activity. It has been observed that 3-O-sulphamoyl-benzo[b]naphtho[2,3-d]furan-6,11-dione (13) also kills the MCF-7 cells, indicating that these derivatives might be toxic and have additional activities. The question arises whether their inhibition of E1-STS sulphatase results from the sulphamoyl group alone or is due to their other properties. This remains to be elucidated precisely, but the following observation was noted: the corresponding starting material of 13 has no inhibitory activity against E1-STS when examined in MCF-7 cells at 10, μM (inhibited E1-STS by 3%) while 13 inhibited E1-STS by 99% at the same concentration. When the percentage growth inhibition of MCF-7 breast cancer cells by 12 was examined, it was found to be 12%, 20% and 56% at 0.1 μM, 1 μM and 10 μM respectively compared to 13 which inhibited the growth of these cells by 41% and 44% at 1 μM and 10 μM respectively and was inactive at 0.1 μM, indicating that both the phenol (12) and the corresponding sulphamate (13) have the same property of inhibition of the growth of MCF-7 breast cancer cells.

Having identified that benzophenone-4',4-bis-sulphamate (BENZOMATE, Scheme 1, 3) is a potent inhibitor, BENZOMATE was tested in vivo in rats. Twenty-four hours after a single oral dose at 1 mg and 10 mg/kg, the liver E1-STS activity was found to be inhibited by 84% and 93% respectively, demonstrating that BENZOMATE is orally active and a highly potent non-steroidal inhibitor in vivo (FIG. 3).

CONCLUSIONS

Attempts to design and synthesise nonsteroidal E1-STS inhibitors, in the light of the potent oestrogenicity of EMATE, has led primarily to the development of BENZOMATE (3), a significant improvement over our initial lead nonsteroidal candidates such as THN 2-O-sulphamate and bicyclic coumarin sulphamates. BENZOMATE, a non-fused bicyclic sulphamate, is a potent inhibitor of steroid sulphatase, albeit less potent than EMATE in vitro. This agent inhibits in vivo rat liver steroid sulphatase activity by 84% and 93% respectively at a single oral dose (1 mg/kg and 10 mg/kg). Several modifications were made to the structure of BENZOMATE. These structure-activity relationships studies conducted on BENZOMATE clearly show that its carbonyl group is pivotal for inhibition of E1-STS and that conformational flexibility is not required. A structurally modified BENZOMATE with highly potent activity might subsequently be designed and developed for therapeutic use in the treatment of hormone-dependent breast cancer and this compound, with its bis-sulphamoyl moiety represents an important new class of inhibitor and lead compound for the future. A recent report confirms this conclusion.[Nussbaumer 2002 BMCL]

Experimental

All reagents and solvents employed were of general purpose or analytical grade unless otherwise stated, and purchased from either Aldrich or Sigma Chemicals or Lancaster Synthesis.

Silica gel refers to silica gel, Merck, grade 60. Product(s) and starting material were detected either viewing under UV light or treating with a methanolic solution of phosphomolybic acid followed by heating. NMR spectra were determined using acetone-$d_6$, $CDCl_3$ or DMSO-$d_6$ as solvent and TMS as internal standard, unless otherwise stated. The $^1H$ NMR and $^{13}C$ NMR spectra were recorded on a Jeol GX 270 at 270 MHz and on a Jeol EX 400 at 400 MHz NMR spectrometer. The following abbreviations are used to describe resonances in $^1H$ NMR and $^{13}C$ NMR spectra: s, singlet; d, doublet; br, broad; t, triplet; q, quartet; m, multiplet and combination such as dd, doublet of doublets. IR spectra were determined as KBr discs, using a Perkin-Elmer 782 Infra-Red Spectrophotometer. Melting points were determined on a Reichert-Jung Kofler Block and are uncorrected. Mass spectra were recorded on VG 7070 and VG Autospec instruments at the Mass Spectrometry Service at the University of Bath. FAB-mass spectra were carried out using m-nitrobenzyl alcohol (m-NBA) as the matrix. CHN analysis was determined using gas chromatography at the Microanalysis Service at the University of Bath.

All reagents and solvents used were stored away from moisture and light and dried before use. Low temperature experiments were conducted using a well insulated external bath containing either ice/water with NaCl for 0° C. or carbon dioxide pellets with acetone or using cold plate. Experiments requiring anhydrous conditions were guarded by mean of a drying tube containing self-indicating silica. Evaporation of solvents was carried out with a rotary evaporator at reduced pressure (water pump) and on stated occasions, followed by the use of a high vacuum pump. Samples were dried in drying tube under high vacuum and low temperature. A solution of sulphamoyl chloride in toluene was prepared from chlorosulphonyl isocyanate and formic acid according to the method described in ref.[Woo Heteroatom JSHMB] An appropriate volume of this solution was concentrated freshly before use.

pKa Determination of 4,4'-dihydroxybenzophenone and bis-(4-hydroxyphenyl)methane A 5 mM solution of 4,4'-dihydroxybenzophenone or bis-(4-hydroxyphenyl)methane in water/methanol (1:1) at room temperature was prepared and its pH read (WPA Linton Cambridge UK, CCMD625 pH meter). The titrant (50 mM KOH) was then added in equal portions. The pH was recorded after each addition when equilibrium has been reached (after stirring). The pKa was determined according to the procedure of Albert and Serjeant.[ref]

Biological assay of sulphainates

In vitro sulphatase inhibition was assessed using placental microsomes (100,000 g) preparations or in intact MCF-7 breast cancer cells as described previously.[Duncan 1993 CR, Howarth 1994 JMC]

For in vivo studies, female Wistar rats (Harlan Olac, Bicester, Oxon, United Kingdom) were used. Groups of rats, with three rats in each group for each experiment, were treated p.o. with vehicle (propylene glycol) or drug (1 mg and 10 mg/kg) with animals receiving a single dose. Animals were killed, using an approved procedure, 24 h after drug administration to assess the extent of steroid sulphatase inhibition. For this, samples of liver tissue were removed and immediately frozen on solid carbon dioxide and stored at −20° C. until assayed.

General method for sulphamoylation

Starting with the parent compound, the sulphamate derivatives were prepared essentially as previously described,[Woo 1996 JSBMB] unless stated otherwise, In this regard, a solution of the appropriate parent compound in anhydrous DMF was treated with sodium hydride [60% dispersion; 1.2 and 2.5 equiv. for monohydroxyl and dihydroxyl compounds respectively, unless stated otherwise] at 0° C. under an atmosphere of $N_2$. After evolution of hydrogen had ceased, a freshly concentrated solution of sulphamoyl chloride in toluene [excess, ca. 5–6 eq.] was added and the reaction mixture poured into brine after warming to room temperature overnight. Ethyl acetate was added and the organic fraction that separated was washed exhaustively with brine, dried ($MgSO_4$), filtered and evaporated under reduced pressure. In general, the crude product obtained was purified by flash chromatography or preparative TLC followed by recrystallisation to give the corresponding sulphamate. All the compounds were characterised by spectroscopic and combustion analysis.

Synthesis of Sulphamates

Benzophenone-4,4'-O,O-bis-sulphamate (3) and azomethine derivative (4)

Upon sulphamoylation, 4,4'-dihydroxybenzophenone (1.0 g, 4.668 mmol) gave a crude product (1.63 g) which was fractionated by flash chromatography (chloroform/acetone gradient). The band at Rf 0.46 (chloroform/acetone, 2:1) that collected gave a creamy residue (1.17 g) which was further purified by recrystallization from acetone/chloroform (1:2) to give 3 as white crystals (730 mg, 43%); mp 182–184° C.; $\nu_{max}$ (KBr) 3340 ($NH_2$), 1660 (C═O), 1370 ($SO_2$) $cm^{-1}$; $\delta_H$ (270 MHz, acetone-$d_6$) 7.36 (4H, br s, exchanged with $D_2O$, $2\times OSO_2NH_2$), 7.51 (4H, d, J=8.8 Hz, C-3-H, C-3'-H, C-5-H and C-5'-H), and 7.9 (4H, d, J=8.4 Hz, C-2-H, C-2'-H, C-6-H and C-6'-H); MS m/z (FAB+) 372.9 [100, $(M+H)^+$], 293.0 [30, $(M+H—SO_2NH_2)^+$], 213.1 [10, $(M+H—2\times SO_2NH_2)^+$]; MS m/z (FAB−) 370.9 [100, $(M—H)^-$], 291.9 [82, $(M—SO_2NH_2)$], 213.0 [20, $(M+H—2\times SO_2NH_2)^-$]; Acc. MS (FAB+) 373.0177 $C_{13}H_{13}N_2O_7S_2$ requires 373.0164. Found C, 41.9; H, 324; N, 7.50; $C_{13}H_{12}N_2O_7S_2$ requires C, 41.93; H, 3.25; N, 7.52%.

The band at Rf 0.57 (chloroform/acetone, 2:1) that collected gave a beige residue (183 mg) which was further purified by recrystallization from acetone/hexane (1:2) to give 4 as white crystals (130 mg, 7%); mp 158–160° C.; $\nu_{max}$ (KBr) 3340–3240 ($NH_2$), 1650 (C═O), 1370 ($SO_2$) $cm^{-1}$; $\delta_H$ (270 MHz, acetone-$d_6$) 3.09 (3H, s, —N—$CH_3$), 3.3 (3H, s, —N—$CH_3$), 7.36 (2H, br s, exchanged with $D_2O$, $OSO_2NH_2$), 7.48 (2H, d, J=8.79 Hz, C-3-H and C-5-H or C-3'-H and C-5'-H), 7.52 (2H, d, J=8.8 Hz, C-3-H and C-5-H or C-3'-H and C-5'-H) 7.82 (2H, d, J=8.8 Hz, C-2-H and C-6-H or C-2'-H and C-6'-H), 7.84 (2H, d, J=8.8 Hz, C-2-H and C-6-H or C-2'-H and C-6'-H), and 8.14 (1H, s, $SO_2N$═CH—); MS m/z (FAB+) 427.9 [100, $(M+H)^+$], 349.0 [20, $(M+H—SO_2NH)^+$], 294.1 [10, (M+2H—$SO_2N$═CH—$N(Me)_2)^+$]; MS m/z (FAB−) 425.9 [100, $(M—H^-]$, 347.0 [40, $(M—SO_2NH_2)^-$], 293.0 [10, (M+H—$SO_2$═CH—$N(Me)_2)$]; Acc. Ms (FAB+) 428.0582 $C_{16}H_{18}N_3O_7S_2$ requires 428.0586.

4'-Hydroxybenzophenone-4-O-sulphamate (5)

Upon sulphamoylation using 1 eq. of NaH, 4,4'-dihydroxybenzophenone (300 mg, 1.400 mmol) gave a crude product (420 mg) of which 100 mg was fractionated on preparative TLC (chloroform/acetone gradient). The white residue that isolated (46 mg) was further purified by recrystallization from ethyl acetate/hexane (1:2) to give 5 as white crystals (32 mg, 32%); mp >152° C. (dec.); TLC (chloroform/acetone, 4:1 and 2:1): Rfs 0.27 and 0.41 respectively; $\nu_{max}$ (KBr) 3500–3000 ($NH_2$ and OH), 1630 (C═O), 1590, 1380 ($SO_2$) $cm^{-1}$, $\delta_H$ (270 MHz, acetone-$d_6$) 7.0 (2H, d, J=8.8 Hz, C-3'-H, and C-5'-H), 7.3 (2H, br s, exchanged with $D_2O$, $OSO_2NH_2$), 7.48 (2H, d, J=8.4 Hz, C-3-H, and C-5-H), 7.77 (2H, d, J=8.4 Hz, C-2-H and C-2'-H or C-6-H and C-6'-H), 7.8 (2H, d, J=8.42 Hz, C-2H and C-2'-H or C-6-H and C-6'-H) and 8.1 (1H, br s, exchanged with $D_2O$, C-4'-OH); MS m/z (FAB+) 447.1 [10, $(M+H+NBA)^+$], 294.0 [100, $(M+H)^+$], 215.1 [10, $(M+H—SO_2NH)^+$]; MS m/z (FAB−) 446.1 [20, $(M+NBA)^-$], 292.1 [100, $(M—H)^-$], 213.1 [30, $(M—SO_2NH_2)^-$]. Found C, 53.1; H, 3.9; N, 4.55; $C_{13}H_{11}NO_5S$ requires C, 53.24; H, 3.78; N, 4.78%.

Benzophenone-4-O-sulphamate (6)

Upon sulphamoylation, 4-hydroxybenzophenone (1.0 g, 5.045 mmol) gave a crude product (1.45 g) which was fractionated by flash chromatography (chloroform/acetone, 8:1). The creamy residue that isolated (716 mg) was further purified by recrystallization from ethyl acetate/hexane (1:2) to give 6 as white crystals (495 mg, 35%); mp 134–136° C.; TLC (chloroform/acetone, 4:1 and 8:1): Rfs 0.68 and 0.35 respectively; $\nu_{max}$ (KBr) 3360 ($NH_2$), 1390 ($SO_2$) $cm^{-1}$; $\delta_H$ (270 MHz acetone-$d_6$) 7.35 (2H, hr s, exchanged with $D_2O$, $SO_2NH_2$), 7.5 (2H, d, J=8.8 Hz, C-3-H and C-5-H), 7.55–7.75 (3H, m, C-3'-H, C-4'-H and C-5'-H), 7.84 (2H, m, C-2'-H and C-6'-H), 7.88 (2H, d, J=8.8 Hz, C-2-H and C-6-H); MS m/z (FAB+) 278.0 [100, $(M+H)^+$], 198.0 [10, $(MH+H—SO_2NH_2)^+$]; MS m/z (FAB−) 430.0 [15, $(M+NBA)^-$], 276.0 [100, $(M—H)^-$], 197.0 [25, $(M—SO_2NH_2)^-$]; Acc. MS m/z (FAB+) 278.0503 $C_{13}H_{12}NO_4S$ 278.0487 requires. Found C, 56.1; H, 4.01; N, 5.12; $C_{13}H_{11}NO_4S$ requires C, 56.31; H, 4.0; N, 5.05%.

Chalcone-4-O-sulphamate (7)

Upon sulphamoylation, 4-hydroxychalcone (1.0 g, 4.46 mmol) gave a crude product (1.44 g) which was fractionated by flash chromatography (chloroform/acetone, 8:1). The creamy residue that obtained (719 mg) was further purified by recrystallization from ethyl acetate/hexane (1:2) to give 7 as white crystals (464 mg, 34%); mp 136–138° C; TLC (choroform/acetone, 8:1, 4:1 and 2:1): Rfs 0.24, 0.48 and 0.66 respectively; $\nu_{max}$ (KBr) 3500–3220 ($NH_2$), 1670 (C═O), 1390 ($SO_2$) $cm^{-1}$; $\delta_H$ (270 MHz, acetone-$d_6$) 7.27 (2H, s, exchanged with $D_2$, $OSO_2NH_2$), 7.42 (2H, d, J=8.79 Hz, C-3-H and C-5-H), 7.62 (2H, m, C-3'-H C-4'-H and C-5'-H), 7.85 (2H, d, J=14.7 Hz, CH═CH), 7.95 (5H, d, J=6.2 Hz, C-2-H and C-6-H) and 8.18 (2H, d, J=7.7 Hz, C-2'-H and C-6'-H); MS m/z (FAB+) 304.0 [100, $(M+H)^+$], 224.1 [10, $(M+H-SO_2NH_2)^+$]; MS m/z (FAB−) 302.0 [100, $(M-H)^-$], 223.0 [40, $(M-SO_2NH_2)$]; Acc. MS (FAB+) 304.0646 $C_{15}H_{14}NO_4S$ requires 304.0644. Found C, 59.1; H, 4.29; N, 4.64 $C_{15}H_{13}NO_4S$ requires C, 59.40; H, 4.32; N, 4.62%.

Chalcone-4'-O-sulphamate (8)

Upon sulphamoylation, 4'-hydroxychalcone (1.0 g, 4.46 mmol) gave a crude product (1.5 g) which was fractionated by flash chromatography (chloroform/acetone, 8:1). The creamy residue that obtained (723 mg) was further purified by recrystallization from ethyl acetate/hexane (1:2) to give 8 as white crystals (425 mg, 3 1%); mp 187–189° C.; TLC (chloroform/acetone, 8:1, 4:1 and 2:1): Rfs 0.17, 0.26 and 0.62 respectively; $\nu_{max}$ (KiBr) 3340 ($NH_2$), 1660 (C═O), 1390 ($SO_2$)$cm^{-1}$; $\delta_H$ (270 MHz, acetone-$d_6$) 7.34 (2H, s, exchanged with $D_2O$, $OSO_2NH_2$), 7.49 (5H, m, C-3', 5', 3, 4 and C-5-H), 7.88 (4H, m, CH═CH and C-2-H C-6-H), 8.25 (2H, d, J=8.8 Hz, C-2'-H and C-6'-H); MS m/z (FAB+) 304.0 [100, $(M+H)^+$], 225.1 [10, $(M+2H-SO_2NH_2)^+$]; MS m/z (FAB−) 302.0 [100, $(M-H)^-$], 223.1 [35, $(M-SO_2NH_2)^-$]; Acc. MS (FAB+) 304.0654 $C_{15}H_{14}NOS_4S$ requires 304.0644. Found C, 59.1; H, 4.29; N, 4.65; $C_{15}H_{13}NO_4S$ requires C, 59.40; H, 4.32; N, 4.62%.

Dibenzofuran-2-O-sulphamate (9)

Upon sulphamoylation, 2-hydroxydibenzofuran (1.0 g, 5.429 mmol) gave a crude product (1.31 g) which was fractionated by flash chromatography (chloroform/acetone, 8:1). The beige residue that obtained (561 mg) was further purified by recrystallization from ethyl acetate/hexane (1:2) to give 9 as white crystals (319 mg, 23%); mp>120° C. (dec.); TLC (chloroform/acetone, 8:1, 4:1 and 2:1): Rfs 0.31, 0.55 and 0.70 respectively; $\nu_{max}$ (KBr) 3400 ($NH_2$), 1600 (C═O), 1370 ($SO_2$) $cm^{-1}$; $\delta_H$ (270 MHz, acetone-$d_6$) 7.18 (2H, br s, exchanged with $D_2O$, $SO_2NH_2$), 7.46 (2H, m, C-4-H and C-5-H), 7.56 (1H, t, J=7.7 Hz, C-7-H), 7.7 (2H, t, J=7.3 Hz C-3-H and C-6-H), 8.07 (1H, d, J=2.2 Hz, C-1-H) and 8.16 (1H, d, J=7.7 Hz ,C-8-H); MS m/z (FAB+) 417.0 [13, $(M+H+NBA)^+$], 263.1 [100, $(M)^+$], 183.1 [60, $(M-SO_2NH_2)^+$]; MS m/z (FAB−) 416.0 [15, $(M+NBA)^-$], 262.0 [100, $(M-H)^-$]. Found C, 54.6; H, 3.46; N, 5.22; $C_{12}H_9NO_4S$ requires C, 54.75; H, 3.42; N, 5.32%.

Anthraquinone-2,6-O,O-bis-sulphamate (10) 2-hydroxyanthraquinone-6-O-sulphamate (11)

Upon sulphamoylation, 2,6-dihydroxyanthraquinone (1.0 g, 4.163 mmol) gave the crude products (1.41 g) of which a 100 mg sample was fractionated on preparative TLC (chloroform/acetone, gradient). The fraction at Rf 0.39 ($CH_3Cl$/acetone, 2:1) gave a yellow residue (32 mg) which was further purified by recrystallization from acetone/hexane (1:2) to give 10 as yellow crystals (24 mg, 20%); mp>220° C. (dec); TLC (chloroform/acetone, 4:1): Rf 0.26; $\nu_{max}$ (KBr) 3380–3260 ($NH_2$), 1680 (C═O), 1390 ($SO_2$) $cm^-$; $\delta_H$ (270 MHz, acetone-$d_6$) 7.57 (4H, br s, exchanged with $D_2O$, $2\times SO_2NH_2$), 7.84 (2H, dd, $J_{C-1-H,\ C-3-H}$=$J_{C-5-H,\ C-7-H}$=2.4 Hz and $J_{C-4-H,\ C-3-H}$=$J_{C-8-H,\ C-7-H}$=8.4,Hz C-3-H Hand C-7-H), 8.17 (2H, d, $J_{C-3-H,\ C-1-H}$=$J_{C-7-H,\ C-5H}$=2.6 Hz, C-1-H and C-5-H) and 8.39 (2H, d, $J_{C-3-H,\ C-4-11}$=$J_{C-7-H,\ C-8-H}$=8.4 Hz, C-4H and C-8-H); MS mz (FAB+) 398.0 [40, $(M)^+$], 240.1 [30, $(M-2\times SO_2NH)^+$]; MS m/z (FAB−) 551.1 [25, (M+NBA)], 398.1 [100, $(M)^-$], 239.1 [70, $(M+H-2\times SO_2NH_2)^-$]; Acc. MS m/z (FAB+) 397.98868 $C_{14}H_{10}N_2O_8S_2$ requires 397.98786.

The fraction at Rf 0.46 ($CH_3Cl$/acetone, 2:1) gave a white residue (46 mg) which was further purified by recrystallization from ethyl acetate/hexane (1:2) to give 11 as white crystals (31 mg, 21%); mp>285° C. (dec); TLC (chloroform/acetone, 4:1): Rf 0.3; $\nu_{max}$ (KBr) 3500–3000 (OH, $NH_2$), 1670 (C═O) and 1390 ($SO_2$) $cm^{-1}$; $\delta_H$ (270 MHz, acetone-$d_6$) 7.34 (1H, dd, $J_{C-1-H,\ C-3-H}$=2.57 Hz and $J_{C-4-H,\ C-3-H}$=8.43 Hz, C-3-H), 7.53 (2H, hr s, exchanged with $D_2O$, C-6-$SO_2NH_2$), 7.65 (1H, d, $J_{C-3-H,\ C-1-H}$=2.6 Hz, C-1-H), 7.77 (1H, dd, $J_{C-5-H,\ C-7-H}$=2.4 hz and $J_{C-8-H,\ C-7-H}$=8.43 Hz, C-7-H), 8.13 (1H, d, $J_{C-7-H,\ C-5-H}$=2.6 Hz, C-5-H), 8.2 (1H, d, $J_{C-3-H,\ C-4-H}$=8.4 Hz, C-4-H), 8.33 (1H, d, $J_{C-7-H,\ C-8-H}$=8.42 Hz, C-8-H) and 9.98 (1H, s, exchanged with $D_2O$, C-2-OH); m/z (FAB+) 320.0 [100, $(M+H)^1$], 240.1 [30, $(M+H-SO_2NH_2)$], 225.1 (15); MS m/z (FAB−) 473.2 [20, $(M+H+NBA)^-$], 318.1 [100, $(M-H)^-$], 239.1 [0-, $(M-SO_2NH_2)^-$]; Acc. MS (FAB+) 320.02236 $C_{14}H_{10}NO_6S$ requires 320.02288. Found C, 52.5; H, 2.84; N, 4.25; $C_{14}H_9NO_6S$ requires C, 52.67; H, 2.84; N, 4.39%.

3-Hydroxybenzo[b]naphtho[2,3-d]furan-6,11-dione (12)

Resorcinol (6.6 g, 60 mmol) in ethanol (80 mL) was added dropwise to a stirred ethanolic sodium ethoxide solution (prepared by dissolving 3.8 g of sodium metal in 120 mL of absolute ethanol) containing 2,3-dichloro-1,4-naphthoquinone (6.9 g, 30 mmol) at 0° C. After stirring at room temperature overnight, the black reaction mixture was acidified with 5N HCl at 0° C. The yellow solid that precipitated was collected by filtration, washed successively with water, methanol, diethyl ether and air-dried to give crude 12 as a deep yellow solid (7.1 g, 88%); mp>310° C. (lit.>300° C.);[Cheng 1993 JMC] TLC (chloroform/acetone, 8:1): Rf 0.47; $\nu_{max}$ (KBr) 3400 (OH), 1670 and 1620 (C═O) $cm^{-1}$; $\delta_H$ (400 MHz, DMSO-$d_6$) 7.05 (1H, d, $J_{C-5-H,\ C-4-H}$=8.54 Hz, C-4-H), 7.16 (1H, s, C-2-H), 7.2–7.7 (2H, m, C-8-H and C-9-H), 7.95 (1H, d, $J_{C-4-H,\ C-5-H}$=8.5 Hz, C-5-H), 8.2–8.7 (2H, m, C-7-H and C-10-H) and 10.53 (1H, br s, exchanged with $D_2O$, C-3-OH); MS m/z (FAB+) 265.1 [70, $(M+H)^+$], 255.3 (75), 243.2 (30), 173.2 (100); MS m/z (FAB−) 263.1 [100, $(M-H)^-$], 242.1 (20), 210.1 (25), 198.1 (45), 181.1 (35); Acc. MS (FAB+) 265.0502 $C_{16}H_9O_4$ requires 265.0501.

Benzo[b]naphtlio[2,3-d]furan-6,11-dione 3-O-sulphamate (13)

Upon sulphamoylation, 12 (500 mg, 1.892 mmol) gave a crude product (655 mg) which was fractionated by flash chromatography (chloroform/acetone, gradient). The yellow residue that obtained (510 mg) was further purified by recrystallization from acetone/hexane (1:3) to give 13 as white crystals (450 mg, 69%); mp>270° C. (dec); TLC (chloroform/acetone, 8:1): Rf 0.28; $\nu_{max}$ (KBr) 3280, 3380 ($NH_2$), 1680 (C═O), 1380 ($SO_2$) $cm^{-1}$; $\delta_H$ (270 MHz, DMSO-$d_6$) 7.52 (1H, dd, $J_{C-5-H,\ C-4-H}$=8.4 Hz and $J_{C-2-H,\ C-4-H}$=2.0 Hz, C-4-H), 7.85–8.0 (3H, m, Ar), 8.1–8.2 (2H, m, Ar), 8.25 (2H, br s, exchanged with $D_2O$, $SO_2NH_2$) and 8.27 (1H, d, $J_{C-7-H,\ C-6-H}$=8.4 Hz, C-7-H or C-10-H); MS m/z (FAB+) 344.1 [100, $(M+H)^+$], 263.1 [30, $(M-SO_2NH_2)^+$]; MS m/z (FAB−) 242.2 [100, $(M-H)^-$]; 264.2 [20, $(M-SO_2NH)^-$]; Acc. MS (FAB+) 344.0218 $C_{16}H_{10}NO_6S$ requires 344.0229. Found C, 55.83; H, 2.68; N, 3.96; $C_{16}H_9NO_6S$ requires C, 55.98; h, 2.64; N, 4.08%.

Sulphonyldiphenyl-4,4'-O,O-bis-sulphamate (14)

Upon sulphamoylation, 4,4'-sulphonyldiphenol (1.0 g, 3.996 mmol) gave a brown residue (1.56 g). A sample of this crude material (150 mg) was purified by fractionating on preparative TLC using chloroform/acetone (gradient). The pale white residue that obtained (117 mg) was further purified by recrystallization from acetone/hexane (1:2) to give 14 as white crystals (94 mg, 67%); mp 174–176° C.; TLC (chloroform/acetone, 4:1 and 2:1): Rfs 0.22 and 0.43 respectively; $\nu_{max}$ (KBr) 3380–3240 ($NH_2$), 1380 ($SO_2$) $cm^{-1}$; $\delta_H$ (270 MHz, acetone-$d_6$) 7.41 (4H, hr s, exchanged with $D_2O$, 2×$OSO_2NH_2$) 7.57 (4H, d, J=8.8 Hz, C-3H, C-5-H, C-3'-H and C-5'-H) and 8.12 (4H, d, J=8.8 Hz, C-2-H, C-6-H, C-2'-H and C-6'-H); MS m/z (FAB+) 562.1 [10, $(M+H+NBA)^+$], 409.0 [60, $(M+H)^+$], 330.1 [50, (M+H-$SO_2NH$)]; MS m/z (FAB−) 407.1 [100, $(M-H)^-$], 328.1 [25, $(M-SO_2NH_2)^-$], 249.1 [25, $(M+H-2\times SO_2NH_2)^-$]; Acc. MS m/z (FAB−) 406.9675 $C_{12}H_{11}N_2O_8S_3$ requires 406.9678. Found C, 35.4; H, 3.0; N, 6.71; $C_{12}H_{12}N_2O_8S_3$ requires C, 35.29; H, 2.96; N, 6.86%.

Thiodiphenyl-4,4'-O,O-bis-sulphamate (15) and 4'-hydroxy-thiodiphenyl-4-O-sulphamate (16)

Upon sulphamoylation, 4,4'-thiodiphenol (760 mg, 3.482 mmol) gave a crude product (1.09 g) which was fractionated by flash chromatography (chloroform/acetone, gradient). The fraction at Rf 0.42 (chloroform/acetone, 2:1) gave a beige residue that (889 mg) which was further purified by recrystallization from acetone/hexane (1:2) to give 15 as white crystals (665 mg, 50%); mp 142–144° C.; TLC (chloroform/acetone, 4:1): Rfs 0.25; $\nu_{max}$ (KBr) 3400–3220 ($NH_2$), 1590, 1390 ($SO_2$) $cm^{-1}$; $\delta_H$ (270 MHz, acetone-$d_6$) 7.22 (4H, br s, exchanged with $D_2O$, 2×$OSO_2NH_2$) 7.34 (4H, d, J=8.8 Hz, C-3-H, C-5-H, C-3'-H and C-5'-H) 7.44 (4H, d, J=6.6 Hz, C-2-H, C-6-H, C-2'-H and C-6'-H); MS m/z (FAB+) 530.1 [10, (M+H+NBA)] 376.0 [100, $(M)^+$], 297.0 [40, $(M+H-SO_2NH_2)^+$]; 217.1 [20, $(M+H-2\times SO_2NH_2)^+$]; MS m/z (FAB−) 529.2 [10, $(M+NBA)^-$], 375.1 [100, $(M-H)^-$], 296.1 [40, $(M-SO_2NH_2)^-$]; 216.1 [10, $(M-2SO_2NH_2)^-$]; Acc. MS (FAB+) 376.9905 $C_{12}H_{13}N_2O_6S_3$ requires 376,9936. Found C, 38.8; H, 3.24; N, 7.37; $C_{12}H_{12}N_2O_6S_3$ requires C, 38.29; H, 3.21; N, 7.44%.

The fraction at Rf 0.57 (chloroform/acetone, 2:1) gave a white residue (123 mg) which was further purified by recrystallization from ethyl acetone/hexane (1:4) to give 16 as white crystals (110 mg, 10%); mp 170–172° C. (dec); TLC (chloroform/acetone, 4:1): Rfs 0.35 $\nu_{max}$ (KBr) 3500–3000 ($NH_2$ and OH), 1390 ($SO_2$) $cm^{-1}$; $\delta_H$ (400 MHz, acetone-$d_6$) 6.73 (211, br s, exchanged with $D_2O$, C-4-$OSO_2NH_2$), 6.95 (2H, d, J=8.5 Hz, C-3'-H and C-5'-H), 7.18 (2H, d, J=8.8 Hz, C-2-H C-6-H or C-2'-H and C-6'-H or C-3-H, C-5-H), 7.25 (2H, d, J=8.8 Hz C-2-H, C-6-H or C-2'-H and C-6'-H), 7.42 (2H, d, J=8.5 Hz, C-3-H, C-5-H or C-2-H, C-6-H) and 8.97 (1H, br s, exchanged with $D_2$, C-4'-OH); MS m/z (FAB+) 297.0 [100, $(M)^+$], 217.1 [20, $(M-SO_2NH_2)^+$]; MS m/z (FAB−) 450.1 [20, $(M+NBA)^-$], 296.1 [100, $(M-H)^-$]; 216.1 [20, $(M-H-SO_2NH_2)^-$]; Acc. MS (FAB+) 297.0129 $C_{12}H_{11}NO_4S_2$ requires 297.0129. Found C, 48.2; H, 3.89; N, 4.57; $C_{12}H_{11}NO_4S_2$ requires C, 48.47; H, 3.73; N, 4.71%.

4,4'Dihydroxydiphenylmethane (17)

To a solution of 4,4'-dihydroxybenzophenone (1.0 g, 4.668 mmol) in ethanol (25 mL) Pd-C (10%, 200 mg) was added and the resulting suspension was subjected to hydrogenation at balloon pressure at room temperature for 6 h. Upon removal of the supported catalyst by filtration, the filtrate was evaporated to give a white residue (1.02 g) which was recrystallized from ethyl acetate/hexane (1:2) to give 17 as white crystals (854 mg, 91%); mp 158–160° C. (lit. 161–162° C.);*Levine 1957 JOC* TLC (chloroform/acetone, 8:1 and 4:1): Rfs 0.28 and 0.63 respectively; $\nu_{max}$ (KBr) 3500–3000 (OH), 1600$cm^{-1}$; $\delta_H$ (270 MHz, acetone-$d_6$) 3.8 (2H, s, —$CH_2$—), 6.75 (4H, m, C-3-H, C-3'-H, C-5-H, C-5'-H), 7.03 (4H, m, C-2-H, C-2'-H, C-6-H, C-6'-H) and 8.1 (2H, br s, exchanged with $D_2O$, C-4-OH and C-4'-OH); MS m/z (FAB+) 200.1 [100, $(M)^+$]; Acc. MS (FAB+) 200.0842 $C_{13}H_{12}O_2$ requires 200.0915.

4,4'-Bis-sulphamoyloxydiphenylmethane (18) and 4-sulphamoyloxy-4'-hydroxydiphenylmethane (19)

Upon sulphamoylation, 17 (825 mg, 4.120 mmol) gave a beige crude product (1.3 g) which was fractionated by flash chromatography (chloroform/acetone, gradient). The fraction that collected with an Rf 0.43 (chloroform/acetone, 4:1) gave a white residue upon evaporation (471 mg) which was further purified by recrystallization from acetone/chloroform (1:2) to give 18 as white crystals (389 mg, 26%); mp 175–177° C.; $\nu_{max}$ (KBr) 3500–3000 ($NH_2$), 1390 ($SO_2$) $cm^{-1}$; $\delta_H$ (270 MHz, acetone-$d_6$) 4.03 (2H, s, —$CH_2$—), 7.10 (4H, br s, exchanged with $D_2O$, 2×$OSO_2N112$), 7.25 (4H, d, J=8.8 Hz, C-2-H, C-2'-H, C-6H and C-6'-H) and 7.34 (4H, d, J=8.8 Hz, C-3-H, C-3'-H, C-5-H and C-5'-H); MS m/z (FAB+) 512.0 [40, $(M+H+NBA)^+$], 358.0 [90, $(M)^+$], 279.0 [50, $(M+H-SO_2NH_2)^+$]; MS m/z (FAB−) 511.1 [40, $(M+NBA)^+$],357.1 [100, $(M-H)^+$], 278.0 [30, $(M-SO_2NH_2)^+$]. Found C, 43.5; H, 3.89; N, 7.64; $C_{13}H_{14}O_6N_2S_2$ requires C, 43.57; H, 3.94; N, 7.82%.

The fraction that collected with an Rf 0.52 ($CH_3Cl$/acetone, 4:1) gave a beige residue (150 mg) which was recrystallized from acetone/hexane (1:2) to give 19 as white crystals (120 mg, 10%); mp 128–130° C.; TLC (chloroform/acetone, 8:1): Rf 0.27; $\nu_{max}$ (KBr) 3500–3300 ($NH_2$), 3240 (OH) 1390 ($SO_2$) $cm^{-1}$; $\delta_H$ (270 MHz, acetone-$d_6$) 3.90 (2H, 5, —$CH_2$—), 6.77 (2H, d, $J_{C-2'-H,\ C-3'-H}$, $J_{C-6'-H,\ C-5'-H}$8.8 Hz, C-3'-H and C-5'-H), 7.07 (4H, d, $J_{C-2-H,\ C-3-H}$=8.1 Hz, 2H exchanged with $D_2O$, Ar and C-4-$OSO_2NH_2$), 7.21 (2H, d, J=8.8 Hz, Ar), 7.28 (2H, d, J=8.8 Hz, Ar) and 8.18 (1H, br s, exchanged with $D_2O$, C-4'-OH); MS m/z (FAB+) 279.0 [100, $(M)^+$], 200.1 [30, $(M+H-SO_2NH_2)^+$]; MS m/z (FAB−) 432.2 [40, $(M+NBA)^-$], 278.1 [100, $(M-H)^-$]; Acc. MS (FAB+) 279.0584 $C_{13}H_{13}O_4NS$ requires 279.0643. Found C, 56.0; H, 5.16; N, 4.74; $C_{13}H_{13}O_4NS$ requires C, 55.90; H, 4.69; N,.5.01%.

(1,3-Adamantanediyl)diphenyl-4,4'-O,O-bis-sulphamate (20) 4'-hydroxy-(1,3-adamantanediyl)diphenyl-4-O-sulphamate (21)

Upon sulphamoylation, 4,4'-(1,3-adamantanediyl)diphenol (210 mg, 655 μmol) gave a crude product (273 mg)

which was fractionated by flash chromatography (chloroform/acetone, gradient). The fraction at Rf 0.25 ($CH_3Cl$/acetone, 4:1) gave a white residue (159 mg) which was further purified by recrystallization from acetone/hexane (1:2) to give 20 as white crystals (112 mg, 36%); mp 197–199° C.; $\nu_{max}$ (KBr) 3420–3240 ($NH_2$), 1390 ($SO_2$) $cm^{-1}$; $\delta_H$ (270 MHz, acetone-$d_6$) 1.8–2.25 (4H, in), 7.12 (4H, br s, exchanged with $D_2O$, 2×$SO_2NH_2$), 7.24–7.32 (4H, AA'BB', Ar), 7.48–7.56 (4H, AA'BB', Ar); MS m/z (FAB+) 478.1 [80, $(M)^+$], 399.2 [30, $(M+H\text{-}SO_2NH_2)^+$]; MS m/z (FAB−) 631.2 [30, $(M+NBA)^-$], 477.2 [100, $(M\text{-}H)^-$], 398.2 [20, $(M\text{-}SO_2NH_2)$]; Acc. MS (FAB+) 478.1227 $C_{22}H_{26}N_2S_2$ requires 478.1232. Found C, 55.1; H, 5.63; N, 5.85; $C_{22}H_{26}N_2O_6S_2$ requires C, 55.21; H, 5.48; N, 5.85%.

The fraction at Rf 0.39 (chloroform/acetone, 4:1) gave a white residue (38 mg) which was further purified by recrystallization from ethyl acetate/hexane (1:2) to give 21 as white crystals (20 mg, 8%); mp 140–142° C.; $\nu_{max}$ (KBr) 3500–3000 ($NH_2$ and OH), 1370 ($SO_2$) $cm^{-1}$; $\delta_H$ (270 MHz, acetone-$d_6$) 1.8–2.29 (14H, m), 6.78 (2H, d, J=8.8 Hz, C-3'-H and C-5'-H), 7.08 (2H, br s, exchanged with $D_2O$, C-4-$SO_2NH_2$), 7.26 (4H, br d, J=8.79 Hz, Ar), 7.5 (2H, d, J=8.8 Hz, Ar) and 8.15 (1H, br s, exchanged with $D_2O$, C-4'-OH); MS m/z (FAB+) 399.1 [100, $(M)^+$], 320.2 [15, $(M+H\text{-}SO_2NH_2)^-$], 306.1 (45), 288.1 (15); MS m/z (FAB−) 552.3 [30, $(M+NBA)^-$], 398.2 [100, $(M\text{-}H)^-$]; Acc. MS (FAB+) 400.1533 $C_{22}H_{26}NO_4S$ requires 400.1583.

4,4'-(Di-tert-butyldimethylsilyloxy)benzophenone (22)

To a solution of 4,4'-dihydroxybenzophenone (5.0 g, 23.34 mmol) in anhydrous DMF (15 mL), tert-butyldimethylchlorosilane (4.22 g, 28 inmol) and imidazole (4.0 g, 58.75 mmol) were added and the reaction mixture stirred under $N_2$ for 3 h. After dilution with 5% aqueous $NaHCO_3$ (100 mL) and ethyl acetate (200 mL), the organic layer that separated was washed with water, brine, dried ($MgSO_4$), filtered and evaporated to give 22 as a pale white oil, which solidified on standing (10 g, 97%); TLC (chloroform): Rf 0.69; $\nu_{max}$ (KBr) 1620 (C═O) $cm^{-1}$; $\delta_H$ (400 MHz, $CDCl_3$) 0.24 (12H, s, 2×1.0 -$Si(CH_3)_2$), 1.0 (18H, s, 2×$(CH_3)_3$, 6.9 (4H, AA'BB', C-3-H, C-5-H, C-3'-H and C-5'-H) and 7.73 (4H, AA'BB', C-2-H, C-6-H, C-2'-H and C-6'-H); MS m/z (FAB+) 443.4 [60, $(M+H)^+$], 385.3 [10, $(M\text{-}C(CH_3)_3)^+$], 235 (90), 73.0 (100); MS m/z (FAB−) 441.3 [10, $(M\text{-}H)^-$], 401.2 (10), 327.2 [100, $(M\text{-}H\text{-}2\times C(CH_3)_3)^+$], 255.1 (10). Found C, 67.6; H, 8.64; $C_{25}H_{38}O_3Si_2$ requires C, 67.82; H, 8.65%.

1-Cyclohexyl-1,1-di-[(4-(tert-butyldimethylsilyloxy)phenyl]methanol (23)

To a solution of 22 (500 mg, 1.129 mmol) in dry ether (50 mL), cyclohexyl magnesium chloride (1.2 mL, 2.4 minol) was added dropwise with stirring at 0° C. under $N_2$. The reaction mixture after being stirred overnight at room temperature was diluted with dil HCl and extracted with ether. The combined ethereal extracts were washed with water, brine, dried ($MgSO_4$), filtered and evaporated to give crude 23 as a pale white oil (550 mg, 92%). TLC analysis of this crude has shown a single spot although $^1H$ NMR has indicated the presence of starting material (ca. 10–20%); TLC (chloroform): Rf 0.61; $\nu_{max}$ (film) 3420 (OH), 1600 $cm^{-1}$; $\delta_H$ (400 MHz, DMSO-$d_6$) 0.14 (12H, s, 2×-$Si(CH_3)_2$), 0.92 (18H, s, 2×$(CH_3)_3$), 0.96–2.32 (11H, m), 4.95 (1H, s, exchanged with $D_2O$, OH), 6.7 (4H, d, J=8.5 Hz, C-3-H, C-5-H, C-3'-H and C-5'-H) and 7.31 (4H, d, J=8.8 Hz, C-2-H, C-6-H, C-2'-H and C-6'-H); MS m/z (FAB+) 525.5 [30, $(M\text{-}H)^+$], 443.4 [100, $(M\text{-}cyclohexyl)^+$], 427.4 (50), 319 (20), 73.0 (60); MS m/z (FAB−) 679.0 [10, $(M+NBA)^-$], 525.5 [40, $(M\text{-}H)^-$], 441.3 [20, $(M\text{-}H\text{-}cyclohexyl)^-$], 411.4 (100), 327.3 [50, $(M\text{-}cyclohexane\text{-}Si(CH_3)_2C(CH_3)_3]^-$, 317.3 (40); Acc. MS (FAB+) 526.3214 $C_{31}H_{50}O_3Si_2$ requires 526.3298%.

1-Cyclohexyl-1, 1-di-(4-hydroxyphenyl)methanol (24)

To a solution of 23 (500 ing, 950 μmol) in dry THF (10 mL) tetra-n-butylammonium fluoride (5.6 mL of 1M in THF, 5.68 mmol) was added dropwise. The resulting mixture was stirred for about 5–10 minutes and then diluted with ethyl acetate (100 mL). The organic layer was washed with water (100 mL), dried ($MgSO_4$), filtered and evaporated to give a white solid (280 mg) which was recrystallized from acetone/hexane (1:2) to give 24 as white crystals (260 mg, 92%); mp 115–117° C.; TLC (chloroform and chloroform/acctone, 8:1): Rfs 0.21 and 0.52; $\nu_{max}$ (KBr) 3500–3140 (OH), 1600 $cm^{-1}$; $\delta_H$ (400 MHz, DMSO-$d_6$) 0.96–2.26 (11H, m), 4.74 (1H, s, exchanged with $D_2O$, OH), 6.66 (4H, d, J=8.8 Hz C-3-H, C-5-H, C-3'-H and C-5'-H), 7.21 (4H, d, J=8.8 Hz C-2-H, C-6-H, C-2'-H and C-6'-H) and 9.1 (2H, s, exchanged with $D_2O$, 2×OH); MS m/z (FAB+) 298.2 [10, $(M)^+$], 215.1 [100, M-cyclohexy]$^+$, 205.2 (15); MS m/z (FAB−) 451.3 [40, $(M+NBA)^-$], 297.3 [100, $(M\text{-}H)^-$], 279.3 (30), 213.2 [30, $(M\text{-}H\text{-}cyclohexane)^-$]; Acc. MS (FAB+) 298.1558 $C_{19}H_{22}O_3$ requires 298.1569.

1-Cyclohexyl-1,1-di-(4-sulphamoyloxyphenyl)methanol (25)

To a solution of 24 (150 mg, 503 μmol) and 2,6-di-tert-butyl-4-methylpyridine (DBMP) (930 mg, 4.529 mmol) in $CH_2Cl_2$ (25 mL) was added dropwise with stirring a freshly concentrated solution of sulphainoyl chloride in toluene (ca. 0.7 M, 3.0 mmol). After 2 h of stirring, the solution was diluted with dichloromethane (100 mL). The organic layer was washed with water, brine, dried ($MgSO_4$), filtered and evaporated to give a residue (450 mg) which was fractionated by flash chromatography (chloroform/acetone, gradient). The white solid that obtained (180 mg) was further purified by recrystallization from acetone/hexane (1:2) to give 25 as pale white crystals (120 mg, 52%); mp 213–215° C. (dec); TLC (chloroform and chloroform/acetone, 8:1); Rfs 0.12 and 0.31 respectively; $\nu_{max}$ (KBr) 3500–3000 ($NH_2$), 1600, 1380 ($SO_2$) $cm^{-1}$; $\delta_H$ (400 MHz, DMSO-$d_6$) 1.31 (1H, br s), 1.57 (6H, br s), 2.15 (4H, br s), 7.25 (811, m, Ar-H), 8.0 (411, br s, exchanged with $D_2O$, $OSO_2NH_2$) and 9.68 (1H, br s, exchanged with $D_2O$, OH); MS m/z (FAB+) 457.1 [10, $(M+H)^+$], 206.2 (100); MS m/z (FAB−) 608.2 [40, $(M\text{-}H+NBA)^-$], 455 [15, $(M\text{-}H)^-$], 249.0 (100); Acc. MS (FAB+) 457.1065 $C_{19}H_{25}N_2O_7S_2$ requires 457.1103.

3,3'-Dinitrobenzophenone (26)

To a stirred mixture of benzophenone (10 g, 54.88 mmol) in conc. sulphuric acid (55 mL) at room temperature was added a mixture of conc. nitric acid (6 mL) and conc. sulphuric acid (14 mL). The reaction mixture was then slowly heated to 75° C., and maintained at this temperature for 30 mim. After cooling to room temperature, the reaction mixture was poured onto crushed ice. The gummy mass that formed hardened over time and after being grinded into powder was washed with water until the washings were neutral. The cake/powder that collected was air-dried and recrystallised from butanone (73 mL). The solid that formed after overnight was washed first with butanone and then with ethanol to give crude 26 as a yellow solid (7.9 g, 53%). An analytical sample was further recrystallized from methanol to give 26 as pale yellow crystals; mp 144–146° C. (lit. 148–149° C.);[Klemm 1958 JOC] TLC (chloroform/acetone, 8:1): Rf 0.8; $\nu_{max}$ (KBr) 1670 (C═O) $cm^{-1}$; $\delta_H$ (270 MHz, CDCl$_3$) 7.78 (2H, t, J=7.9 Hz C-5-H and C-5'-H), 8.15 (2H, dt, J=7.7 and ~2 Hz, C-4-H and C-4'-H or C-6-H and C-6'-H), 8.53 (2H, ddd, J=8.2 and ~1–2 Hz, C-6-H and C-6'-H or C-4-H and C-4'-H) and 8.64 (2H, t, J~2 Hz, C-2-H and C-2'-H); MS m/z (FAB+) 273.0 [100, (M+H)$^+$], 259.1 (90), 243.1 (50); MS m/z (FAB−) 425.2 [30, (M+NBA)$^−$], 272.1 [100, (M)$^−$], 257.2 (10); Acc. MS (FAB+) 273.0500 C$_{13}$H$_9$N$_2$O$_5$ requires 273.0512. Found C, 57.1; H, 2.89; N, 10.30; C$_{13}$H$_8$N$_2$O$_5$ requires C, 57.36; H, 2.96; N, 10.29%.

3,3'-Dihydroxybenzophenone (27)

A mixture of 26 (5.0 g, 18.37 mmol), tin chloride (25 g, 131.9 mmol) and concentrated hydrochloric acid (35 mL) was stirred at 70° C. for 6 h. The dark yellow crystalline benzophenone-3,3'-diammonium chlorostannate that separated was collected by filtration. After re-suspending the solid collected in concentrated hydrochloric acid (35 mL) at 0° C., this cold suspension was added dropwise to a cold solution (at 0° C.) of sodium nitrite (2.56 g in 10 mL water). After the addition was completed, the suspension was stirred at 0° C. for 1 h and then quickly filtered by means of a cold glass funnel. The resulting yellow precipitate (tetrazonium salt) was added (cold, 0–5° C.) in small portions to boiling 1N sulphuric acid (100 mL). The resulting red solution was treated with charcoal for decolourization and the suspension was filtered hot. On cooling the filtrate, the yellow precipitate that formed was collected by filtration, washed with water and air-dried to give a yellow powder (1.92 g, 49%); which was recrystallized from acetone/hexane (1:2) to give 27 as yellow crystals (1.3 g, 33%); mp 161–163° C. (lit. 163–164° C.);$^{Klemm\ 1958\ JOC}$ TLC (chloroform/acetone, 8:1): Rf 0.63; $\nu_{max}$ (KBr) 3500–3000 (OH), 1630 (C=O) cm$^{-1}$; $\delta_H$ (270 MHz, acetone-d$_6$) 7.12 (2H, m, C-4-H and C-4'-H), 7.23 (4H, m, C-6-H, C-6'-H, C-2-H and C-2'-H), 7.38 (2H, t, J=8.1 Hz, C-5-H and C-5'-H) and 8.74 (2H, hr s, exchanged with D$_2$O, 2×OH); MS m/z (FAB+) 215.1 [100, (M+H)$^+$], 199.1 (10), 185.1 (15); MS m/z (FAB−) 367.2 [40, (M+NBA)$^+$], 213.1 [50, (M-H)$^−$], 139.1 (5); Acc. MS (FAB+) 215.0715 C$_{13}$H$_{11}$O$_3$ requires 215.0708.

Benzophenone-3,3'-O,O-bis-sulphamate (28) and 3'-hydroxybenzophenone-3-O-sulphamate (29)

Upon sulphamoylation, 27 (1.0 g, 4.668 mmol) gave a dark yellow residue (1.42 g) which was fractionated by flash chromatography (chloroform/acetone, gradient). The band at Rf 0.21 (chloroform/acetone, 4:1) gave a yellow residue (567 mg) which was further purified by recrystallization from acetone/hexane (1:2) to give 28 as yellow crystals (310 g, 18%); mp 141–143° C.; TLC (chloroform/acetone, 4:1): Rfs 0.42; $\nu_{max}$ (KBr) 3360–3580 (NH$_2$), 1650 (C=O), 1380 (SO$_2$); $\delta_H$ (270 MHz, acetone-d$_6$) 7.29 (4H, br s, exchanged with D$_2$O, 2×SO$_2$NH$_2$) 7.65 (4H, m, C-5-H, C-5'-H and C-4-H, C-4'-H or C-6-H, C-6'-H) and 7.77 (4H, m, C-2-H, C-2'-H and C-6-H, C-6'-H or C-4-H, C-4'-H); MS m/z (FAB+) 373.0 [100, (M+H)$^+$], 211.1 [20, (M-H-2× SO$^2$NH$_2$)$^{+1}$]; MS m/z (FAB−) 371.1 [100, (M-H)$^−$]; Acc. MS (FAB+) 373.0165 C$_{13}$H$_{13}$N$_2$O$_7$S$_2$ requires 373.0164. Found C, 42.2; H, 3.23; N, 7.21; C$_{13}$H$_{12}$N$_2$O$_7$S$_2$ requires C, 41.93; H, 3.25; N, 7.52%.

The fraction at Rf 0.56 (CH$_3$Cl/acetone, 2:1) gave a yellow residue (215 mg) which was further purified by recrystallization from ethyl acetate/hexane (1:2) to give 29 as yellow crystals (163 mg, 12%); mp 190–192° C.; TLC (chloroform/acetone, 4:1): Rfs 0.31; $\nu_{max}$ (KBr) 3220–3000 (NH$_2$ and OH), 1640 (C=O), 1400 (SO$_2$) cm$^{-1}$; $\delta_H$ (270 MHz, acetone-d$_6$) 6.64 (2H, hr s, exchanged with D$_{2O}$, C-3-OSO$_2$NH$_2$), 7.17 (1H, t, J=7.5 Hz, C-5'-H), 7.47 (2H, m, C-2'-H and C-4'-H), 7.58 (2H, dd, J=8.1 Hz C-4-H and C-5-H), 7.79 (1H, d,J=7.3 Hz, C-6'-H), 8.0 (1H, d, J=8.8 Hz, C-6-H), 8.11 (1H, s, C-2-H) and 8.87 (1H, br s, C-3-OH); MS m/z (FAB+) 447.1 [10, (M+H+NBA)$^+$], 294.0 [100, (M+H)$^+$], 214.1 [10, (M+H-SO$_2$NH$_2$)$^+$]; MS m/z (FAB−) 446.1 [20, (M+NBA)$^−$], 292.0 [100, (M-H)$^−$], 213.0 [30, (M-SO$_2$NH$_2$)]; Acc. MS (FAB+) 294.0411 C$_{13}$H$_{11}$NO$_5$S requires 294.0436.

ACKNOWLEDGEMENT

We thank Sterix Ltd for financial support of this work.

TABLE 1

Inhibition of oestrone sulphatase activity in intact MCF-7 breast cancer cells by sulphamates 3–16, 18–21, 25, 28–29.

| | % Inhibition of E1-STS activity in MCF-7 cells | | |
|---|---|---|---|
| Compound | 0.1 μM | 1 μM | 10 μM |
| 3 | 71.41 ± 6.85 | 95.64 ± 2.07 | 98.69 ± 2.82 |
| 4 | 46.3 ± 13.6 | 83.5 ± 1.9 | 93.9 ± 1.2 |
| 5 | 34.8 ± 1.7 | 83.8 ± 0.5 | 96.7 ± 1.0 |
| 6 | <10 | 33.04 ± 10.68 | 87.89 ± 2.02 |
| 7 | <10 | 24.34 ± 11.89 | 83.81 ± 0.17 |
| 8 | <10 | 33.04 ± 10.68 | 87.89 ± 2.02 |
| 9 | 21.3 ± 1.5 | 67.9 ± 1.9 | 97.1 ± 0.8 |
| 10 | 93.1 ± 2.1 | 98.6 ± 1.0 | 99.1 ± 0.1 |
| 11 | 99.3 ± 0.6 | 94.5 ± 1.6 | 90.1 ± 0.8 |
| 13 | 46.6 ± 4.5 | 93.9 ± 0.8 | 98.6 ± 0.3 |
| 14 | <10 | 50.6 ± 3.3 | 87.4 ± 2.7 |
| 15 | 67.2 ± 1.1 | 96.6 ± 1.4 | 99.7 ± 0.1 |
| 16 | 26.6 ± 4.3 | 83.9 ± 1.2 | 97.7 ± 0.4 |
| 18 | 22.2 ± 0.1 | 50.01 ± 0.1 | 93.3 ± 0.1 |
| 19 | <10 | 39.3 ± 0.1 | 92.4 ± 0.1 |
| 20 | 16.1 ± 4.0 | 32.7 ± 2.3 | 90.1 ± 0.7 |
| 21 | <10 | 16.3 ± 1.5 | 64.1 ± 1.1 |
| 25 | <10 | 27.4 ± 0.8 | 75.1 ± 2.8 |
| 28 | 75.3 ± 0.8 | 98.4 ± 0.3 | 99.9 ± 0.1 |
| 29 | <10 | 30.7 ± 5.6 | 87.2 ± 1.8 |

TABLE 2

Inhibition of oestrone sulphatase activity in placental microsomes by sulphamates 3–16, 18–21, 25, 28–29.

| | % Inhibition of E1-STS activity in placental microsomes | | | |
|---|---|---|---|---|
| Compound | 10 μM | 25 μM | 50 μM | 100 μM |
| 3 | 98.17 ± 0.05 | ND | 99.03 ± 0.05 | 99.2 ± 0.0 |
| 4 | 85.3 ± 1.4 | 92.1 ± 0.0 | 94.7 ± 0.4 | 96.6 ± 0.1 |
| 5 | 62.1 ± 1.4 | 82.0 ± 0.4 | 88.1 ± 0.3 | 92.8 ± 0.2 |
| 6 | 76.73 ± 2.47 | ND | 88.04 ± 0.82 | 92.28 ± 0.41 |
| 7 | 47.41 ± 0.05 | ND | 75.11 ± 1.37 | 82.77 ± 0.23 |
| 8 | 71.27 ± 2.42 | ND | 75.79 ± 2.06 | 80.51 ± 1.87 |
| 9 | 28.8 ± 3.2 | 48.5 ± 0.5 | 62.0 ± 2.8 | 75.8 ± 1.2 |
| 10 | 91.3 ± 0.7 | 95.7 ± 0.5 | 97.2 ± 0.3 | 97.7 ± 0.1 |
| 11 | 86.1 ± 0.5 | 91.2 ± 0.2 | 94.4 ± 0.5 | 95.6 ± 0.1 |
| 13 | −28.0 ± 1.1 | −37.7 ± 1.8 | −31.8 ± 1.3 | −36.2 ± 1.8 |
| 14 | 65.0 ± 1.8 | 85.5 ± 0.6 | 92.3 ± 0.3 | 95.4 ± 0.2 |
| 15 | 65.3 ± 0.9 | 79.4 ± 0.9 | 87.4 ± 0.9 | 91.9 ± 0.4 |
| 16 | 33.1 ± 1.7 | 49.5 ± 0.1 | 64.7 ± 0.9 | 76.8 ± 0.4 |
| 18 | 22.1 ± 0.6 | 29.4 ± 0.1 | 38.7 ± 4.9 | 53.1 ± 0.1 |
| 19 | 11.7 ± 2.3 | 17.3 ± 2.7 | 22.8 ± 1.4 | 34.3 ± 1.0 |
| 20 | 31.4 ± 1.6 | 41.9 ± 2.3 | 62.5 ± 7.5 | 69.0 ± 4.8 |
| 21 | <10 | 15.9 ± 0.9 | 32.5 ± 1.1 | 60.1 ± 3.4 |
| 24 | <10 | 20.0 ± 1.6 | 33.4 ± 2.2 | 44.7 ± 0.4 |
| 28 | 51.1 ± 3.7 | 73.6 ± 1.9 | 84.1 ± 1.9 | ND |
| 29 | 18.8 ± 1.3 | 30.7 ± 3.4 | 43.7 ± 2.6 | 58.3 ± 0.1 |

ND = not determined

REFERENCES

Purohit, A.; Vernon, K. A.; Wagenaar Hummelinek, A. B.; et. al. *J. Steroid Biochem. Mol. Biol.* 1998, 64, 269.

Li, P. K.; Chu, G. H.; Guo, J. P. et. al. *Steroids* 1998, 63, 425.

Ciobanu, L. C.; Boivin, R. P.; Luu-The, V.; et. al. *J. Med. Chem.* 1999, 42, 2280.

Boivin, R. P.; Labrie, F.; Poirier, D; et. al. *Steroids* 1999, 64, 825.

Hoffmann, R.; Rot, A.; Nijyama, S; Billich, A. *J. Invest. Dermatol.* 2001, 117, 1342.

Hoffmann, R.; Happle, R. *Eur. J. Dermatol.* 2000, 10, 319.

Li, P. K.; Rhodes, M. F.; Jagannathan, S; et. al. *Cognit. Brain Res.* 1995, 2, 251.

Johnson, D. A.; Wu, T.; Li, P.; Maher, T. *J. Brain Res.* 2000, 865, 286.

Suitters, A. J.; Shaw, S.; Wales, M. R.; et. al. *Immunology,* 1997, 91, 314.

Woo, L. W. L.; Purohit, A.; Malini, B; et. al. *Chem. & Biol.* 2000, 7, 773.

Ciobanu, L. C.; Luu-The, V.; Poirier, D; et. al. *J. Steroid Biochem. Mol. Biol.* 2002, 80, 339.

Woo, L. W. L.; Howarth N. M.; Purohit A.; et. al. *J. Med. Chem..* 1998, 41, 1068.

Reed, M. J., Purohit, A.; Woo, L. W. L.; et. al. *Endocrine-Related Cancer,* 1996, 3, 9.

Howarth, N. M.; Purohit, A.; Reed, M. J.; et. al. *J. Med. Chem.* 1994, 37, 219.

Cheng. C. C.; Dong, Q.; Liu, D. F.; et. al. *J. Med. Chem.* 1993, 36, 4108.

Levine, M.; Temin, S. C. *J. Org. Chem.* 1957, 22, 85.

Klemm, L. H.; Mann, R.; Lind, C.D. *J. Org. Chem.* 1958, 23, 349.

Meyer, C. Y.; Lombardini, G.; Bonoli, L. *J. Am. Chem. Soc.* 1962, 84, 4603.

Nussbaumer, P.; Bilban, M.; Billich, A. *Bioorg. Med. Chem. Lett.,* 2002, 12, 2093.

Albert, A.; Serjeant, E. P. In *The Determination of Ionization Constants;* Chapman and Hall: New York.

Woo, L. W. L.; Lightowler, M.; Purohit, A.; et. al. *J. Steroid Biochem. Mol. Biol.* 1996, 57, 79.

Duncan, L.; Purohit, A.; Howarth, N. M.; et. al. *Cancer Res.* 1993, 53, 298.

The invention claimed is:

1. A compound of Formula IVa

Formula IVa

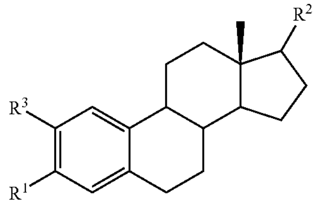

wherein $R^1$ and $R^2$ are sulphamate groups, wherein each sulphamate group is independently selected from sulphamate groups of the formula

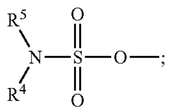

wherein each of $R^4$ and $R^5$ is independently selected from H and hydrocarbyl; and wherein $R^3$ is a hydrocarbyl or oxyhydrocarbyl group.

2. The compound according to claim 1, wherein $R^3$ is an oxyhydrocarbyl group.

3. The compound according to claim 1, wherein $R^3$ is an alkoxy group.

4. The compound according to claim 3, wherein the alkoxy group is methoxy.

5. The compound according claim 1, wherein $R^3$ is a hydrocarbyl group.

6. The compound according to claim 1, wherein $R^3$ is an alkyl group.

7. The compound according to claim 6, wherein the alkyl group is methyl or ethyl.

8. The compound according to claim 1, wherein each of $R^4$ and $R^5$ is independently selected from H, alkyl, cycloalkyl, alkenyl and aryl, or together represent alkylene optionally containing one or more hetero atoms or groups in the alkylene chain.

9. The compound according to claim 1, wherein at least one of $R^4$and $R^5$ is H.

10. The compound according to claim 1, wherein both of $R^4$ and $R^5$ is H.

11. The compound according to claim 1, wherein $R^1$ is 3-$OSO_2NH_2$, $R^2$ is 17-β-$OSO_2NH_2$ and $R^3$ is 2-OMe.

* * * * *

UNITED STATES PATENT AND TRADEMARK OFFICE

CERTIFICATE OF CORRECTION

PATENT NO. : 7,119,081 B2
APPLICATION NO. : 10/367114
DATED : October 10, 2006
INVENTOR(S) : Potter et al.

It is certified that error appears in the above-identified patent and that said Letters Patent is hereby corrected as shown below:

Column 94, Claim 5 line 30 should read,

The compound according --to-- claim 1, wherein $R^3$ is hydrocarbyl group.

Signed and Sealed this

Twentieth Day of November, 2007

JON W. DUDAS

*Director of the United States Patent and Trademark Office*